(12) United States Patent
Hatada et al.

(10) Patent No.: US 11,591,623 B2
(45) Date of Patent: Feb. 28, 2023

(54) DNA METHYLATION EDITING KIT AND DNA METHYLATION EDITING METHOD

(71) Applicant: NATIONAL UNIVERSITY CORPORATION GUNMA UNIVERSITY, Gunma (JP)

(72) Inventors: Izuho Hatada, Gunma (JP); Sumiyo Morita, Gunma (JP); Takuro Horii, Gunma (JP)

(73) Assignee: NATIONAL UNIVERSITY CORPORATION GUNMA UNIVERSITY, Gunma (JP)

( * ) Notice: Subject to any disclaimer, the term of this patent is extended or adjusted under 35 U.S.C. 154(b) by 397 days.

(21) Appl. No.: 16/801,969

(22) Filed: Feb. 26, 2020

(65) Prior Publication Data
US 2020/0190543 A1 Jun. 18, 2020

Related U.S. Application Data

(62) Division of application No. 15/779,227, filed as application No. PCT/JP2016/084958 on Nov. 25, 2016, now Pat. No. 10,612,044.

(30) Foreign Application Priority Data

Nov. 25, 2015 (JP) ................................ 2015-229896

(51) Int. Cl.
| | |
|---|---|
| *C12N 15/85* | (2006.01) |
| *C12N 15/90* | (2006.01) |
| *C07K 16/18* | (2006.01) |
| *C12N 5/10* | (2006.01) |
| *C12N 9/10* | (2006.01) |
| *C12N 15/09* | (2006.01) |
| *C07K 16/44* | (2006.01) |
| *C12N 1/00* | (2006.01) |
| *C12N 15/11* | (2006.01) |

(52) U.S. Cl.
CPC ............ *C12N 15/907* (2013.01); *C07K 16/18* (2013.01); *C07K 16/44* (2013.01); *C12N 1/00* (2013.01); *C12N 5/10* (2013.01); *C12N 9/10* (2013.01); *C12N 15/09* (2013.01); *C12N 15/111* (2013.01); *C07K 2317/622* (2013.01); *C07K 2319/01* (2013.01); *C07K 2319/21* (2013.01); *C07K 2319/60* (2013.01); *C07K 2319/80* (2013.01); *C12N 2310/20* (2017.05); *C12Y 201/01037* (2013.01)

(58) Field of Classification Search
None
See application file for complete search history.

(56) References Cited

U.S. PATENT DOCUMENTS

| | | |
|---|---|---|
| 2016/0010076 A1 | 1/2016 | Joung et al. |
| 2017/0219596 A1 | 8/2017 | Tanenbaum |

FOREIGN PATENT DOCUMENTS

| | | |
|---|---|---|
| WO | 2014/152432 | 9/2014 |

OTHER PUBLICATIONS

Tanenbaum et al., "A Protein-Tagging System for Signal Amplification in Gene Expression and Fluorescence Imaging", Cell, vol. 159, 2014, pp. 635-646.
Maeder et al., "Targeted DNA demethylation and activation of endogenous genes using programmable TALE-TET1 fusion proteins", Nature Biotechnology, 2013, vol. 31, No. 12, pp. 1137-1142.
Mali et al., "Cas9 as a versatile tool for engineering biology", Nature Methods, vol. 10, No. 10, 2013, pp. 957-963.
Yamazaki et al., BMB 2015 Koen Yoshishu, 2015, #1P0832 withits partial English translation.
Shen et al., "A single amino acid substitution confers enhanced methylation activity of mammalian Dnmt3b on chromatin DNA", Nucleic Acids Research, 2010, vol. 38, No. 18, pp. 6054-6064.
Cabantous et al., "A New Protein-Protein Interaction Sensor Based on Tripartite Split-GFP Association", Scientific Reports, 2013, vol. 3, No. 2854, 9 pages.
Skelton et al., "Origins of PDZ Domain Ligand Specificity", The Journal of Biological Chemistry, 2003, vol. 278, No. 9, pp. 7645-7654.
Morita et al., "Targeted DNA demethylation in vivo using dCas9-peptide repeat and scFv-TET1 catalytic domain fusions", Nature Biotechnology, vol. 34, No. 10, 2016, pp. 1060-1065.
Hatada et al., Jikken Igaku, vol. 32, No. 11, 2014, pp. 1690-1714, with partial English translation.
International Search Report dated Jan. 31, 2017 in International Application No. PCT/JP2016/084958.
International Preliminary Report on Patentability dated May 31, 2018 in International Application No. PCT/JP2016/084958.
Extended European Search Report dated Apr. 5, 2019 in corresponding European Patent Application No. 16868667.3.
Bernstein et al., "TALE-mediated epigenetic suppression of CDKN2A increases replication in human fibroblasts", The Journal of Clinical Investigation, 2015, vol. 125, No. 5, pp. 1998-2006.
Schultz et al (Nature Structural and Molecular Biology 1998, vol. 5, No. 1, pp. 19-24, abstract).

*Primary Examiner* — Celine X Qian
(74) *Attorney, Agent, or Firm* — Wenderoth, Lind & Ponack, L.L.P.

(57) ABSTRACT

A DNA methylation editing kit comprises: (1) a fusion protein of inactivated CRISPR-associated endonuclease Cas9 (dCas9) having no nuclease activity and a tag peptide array in which plural tag peptides are linked by linkers, or an RNA or DNA coding therefor; (2) a fusion protein(s) of a tag peptide-binding portion and a methylase or demethylase, or an RNA(s) or DNA(s) coding therefor; and (3) a guide RNA(s) (gRNA(s)) comprising a sequence complementary to a DNA sequence within 1 kb of a desired site of methylation or demethylation, or a DNA(s) expressing the gRNA(s).

3 Claims, 9 Drawing Sheets

Specification includes a Sequence Listing.

(a)

(b)

SEQUENCE LISTING

<160> NUMBER OF SEQ ID NOS: 47

<210> SEQ ID NO 1
<211> LENGTH: 19
<212> TYPE: PRT
<213> ORGANISM: Saccharomyces cerevisiae

<400> SEQUENCE: 1

Glu Glu Leu Leu Ser Lys Asn Tyr His Leu Glu Asn Glu Val Ala Arg
1               5                   10                  15

Leu Lys Lys

<210> SEQ ID NO 2
<211> LENGTH: 5
<212> TYPE: PRT
<213> ORGANISM: Artificial Sequence
<220> FEATURE:
<223> OTHER INFORMATION: linker 5

<400> SEQUENCE: 2

Gly Ser Gly Ser Gly
1               5

<210> SEQ ID NO 3
<211> LENGTH: 22
<212> TYPE: PRT
<213> ORGANISM: Artificial Sequence
<220> FEATURE:
<223> OTHER INFORMATION: linker 22

<400> SEQUENCE: 3

Gly Ser Gly Ser Gly Gly Ser Gly Ser Gly Ser Gly Gly Ser Gly Ser
1               5                   10                  15

Gly Gly Ser Gly Ser Gly
            20

<210> SEQ ID NO 4
<211> LENGTH: 43
<212> TYPE: PRT
<213> ORGANISM: Artificial Sequence
<220> FEATURE:
<223> OTHER INFORMATION: linker 43

<400> SEQUENCE: 4

Gly Ser Gly Ser Gly Gly Ser Gly Ser Gly Gly Ser Gly Ser Gly Gly
1               5                   10                  15

Ser Gly Ser Gly Gly Ser Gly Gly Ser Gly Ser Gly Gly Ser Gly Ser
            20                  25                  30

Gly Gly Ser Gly Ser Gly Gly Ser Gly Ser Gly
            35                  40

<210> SEQ ID NO 5
<211> LENGTH: 22
<212> TYPE: PRT
<213> ORGANISM: Artificial Sequence
<220> FEATURE:
<223> OTHER INFORMATION: 2A peptide

<400> SEQUENCE: 5

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 6
<211> LENGTH: 11427
<212> TYPE: DNA
<213> ORGANISM: Artificial Sequence
<220> FEATURE:
<223> OTHER INFORMATION: pCAG-dCas9TET1CD

<400> SEQUENCE: 6
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggac tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catgggtcga ggtgagcccc acgttctgct tcactctccc catctccccc ccctccccac     420
ccccaatttt gtatttattt attttttaat tattttgtgc agcgatgggg gcggggggg      480 ggggggcgcg cgccaggcgg ggcggggcgg ggcgaggggc gggcggggc gaggcggaga     540

-continued

```
ggtgcggcgg cagccaatca gagcggcgcg ctccgaaagt ttccttttat ggcgaggcgg      600
cggcggcggc ggcccctataa aaagcgaagc gcgcggcggg cgggagtcgc tgcgttgcct     660
tcgccccgtg ccccgctccg cgccgcctcg cgccgcccgc cccggctctg actgaccgcg     720
ttactcccac aggtgagcgg gcgggacggc ccttctcctc cgggctgtaa ttagcgcttg     780
gtttaatgac ggctcgtttc ttttctgtgg ctgcgtgaaa gccttaaagg gctccgggag     840
ggccctttgt gcggggggga gcggctcggg gggtgcgtgc gtgtgtgtgt gcgtggggag     900
cgccgcgtgc ggcccgcgct gcccggcggc tgtgagcgct gcgggcgcgg cgcggggctt     960
tgtgcgctcc gcgtgtgcgc gagggagcg cggccggggg cggtgccccg cggtgcgggg     1020
gggctgcgag gggaacaaag gctgcgtgcg gggtgtgtgc gtggggggt gagcaggggg      1080 tgtgggcgcg gcggtcgggc tgtaaccccc ccctgcaccc ccctccccga gttgctgagc    1140
acggcccggc ttcgggtgcg gggctccgtg cggggcgtgg cgcggggctc gccgtgccgg    1200
gcggggggtg gcggcaggtg ggggtgccgg gcggggcggg gccgcctcgg gccggggagg    1260
gctcggggga ggggcgcggc ggccccggag cgccggcggc tgtcgaggcg cggcgagccg    1320
cagccattgc ctttatggt aatcgtgcga gagggcgcag ggacttcctt tgtcccaaat     1380
ctggcggagc cgaaatctgg gaggcgccgc cgcaccccct ctagcgggcg cgggcgaagc   1440
ggtgcggcgc cggcaggaag gaaatgggcg gggagggcct tcgtgcgtcg ccgcgccgcc   1500
gtccccttct ccatctccag cctcggggct gccgcagggg gacggctgcc ttcggggggg    1560
acggggcagg gcggggttcg gcttctggcg tgtgaccggc ggctctagag cctctgctaa    1620
ccatgttcat gccttcttct ttttcctaca gctcctgggc aacgtgctgg ttgttgtgct    1680
gtctcatcat tttggcaaag aattctgcag tcgacggtac catgtaccca tacgatgttc    1740
cagattacgc ttcgccgaag aaaaagcgca aggtcgaagc gtccgacaag aagtacagca    1800
tcggcctggc catcggcacc aactctgtgg gctgggccgt gatcaccgac gagtacaagg    1860
tgcccagcaa gaaattcaag gtgctgggca acaccgaccg gcacagcatc aagaagaacc    1920
tgatcggagc cctgctgttc gacagcggcg aaacagccga ggccaccggg ctgaagagaa    1980
ccgccagaag aagatacacc agacggaaga accggatctg ctatctgcaa gagatcttca    2040
gcaacgagat ggccaaggtg gacgacagct tcttccacag actggaagag tccttcctgg    2100
tggaagagga taagaagcac gagcggcacc ccatcttcgg caacatcgtg gacgaggtgg    2160
cctaccacga gaagtacccc accatctacc acctgagaaa gaaactggtg gacagcaccg    2220
acaaggccga cctgcggctg atctatctgg ccctggccca catgatcaag ttccggggcc    2280
acttcctgat cgagggcgac ctgaaccccg acaacagcga cgtggacaag ctgttcatcc    2340
agctggtgca gacctacaac cagctgttcg aggaaaaccc catcaacgcc agcggcgtgg    2400
acgccaaggc catcctgtct gccagactga gcaagagcag acggctggaa aatctgatcg    2460
cccagctgcc cggcgagaag aagaatggcc tgttcggcaa cctgattgcc ctgagcctgg    2520
gcctgacccc caacttcaag agcaacttcg acctggccga ggatgccaaa ctgcagctga    2580
gcaaggacac ctacgacgac gacctggaca acctgctggc ccagatcggc gaccagtacg    2640
ccgacctgtt tctggccgcc aagaacctgt ccgacgccat cctgctgagc gacatcctga    2700
gagtgaacac cgagatcacc aaggcccccc tgagcgcctc tatgatcaag agatacgacg    2760
agcaccacca ggacctgacc ctgctgaaag ctctcgtgcg gcagcagctg cctgagaagt    2820
acaaagagat tttcttcgac cagagcaaga acggctacgc cggctacatt gacggcggag    2880
```

```
ccagccagga agagttctac aagttcatca agcccatcct ggaaaagatg gacggcaccg      2940
aggaactgct cgtgaagctg aacagagagg acctgctgcg gaagcagcgg accttcgaca      3000
acggcagcat ccccaccag atccacctgg gagagctgca cgccattctg cggcggcagg       3060 aagatttttta cccattcctg aaggacaacc gggaaaagat cgagaagatc ctgaccttcc     3120
gcatccccta ctacgtgggc cctctggcca ggggaaacag cagattcgcc tggatgacca      3180
gaaagagcga ggaaaccatc accccctgga acttcgagga agtggtggac aagggcgctt      3240
ccgcccagag cttcatcgag cggatgacca acttcgataa gaacctgccc aacgagaagg      3300
tgctgcccaa gcacagcctg ctgtacgagt acttcaccgt gtataacgag ctgaccaaag      3360
tgaaatacgt gaccgaggga atgagaaagc ccgccttcct gagcggcgag cagaaaaagg      3420
ccatcgtgga cctgctgttc aagaccaacc ggaaagtgac cgtgaagcag ctgaaagagg      3480
actacttcaa gaaaatcgag tgcttcgact ccgtggaaat ctccggcgtg gaagatcggt      3540
tcaacgcctc cctgggcaca taccacgatc tgctgaaaat tatcaaggac aaggacttcc      3600
tggacaatga ggaaaacgag gacattctgg aagatatcgt gctgaccctg acactgtttg      3660
aggacagaga gatgatcgag gaacggctga aaacctatgc ccacctgttc gacgacaaag      3720
tgatgaagca gctgaagcgg cggagataca ccggctgggg caggctgagc cggaagctga      3780
tcaacggcat ccgggacaag cagtccggca agacaatcct ggatttcctg aagtccgacg      3840
gcttcgccaa cagaaacttc atgcagctga tccacgacga cagcctgacc tttaaagagg      3900
acatccagaa agcccaggtg tccggccagg gcgatagcct gcacgagcac attgccaatc      3960
tggccggcag ccccgccatt aagaagggca tcctgcagac agtgaaggtg gtggacgagc      4020
tcgtgaaagt gatgggccgg cacaagcccg agaacatcgt gatcgaaatg gccagagaga      4080
accagaccac ccagaaggga cagaagaaca gccgcgagag aatgaagcgg atcgaagagg      4140
gcatcaaaga gctgggcagc cagatcctga aagaacaccc cgtggaaaac acccagctgc      4200
agaacgagaa gctgtacctg tactacctgc agaatgggcg ggatatgtac gtggaccagg      4260
aactggacat caaccggctg tccgactacg atgtggacgc catcgtgcct cagagctttc      4320
tgaaggacga ctccatcgac aacaaggtgc tgaccagaag cgacaagaac cggggcaaga      4380
gcgacaacgt gcctccgaa gaggtcgtga agaagatgaa gaactactgg cggcagctgc       4440
tgaacgccaa gctgattacc cagagaaagt tcgacaatct gaccaaggcc gagagaggcg      4500
gcctgagcga actggataag gccggcttca tcaagagaca gctggtggaa acccggcaga      4560
tcacaaagca cgtggcacag atcctggact cccggatgaa cactaagtac gacgagaatg      4620
acaagctgat ccgggaagtg aaagtgatca ccctgaagtc caagctggtg tccgatttcc      4680
ggaaggattt ccagttttac aaagtgcgcg agatcaacaa ctaccaccac gcccacgacg      4740
cctacctgaa cgccgtcgtg ggaaccgccc tgatcaaaaa gtaccctaag ctggaaagcg      4800
agttcgtgta cggcgactac aaggtgtacg acgtgcggaa gatgatcgcc aagagcgagc      4860
aggaaatcgg caaggctacc gccaagtact tcttctacag caacatcatg aactttttca      4920
agaccgagat taccctggcc aacggcgaga tccggaagcg gcctctgatc gagacaaacg      4980
gcgaaaccgg ggagatcgtg tgggataagg gccgggattt tgccaccgtg cggaaagtgc      5040
tgagcatgcc ccaagtgaat atcgtgaaaa agaccgaggt gcagacaggc ggcttcagca      5100
aagagtctat cctgcccaag aggaacagcg ataagctgat cgccagaaag aaggactggg      5160
accctaagaa gtacggcggc ttcgacagcc ccaccgtggc ctattctgtg ctggtggtgg      5220
ccaaagtgga aaagggcaag tccaagaaac tgaagagtgt gaaagagctg ctggggatca      5280
```

```
ccatcatgga aagaagcagc ttcgagaaga atcccatcga ctttctggaa gccaagggct   5340
acaaagaagt gaaaaaggac ctgatcatca agctgcctaa gtactccctg ttcgagctgg   5400
aaaacggccg gaagagaatg ctggcctctg ccggcgaact gcagaaggga aacgaactgg   5460
ccctgccctc caaatatgtg aacttcctgt acctggccag ccactatgag aagctgaagg   5520
gctcccccga ggataatgag cagaaacagc tgtttgtgga acagcacaag cactacctgg   5580
acgagatcat cgagcagatc agcgagttct ccaagagagt gatcctggcc gacgctaatc   5640
tggacaaagt gctgtccgcc tacaacaagc accgggataa gcccatcaga gagcaggccg   5700
agaatatcat ccacctgttt accctgacca atctgggagc ccctgccgcc ttcaagtact   5760
ttgacaccac catcgaccgg aagaggtaca ccagcaccaa agaggtgctg gacgccaccc   5820
tgatccacca gagcatcacc ggcctgtacg agacacggat cgacctgtct cagctgggag   5880
gcgacagccc caagaagaag agaaaggtgg aggccagcgg tggcggagga tccgaactgc   5940
ccacctgcag ctgtcttgat cgagttatac aaaaagacaa aggcccatat tatacacacc   6000
ttggggcagg accaagtgtt gctgctgtca gggaaatcat ggagaatagg tatggtcaaa   6060
aaggaaacgc aataaggata gaaatagtag tgtacaccgg taagaaggg  aaaagctctc   6120 atgggtgtcc aattgctaag tgggttttaa gaagaagcag tgatgaagaa aaagttcttt   6180
gtttggtccg gcagcgtaca ggccaccact gtccaactgc tgtgatggtg gtgctcatca   6240
tggtgtggga tggcatccct cttccaatgg ccgaccggct atacacagag ctcacagaga   6300
atctaaagtc atacaatggg caccctaccg acagaagatg caccctcaat gaaaatcgta   6360
cctgtacatg tcaaggaatt gatccagaga cttgtggagc ttcattctct tttggctgtt   6420
catggagtat gtactttaat ggctgtaagt ttggtagaag cccaagcccc agaagattta   6480
gaattgatcc aagctctccc ttacatgaaa aaaccttga agataactta cagagtttgg   6540
ctacacgatt agctccaatt tataagcagt atgctccagt agcttaccaa atcaggtgg   6600 aatatgaaaa tgttgcccga gaatgtcggc ttggcagcaa ggaaggtcgt cccttctctg   6660
gggtcactgc ttgcctggac ttctgtgctc atccccacag ggacattcac aacatgaata   6720
atggaagcac tgtggtttgt accttaactc gagaagataa ccgctctttg ggtgttattc   6780
ctcaagatga gcagctccat gtgctacctc tttataagct ttcagacaca gatgagtttg   6840
gctccaagga aggaatggaa gccaagatca atctggggc catcgaggtc ctggcacccc   6900
gccgcaaaaa aagaacgtgt ttcactcagc ctgttccccg ttctggaaag aagagggctg   6960
cgatgatgac agaggttctt gcacataaga taagggcagt ggaaaagaaa cctattcccc   7020
gaatcaagcg gaagaataac tcaacaacaa caaacaacag taagccttcg tcactgccaa   7080
ccttagggag taacactgag accgtgcaac ctgaagtaaa agtgaaacc gaaccccatt   7140 ttatcttaaa aagttcagac aacactaaaa cttattcgct gatgccatcc gctcctcacc   7200
cagtgaaaga ggcatctcca ggcttctcct ggtccccgaa gactgcttca gccacaccag   7260
ctccactgaa gaatgacgca acagcctcat gcgggttttc agaaagaagc agcactcccc   7320
actgtacgat gccttcggga agactcagtg gtgccaatgc agctgctgct gatggccctg   7380
gcatttcaca gcttggcgaa gtggctcctc tccccaccct gtctgctcct gtgatggagc   7440
ccctcattaa ttctgagcct tccactggtg tgactgagcc gctaacgcct catcagccaa   7500
accaccagcc ctccttcctc acctctcctc aagaccttgc ctcttctcca atggaagaag   7560
atgagcagca ttctgaagca gatgagcctc catcagacga accctatctg atgacccc    7620
```

```
tgtcacctgc tgaggagaaa ttgccccaca ttgatgagta ttggtcagac agtgagcaca    7680
tcttttggga tgcaaatatt ggtggggtgg ccatcgcacc tgctcacggc tcggttttga    7740
ttgagtgtgc ccggcgagag ctgcacgcta ccactcctgt tgagcacccc aaccgtaatc    7800
atccaacccg cctctcccTt gtcttttacc agcacaaaaa cctaaataag ccccaacatg    7860
gttttgaact aaacaagatt aagtttgagg ctaaagaagc taagaataag aaaatgaagg    7920
cctcagagca aaaagaccag gcagctaatg aaggtccaga acagtcctct gaagtaaatg    7980
aattgaacca aattccttct cataaagcat taacattaac ccatgacaat gttgtcaccg    8040
tgtcccctta tgctctcaca cacgttgcgg ggccctataa ccattgggtc tgagcggccg    8100
cgactctaga tcataatcag ccataccaca tttgtagagg ttttacttgc tttaaaaaac    8160
ctcccacacc tccccctgaa cctgaaacat aaaatgaatg caattgttgt tgttaacttg    8220
tttattgcag cttataatgg ttacaaataa agcaatagca tcacaaattt cacaaataaa    8280
gcatttttTt cactgcattc tagttgtggt ttgtccaaac tcatcaatgt atcttaaggc    8340
gtaaattgta agcgttaata ttttgttaaa attcgcgtta aattttTgtt aaatcagctc    8400
atTttttaac caataggccg aaatcggcaa aatcccttat aaatcaaaag aatagaccga    8460
gatagggttg agtgttgttc cagtttggaa caagagtcca ctattaaaga acgtggactc    8520
caacgtcaaa gggcgaaaaa ccgtctatca gggcgatggc ccactacgtg aaccatcacc    8580
ctaatcaagt ttttTggggt cgaggtgccg taaagcacta atcggaacc ctaaagggag    8640 ccccgattt agagcttgac ggggaaagcc ggcgaacgtg gcgagaaagg aagggaagaa    8700
agcgaaagga gcgggcgcta gggcgctggc aagtgtagcg gtcacgctgc gcgtaaccac    8760
cacacccgcc gcgcttaatg cgccgctaca gggcgcgtca ggtggcactT tcggggaaa    8820 tgtgcgcgga accctatTt gTttatTttt ctaaatacat tcaaatatgt atccgctcat    8880
gagacaataa ccctgataaa tgcttcaata atattgaaaa aggaagagtc ctgaggcgga    8940
aagaaccagc tgtggaatgt gtgtcagtta gggtgtggaa agtccccagg ctccccagca    9000
ggcagaagta tgcaaagcat gcatctcaat tagtcagcaa ccaggtgtgg aaagtcccca    9060
ggctccccag caggcagaag tatgcaaagc atgcatctca attagtcagc aaccatagtc    9120
ccgcccctaa ctccgcccat cccgcccta actccgccca gttccgccca ttctccgccc    9180
catggctgac taatttttTt tatttatgca gaggccgagg ccgcctcggc ctctgagcta    9240
ttccagaagt agtgaggagg cttttTtgga ggcctaggct tttgcaaaga tcgatcaaga    9300
gacaggatga ggatcgtttc gcatgattga acaagatgga ttgcacgcag gttctccggc    9360
cgcttgggtg gagaggctat tcggctatga ctgggcacaa cagacaatcg gctgctctga    9420
tgccgccgtg ttccggctgt cagcgcaggg gcgcccggtt ctttTtgtca agaccgacct    9480
gtccggtgcc ctgaatgaac tgcaagacga ggcagcgcgg ctatcgtggc tggccacgac    9540
gggcgttcct tgcgcagctg tgctcgacgt tgtcactgaa gcgggaaggg actggctgct    9600
attgggcgaa gtgccggggc aggatctcct gtcatctcac cttgctcctg ccgagaaagt    9660
atccatcatg gctgatgcaa tgcggcggct gcatacgctt gatccggcta cctgcccatt    9720
cgaccaccaa gcgaaacatc gcatcgagcg agcacgtact cggatggaag ccggtcttgt    9780
cgatcaggat gatctggacg aagagcatca ggggctcgcg ccagccgaac tgttcgccag    9840
gctcaaggcg agcatgcccg acggcgagga tctcgtcgtg acccatggcg atgcctgctt    9900
gccgaatatc atggtggaaa atggccgctt ttctggattc atcgactgtg gccggctggg    9960
tgtggcggac cgctatcagg acatagcgtt ggctacccgt gatattgctg aagagcttgg   10020
```

```
cggcgaatgg gctgaccgct tcctcgtgct ttacggtatc gccgctcccg attcgcagcg    10080
catcgccttc tatcgccttc ttgacgagtt cttctgagcg ggactctggg gttcgaaatg    10140
accgaccaag cgacgcccaa cctgccatca cgagatttcg attccaccgc cgccttctat    10200
gaaaggttgg gcttcggaat cgttttccgg gacgccggct ggatgatcct ccagcgcggg    10260
gatctcatgc tggagttctt cgcccaccct aggggaggc taactgaaac acggaaggag     10320
acaataccgg aaggaacccg cgctatgacg gcaataaaaa gacagaataa aacgcacggt    10380
gttgggtcgt ttgttcataa acgcggggtt cggtcccagg gctggcactc tgtcgatacc    10440
ccaccgagac cccattgggg ccaatacgcc cgcgtttctt ccttttcccc acccacccc    10500
ccaagttcgg gtgaaggccc agggctcgca gccaacgtcg gggcggcagg ccctgccata    10560
gcctcaggtt actcatatat actttagatt gatttaaaac ttcattttta atttaaaagg    10620
atctaggtga agatcctttt tgataatctc atgaccaaaa tcccttaacg tgagttttcg    10680
ttccactgag cgtcagaccc cgtagaaaag atcaaaggat cttcttgaga tcctttttttt   10740
ctgcgcgtaa tctgctgctt gcaaacaaaa aaaccaccgc taccagcggt ggtttgtttg    10800
ccggatcaag agctaccaac tctttttccg aaggtaactg gcttcagcag agcgcagata    10860
ccaaatactg tccttctagt gtagccgtag ttaggccacc acttcaagaa ctctgtagca    10920
ccgcctacat acctcgctct gctaatcctg ttaccagtgg ctgctgccag tggcgataag    10980
tcgtgtctta ccgggttgga ctcaagacga tagttaccgg ataaggcgca gcggtcgggc    11040
tgaacggggg gttcgtgcac acagcccagc ttggagcgaa cgacctacac cgaactgaga    11100
tacctacagc gtgagctatg agaaagcgcc acgcttcccg aagggagaaa ggcggacagg    11160
tatccggtaa gcggcagggt cggaacagga gagcgcacga gggagcttcc agggggaaac    11220
gcctggtatc tttatagtcc tgtcgggttt cgccacctct gacttgagcg tcgatttttg    11280
tgatgctcgt caggggggcg gagcctatgg aaaaacgcca gcaacgcggc cttttacgg    11340
ttcctggcct tttgctggcc ttttgctcac atgttctttc ctgcgttatc ccctgattct    11400
gtggataacc gtattaccgc catgcat                                        11427
```

<210> SEQ ID NO 7
<211> LENGTH: 10188
<212> TYPE: DNA
<213> ORGANISM: Artificial Sequence
<220> FEATURE:
<223> OTHER INFORMATION: pCAG-dCas9-10xGCN4_v4

<400> SEQUENCE: 7

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggac tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtcga ggtgagcccc acgttctgct tcactctccc catctccccc cctccccac     420
ccccaatttt gtatttattt attttttaat tattttgtgc agcgatgggg gcggggggg     480
ggggggcgcg cgccaggcgg ggcggggcgg ggcgagggggc ggggcgggc gaggcggaga    540
ggtgcggcgg cagccaatca gagcggcgcg ctccgaaagt ttcctttat ggcgaggcgg     600
```

```
cggcggcggc ggccctataa aaagcgaagc gcgcggcggg cgggagtcgc tgcgttgcct    660
tcgccccgtg ccccgctccg cgccgcctcg cgccgcccgc cccggctctg actgaccgcg    720
ttactcccac aggtgagcgg gcgggacggc ccttctcctc cgggctgtaa ttagcgcttg    780
gtttaatgac ggctcgtttc ttttctgtgg ctgcgtgaaa gccttaaagg gctccgggag    840
ggccctttgt gcggggggga gcggctcggg gggtgcgtgc gtgtgtgtgt gcgtggggag    900
cgccgcgtgc ggcccgcgct gccggcggc tgtgagcgct gcgggcgcgg cgcggggctt     960
tgtgcgctcc gcgtgtgcgc gaggggagcg cggccggggg cggtgccccg cggtgcgggg   1020
gggctgcgag gggaacaaag gctgcgtgcg gggtgtgtgc gtggggggt gagcaggggg    1080 tgtgggcgcg gcggtcgggc tgtaaccccc ccctgcaccc ccctccccga gttgctgagc   1140
acggcccggc ttcgggtgcg gggctccgtg cggggcgtgg cgcggggctc gccgtgccgg   1200 gcgggggtg gcggcaggtg ggggtgccgg gcggggcggg gccgcctcgg gccggggagg    1260
gctcggggga ggggcgcggc ggccccggag cgccggcggc tgtcgaggcg cggcgagccg   1320
cagccattgc ctttatggt aatcgtgcga gagggcgcag ggacttcctt tgtcccaaat    1380
ctggcggagc cgaaatctgg gaggcgccgc cgcaccccct ctagcgggcg cgggcgaagc   1440
ggtgcggcgc cggcaggaag gaaatgggcg gggagggcct tcgtgcgtcg ccgcgccgcc   1500
gtccccttct ccatctccag cctcggggct gccgcagggg gacggctgcc ttcgggggg    1560 acggggcagg gcggggttcg gcttctggcg tgtgaccggc ggctctagag cctctgctaa   1620
ccatgttcat gccttcttct ttttcctaca gctcctgggc aacgtgctgg ttgttgtgct   1680
gtctcatcat tttggcaaag aattctgcag tcgacggtac cgcgggcccc ctaggctacg   1740
cgcgccacca tgcccaagaa gaagcgcaag gtgggacgcg tctgcaggat atcaagcttg   1800
cggtaccgcg ggcccgggat cgccaccatg gacaagaagt acagcatcgg cctggccatc   1860
ggcaccaact ctgtgggctg gccgtgatc accgacgagt acaaggtgcc cagcaagaaa    1920
ttcaaggtgc tgggcaacac cgaccggcac agcatcaaga gaacctgat cggcgccctg    1980 ctgttcgaca gcggagaaac agccgaggcc accggctga agagaaccgc cagaagaaga    2040 taccagac ggaagaaccg gatctgctat ctgcaagaga tcttcagcaa cgagatggcc     2100
aaggtggacg acagcttctt ccacagactg gaagagtcct tcctggtgga agaggataag   2160
aagcacgagc ggcaccccat cttcggcaac atcgtggacg aggtggccta ccacgagaag   2220
taccccacca tctaccacct gagaaagaaa ctggtggaca gcaccgacaa ggccgacctg   2280
cggctgatct atctggccct ggcccacatg atcaagttcc ggggccactt cctgatcgag   2340
ggcgacctga accccgacaa cagcgacgtg gacaagctgt tcatccagct ggtgcagacc   2400
tacaaccagc tgttcgagga aaaccccatc aacgccagcg gcgtggacgc caaggccatc   2460
ctgtctgcca gactgagcaa gagcagacgg ctggaaaatc tgatcgccca gctgcccggc   2520
gagaagaaga atggcctgtt cggcaacctg attgccctga gcctgggcct gacccccaac   2580
ttcaagagca acttcgacct ggccgaggat gccaaactgc agctgagcaa ggacacctac   2640
gacgacgacc tggacaacct gctggcccag atcggcgacc agtacgccga cctgtttctg   2700
gccgccaaga acctgtccga cgccatcctg ctgagcgaca tcctgagagt gaacaccgag   2760
atcaccaagg ccccctgag cgcctctatg atcaagagat acgacgagca ccaccaggac   2820 ctgacccctgc tgaaagctct cgtgcggcag cagctgcctg agaagtacaa agagattttc   2880
ttcgaccaga gcaagaacgg ctacgccggc tacatcgatg gcggagccag ccaggaagag   2940
ttctacaagt tcatcaagcc catcctggaa aagatggacg gcaccgagga actgctcgtg   3000
```

```
aagctgaaca gagaggacct gctgcggaag cagcggacct tcgacaacgg cagcatcccc    3060
caccagatcc acctgggaga gctgcacgcc attctgcggc ggcaggaaga ttttacccca    3120
ttcctgaagg acaaccggga aaagatcgag aagatcctga ccttccgcat ccctactac    3180 gtgggccctc tggccagggg aaacagcaga ttcgcctgga tgaccagaaa gagcgaggaa    3240
accatcaccc cctggaactt cgaggaagtg gtggacaagg gcgccagcgc ccagagcttc    3300
atcgagcgga tgaccaactt cgataagaac ctgcccaacg agaaggtgct gcccaagcac    3360
agcctgctgt acgagtactt caccgtgtac aacgagctga ccaaagtgaa atacgtgacc    3420
gagggaatga gaaagcccgc cttcctgagc ggcgagcaga aaaaagccat cgtggacctg    3480
ctgttcaaga ccaaccggaa agtgaccgtg aagcagctga agaggacta cttcaagaaa    3540 atcgagtgct tcgactccgt ggaaatctcc ggcgtggaag atcggttcaa cgcctccctg    3600
ggcacatacc acgatctgct gaaaattatc aaggacaagg acttcctgga caatgaggaa    3660
aacgaggaca ttctggaaga tatcgtgctg accctgacac tgtttgagga cagagagatg    3720
atcgaggaac ggctgaaaac ctatgcccac ctgttcgacg acaaagtgat gaagcagctg    3780
aagcggcgga gatacaccgg ctggggcagg ctgagccgga agctgatcaa cggcatccgg    3840
gacaagcagt ccggcaagac aatcctggat ttcctgaagt ccgacggctt cgccaacaga    3900
aacttcatgc agctgatcca cgacgacagc ctgaccttta agaggacat ccagaaagcc    3960 caggtgtccg gccagggcga tagcctgcac gagcacattg ccaatctggc cggcagcccc    4020
gccattaaga agggcatcct gcagacagtg aaggtggtgg acgagctcgt gaaagtgatg    4080
ggccggcaca agcccgagaa catcgtgatc gaaatggcca gagagaacca gaccacccag    4140
aagggacaga gaacagccg cgagagaatg aagcggatcg aagagggcat caaagagctg    4200
ggcagccaga tcctgaaaga acaccccgtg gaaaacaccc agctgcagaa cgagaagctg    4260
tacctgtact acctgcagaa tgggcgggat atgtacgtgg accaggaact ggacatcaac    4320
cggctgtccg actacgatgt ggacgctatc gtgcctcaga gctttctgaa ggacgactcc    4380
atcgataaca aagtgctgac tcggagcgac aagaaccggg gcaagagcga caacgtgccc    4440
tccgaagagg tcgtgaagaa gatgaagaac tactggcgcc agctgctgaa tgccaagctg    4500
attacccaga ggaagttcga caatctgacc aaggccgaga gaggcggcct gagcgaactg    4560
gataaggccg gcttcatcaa gagacagctg gtggaaaccc ggcagatcac aaagcacgtg    4620
gcacagatcc tggactcccg gatgaacact aagtacgacg agaacgacaa actgatccgg    4680
gaagtgaaag tgatcacccct gaagtccaag ctggtgtccg atttccggaa ggatttccag    4740
ttttacaaag tgcgcgagat caacaactac caccacgccc acgacgccta cctgaacgcc    4800
gtcgtgggaa ccgccctgat caaaaagtac cctaagctgg aaagcgagtt cgtgtacggc    4860
gactacaagg tgtacgacgt gcggaagatg atcgccaaga gcgagcagga aatcggcaag    4920
gctaccgcca gtacttctt ctacagcaac atcatgaact ttttcaagac cgagattacc    4980
ctggccaacg gcgagatccg gaagcggcct ctgatcgaga caaacggcga aacaggcgag    5040
atcgtgtggg ataagggccg ggactttgcc accgtgcgga aagtgctgtc tatgccccaa    5100
gtgaatatcg tgaaaaagac cgaggtgcag acaggcggct tcagcaaaga gtctatcctg    5160
cccaagagga acagcgacaa gctgatcgcc agaaagaagg actgggaccc taagaagtac    5220
ggcggcttcg acagcccac cgtggcctat tctgtgctgg tggtggccaa agtggaaaag    5280
ggcaagtcca agaaactgaa gagtgtgaaa gagctgctgg gatcaccat catggaaaga    5340
```

```
agcagcttcg agaagaatcc catcgacttt ctggaagcca agggctacaa agaagtgaaa      5400
aaggacctga tcatcaagct gcctaagtac tccctgttcg agctggaaaa cggccggaag      5460
agaatgctgg cctctgccgg cgaactgcag aagggaaacg aactggccct gccctccaaa      5520
tatgtgaact tcctgtacct ggccagccac tatgagaagc tgaagggctc ccccgaggat      5580
aatgagcaga aacagctgtt tgtggaacag cacaaacact acctggacga gatcatcgag      5640
cagatcagcg agttctccaa gagagtgatc ctggccgacg ctaatctgga caaggtgctg      5700
agcgcctaca acaagcacag agacaagcct atcagagagc aggccgagaa tatcatccac      5760
ctgtttaccc tgaccaatct gggagcccct gccgccttca gtactttga caccaccatc      5820 gaccggaaga ggtacaccag caccaaagag gtgctggacg ccaccctgat ccaccagagc      5880
atcaccggcc tgtacgagac acggatcgac ctgtctcagc tgggaggcga cgcctatccc      5940
tatgacgtgc ccgattatgc cagcctgggc agcggctccc ccaagaaaaa acgcaaggtg      6000
gaagatccta agaaaaagcg gaaagtggac ggcattggta gtgggagcaa cggcagcagc      6060
ggatccaacg gtccgactga cgccgcggaa gaagaacttt tgagcaagaa ttatcatctt      6120
gagaacgaag tggctcgtct taagaaaggt tctggcagtg agaagaact gctttcaaag      6180 aattaccacc tggaaaatga ggtagctaga ctgaaaaagg ggagcggaag tggggaggag      6240
ttgctgagca aaaattatca tttggagaac gaagtagcac gactaaagaa agggtccgga      6300
tcgggtgagg agttactctc gaaaaattat catctcgaaa acgaagtggc tcggctaaaa      6360
aagggcagtg gttctggaga gagctatta tctaaaaact accacctcga aaatgaggtg      6420
gcacgcttaa aaagggaag tggcagtggt gaagagctac tatccaagaa ttatcatctt      6480
gagaacgagg tagcgcgttt gaagaagggt tccggctcag gagaggaact gctctcgaag      6540
aactatcatc ttgaaaatga ggtcgctcga ttaaaaagg gatcgggcag tggtgaggaa      6600
ctactttcaa agaattacca cctcgaaaac gaagtagctc gattaaagaa aggttcaggg      6660
tcgggtgaag aattactgag taaaaattat catctcgaaa atgaggtagc gagactaaaa      6720
aaggggagtg gttctggcga ggaattgcta tcgaaaaatt atcatcttga gaacgaagtt      6780
gctaggctca aaaagggctc aggctcaggc accgcgtaa acataggtgg tggaaccggt      6840
ccgatggatc tacagcggcc gcgactctag atcataatca gccataccac atttgtagag      6900
gttttacttg cttaaaaaa cctcccacac ctccccctga acctgaaaca taaaatgaat      6960
gcaattgttg ttgttaactt gtttattgca gcttataatg gttacaaata aagcaatagc      7020
atcacaaatt tcacaaataa agcatttttt tcactgcatt ctagttgtgg tttgtccaaa      7080
ctcatcaatg tatcttaagg cgtaaattgt aagcgttaat attttgttaa aattcgcgtt      7140 aaattttgt taaatcagct cattttttaa ccaataggcc gaaatcggca aaatccctta      7200
taaatcaaaa gaatagaccg agatagggtt gagtgttgtt ccagtttgga acaagagtcc      7260
actattaaag aacgtggact ccaacgtcaa agggcgaaaa accgtctatc agggcgatgg      7320
cccactacgt gaaccatcac cctaatcaag ttttttgggg tcgaggtgcc gtaaagcact      7380
aaatcggaac cctaaaggga gcccccgatt tagagcttga cggggaaagc cggcgaacgt      7440
ggcgagaaag gaagggaaga agcgaaagg agcgggcgct agggcgctgg caagtgtagc      7500
ggtcacgctg cgcgtaacca ccacacccgc cgcgcttaat gcgccgctac agggcgcgtc      7560
aggtggcact tttcgggaa atgtgcgcgg aaccctatt tgtttatttt tctaaataca      7620
ttcaaatatg tatccgctca tgagacaata accctgataa atgcttcaat aatattgaaa      7680
aaggaagagt cctgaggcgg aaagaaccag ctgtggaatg tgtgtcagtt agggtgtgga      7740
```

```
aagtccccag gctccccagc aggcagaagt atgcaaagca tgcatctcaa ttagtcagca    7800
accaggtgtg gaaagtcccc aggctcccca gcaggcagaa gtatgcaaag catgcatctc    7860
aattagtcag caaccatagt cccgcccta actccgccca tcccgcccct aactccgccc     7920
agttccgccc attctccgcc ccatggctga ctaattttt ttatttatgc agaggccgag     7980
gccgcctcgg cctctgagct attccagaag tagtgaggag gcttttttgg aggcctaggc    8040
ttttgcaaag atcgatcaag agacaggatg aggatcgttt cgcatgattg aacaagatgg     8100
attgcacgca ggttctccgg ccgcttgggt ggagaggcta ttcggctatg actgggcaca    8160
acagacaatc ggctgctctg atgccgccgt gttccggctg tcagcgcagg gcgcccggt     8220 tcttttgtc aagaccgacc tgtccggtgc cctgaatgaa ctgcaagacg aggcagcgcg     8280
gctatcgtgg ctggccacga cgggcgttcc ttgcgcagct gtgctcgacg ttgtcactga    8340
agcgggaagg gactggctgc tattgggcga agtgccgggg caggatctcc tgtcatctca    8400
ccttgctcct gccgagaaag tatccatcat ggctgatgca atgcggcggc tgcatacgct    8460
tgatccggct acctgcccat tcgaccacca agcgaaacat cgcatcgagc gagcacgtac    8520
tcggatggaa gccggtcttg tcgatcagga tgatctggac gaagagcatc aggggctcgc    8580
gccagccgaa ctgttcgcca ggctcaaggc gagcatgccc gacggcgagg atctcgtcgt    8640
gacccatggc gatgcctgct tgccgaatat catggtggaa aatggccgct tttctggatt    8700
catcgactgt ggccggctgg gtgtggcgga ccgctatcag gacatagcgt tggctacccg    8760
tgatattgct gaagagcttg gcggcgaatg ggctgaccgc ttcctcgtgc tttacggtat    8820
cgccgctccc gattcgcagc gcatcgcctt ctatcgcctt cttgacgagt tcttctgagc    8880
gggactctgg ggttcgaaat gaccgaccaa gcgacgccca acctgccatc acgagatttc    8940
gattccaccg ccgccttcta tgaaaggttg ggcttcggaa tcgttttccg ggacgccggc    9000
tggatgatcc tccagcgcgg ggatctcatg ctggagttct cgcccaccc taggggagg     9060 ctaactgaaa cacggaagga gacaataccg gaaggaaccc gcgctatgac ggcaataaaa    9120
agacagaata aaacgcacgg tgttgggtcg tttgttcata aacgcggggt tcggtcccag    9180
ggctggcact ctgtcgatac cccaccgaga ccccattggg gccaatacgc ccgcgtttct    9240 tcctttccc caccccaccc ccaagttcg ggtgaaggcc cagggctcgc agccaacgtc      9300
ggggcggcag gccctgccat agcctcaggt tactcatata tactttagat tgatttaaaa    9360 cttcatttt aatttaaaag gatctaggtg aagatccttt ttgataatct catgaccaaa     9420
atcccttaac gtgagttttc gttccactga gcgtcagacc ccgtagaaaa gatcaaagga    9480
tcttcttgag atcctttttt tctgcgcgta atctgctgct tgcaaacaaa aaaaccaccg    9540
ctaccagcgg tggtttgttt gccggatcaa gagctaccaa ctcttttcc gaaggtaact     9600 ggcttcagca gagcgcagat accaaatact gtccttctag tgtagccgta gttaggccac    9660
cacttcaaga actctgtagc accgcctaca tacctcgctc tgctaatcct gttaccagtg    9720
gctgctgcca gtggcgataa gtcgtgtctt accgggttgg actcaagacg atagttaccg    9780
gataaggcgc agcggtcggg ctgaacgggg ggttcgtgca cacagcccag cttggagcga    9840
acgacctaca ccgaactgag atacctacag cgtgagctat gagaaagcgc cacgcttccc    9900
gaagggagaa aggcggacag gtatccggta agcggcaggg tcggaacagg agagcgcacg    9960
agggagcttc caggggggaaa cgcctggtat ctttatagtc ctgtcgggtt cgccacctc   10020 tgacttgagc gtcgattttt gtgatgctcg tcagggggc ggagcctatg gaaaaacgcc    10080
```

```
agcaacgcgg ccttttttacg gttcctggcc ttttgctggc cttttgctca catgttcttt    10140
cctgcgttat cccctgattc tgtggataac cgtattaccg ccatgcat              10188

<210> SEQ ID NO 8
<211> LENGTH: 8829
<212> TYPE: DNA
<213> ORGANISM: Artificial Sequence
<220> FEATURE:
<223> OTHER INFORMATION: pCAG-scFvGCN4sfGFPTET1CD

<400> SEQUENCE: 8
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggac tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catgggtcga ggtgagcccc acgttctgct tcactctccc catctccccc cctccccac      420 ccccaatttt gtatttattt attttttaat tattttgtgc agcgatgggg gcggggggg      480 ggggggcgcg cgccaggcgg ggcggggcgg ggcgaggggc ggggcgggc gaggcggaga     540 ggtgcggcgg cagccaatca gagcggcgcg ctccgaaagt ttcctttat ggcgaggcgg     600 cggcggcggc ggccctataa aaagcgaagc gcgcggcggg cggagtcgc tgcgttgcct     660 tcgcccgtg ccccgctccg cgccgcctcg cgccgcccgc cccggctctg actgaccgcg     720
ttactcccac aggtgagcgg gcgggacggc ccttctcctc cgggctgtaa ttagcgcttg     780
gtttaatgac ggctcgtttc ttttctgtgg ctgcgtgaaa gccttaaagg gctccgggag     840 ggcccttgt gcgggggggga gcggctcggg gggtgcgtgc gtgtgtgtgt gcgtggggag     900
cgccgcgtgc ggccccgcgct gcccggccgg tgtgagcgct gcgggcgcgg cgcgggggctt     960 tgtgcgctcc gcgtgtgcgc gaggggagcg cggccggggg cggtgccccg cggtgcgggg    1020
gggctgcgag gggaacaaag gctgcgtgcg gggtgtgtgc gtggggggggt gagcagggg    1080 tgtgggcgcg gcggtcgggc tgtaaccccc ccctgcaccc ccctccccga gttgctgagc    1140
acggcccggc ttcgggtgcg gggctccgtc cggggcgtgg gcgcggggctc gccgtgccgg    1200 gcggggggtg gcggcaggtg ggggtgccgg gcggggcggg gccgcctcgg gccggggagg    1260
gctcggggga ggggcgcggc ggccccggag cgccggcggc tgtcgaggcg cggcgagccg    1320
cagccattgc ctttttatggt aatcgtgcga gagggcgcag ggacttcctt tgtcccaaat    1380
ctggcggagc cgaaatctgg gaggcgccgc cgcacccccct ctagcgggcg cgggcgaagc    1440
ggtgcggcgc cggcaggaag gaaatgggcg gggagggcct tcgtgcgtcg ccgcgccgcc    1500
gtccccttct ccatctccag cctcggggct gccgcagggg gacggctgcc ttcgggggg    1560 acggggcagg gcggggttcg gcttctgcg tgtgaccggc ggctctagag cctctgctaa    1620
ccatgttcat gccttcttct ttttcctaca gctcctgggc aacgtgctgg ttgttgtgct    1680
gtctcatcat tttggcaaag aattctgcag tcgacggtac catgggcccc gacatcgtga    1740
tgacccagag ccccagcagc ctgagcgcca gcgtgggcga ccgcgtgacc atcacctgcc    1800
gcagcagcac cggcgccgtg accaccagca actacgccag ctgggtgcag agaagcccg    1860 gcaagctgtt caagggcctg atcggcgcca ccaacaaccg cgcccccggc gtgcccagcc    1920
gcttcagcgg cagcctgatc ggcgacaagg ccaccctgac catcagcagc ctgcagcccg    1980
```

-continued

```
aggacttcgc cacctacttc tgcgccctgt ggtacagcaa ccactgggtg ttcggccagg    2040
gcaccaaggt ggagctgaag cgcggcggcg gcggcagcgg cggcggcggc agcggcggcg    2100
gcggcagcag cggcggcggc agcgaggtga agctgctgga gagcggcggc ggcctggtgc    2160
agcccggcgg cagcctgaag ctgagctgcg ccgtgagcgg cttcagcctg accgactacg    2220
gcgtgaactg ggtgcgccag gcccccggcc gcggcctgga gtggatcggc gtgatctggg    2280
gcgacggcat caccgactac aacagcgccc tgaaggaccg cttcatcatc agcaaggaca    2340
acggcaagaa caccgtgtac ctgcagatga gcaaggtgcg cagcgacgac accgccctgt    2400
actactgcgt gaccggcctg ttcgactact ggggccaggg caccctggtg accgtgagca    2460
gctacccata cgatgttcca gattacgctg gtggaggcgg aggttctggg ggaggaggta    2520
gtggcggtgg tggttcagga ggcggcggaa gcttggatcc aggtgaggt ggaagcggta    2580 gcaaaggaga agaactttc actggagttg tcccaattct tgttgaatta gatggtgatg    2640
ttaatgggca caaatttct gtccgtggag agggtgaagg tgatgctaca aacgaaaaac    2700
tcacccttaa atttatttgc actactggaa aactacctgt tccgtggcca cacttgtca    2760 ctactctgac ctatggtgtt caatgctttt cccgttatcc ggatcacatg aaacggcatg    2820 acttttcaa gagtgccatg cccgaaggtt atgtacagga acgcactata tctttcaaag    2880
atgacgggac ctacaagacg cgtgctgaag tcaagtttga aggtgatacc cttgttaatc    2940
gtatcgagtt aaagggtatt gattttaaag aagatggaaa cattcttgga cacaaactcg    3000
agtacaactt taactcacac aatgtataca tcacggcaga caaacaaaag aatggaatca    3060
aagctaactt caaaattcgc cacaacgttg aagatggttc cgttcaacta gcagaccatt    3120
atcaacaaaa tactccaatt ggcgatggcc ctgtcctttt accagacaac cattacctgt    3180
cgacacaatc tgtcctttcg aaagatccca acgaaaagcg tgaccacatg gtccttcttg    3240
agtttgtaac tgctgctggg attacacatg gcatggatga gctctacaaa ggtgaggtc    3300 ggaccggtgg cggtggcgga ggggctagca gatccgaact gcccacctgc agctgtcttg    3360
atcgagttat acaaaaagac aaaggcccat attatacaca ccttgggggca ggaccaagtg    3420 ttgctgctgt cagggaaatc atggagaata ggtatggtca aaaaggaaac gcaataagga    3480
tagaaatagt agtgtacacc ggtaaagaag ggaaaagctc tcatgggtgt ccaattgcta    3540
agtgggtttt aagaagaagc agtgatgaag aaaaagttct tgtttggtc cggcagcgta    3600 caggccacca ctgtccaact gctgtgatgg tggtgctcat catggtgtgg gatggcatcc    3660
ctcttccaat ggccgaccgg ctatacacag agctcacaga gaatctaaag tcatacaatg    3720
ggcaccctac cgacagaaga tgcaccctca atgaaaatcg tacctgtaca tgtcaaggaa    3780
ttgatccaga gacttgtgga gcttcattct cttttggctg ttcatggagt atgtactta    3840 atggctgtaa gtttggtaga agcccaagcc ccagaagatt tagaattgat ccaagctctc    3900
ccttacatga aaaaaacctt gaagataact tacagagtt ggctacacga ttagctccaa    3960
tttataagca gtatgctcca gtagcttacc aaaatcaggt ggaatatgaa atgttgccc    4020 gagaatgtcg gcttggcagc aaggaaggtc gtcccttctc tgggtcact gcttgcctgg    4080 acttctgtgc tcatccccac agggacattc acaacatgaa taatgaaagc actgtggttt    4140
gtaccttaac tcgagaagat aaccgctctt gggtgttat tcctcaagat gagcagctcc    4200
atgtgctacc tcttttataag ctttcagaca cagatgagtt tggctccaag gaaggaatgg    4260
aagccaagat caaatctggg gccatcgagg tcctggcacc ccgccgcaaa aaagaacgt    4320
```

```
gtttcactca gcctgttccc cgttctggaa agaagagggc tgcgatgatg acagaggttc    4380
ttgcacataa gataagggca gtggaaaaga aacctattcc ccgaatcaag cggaagaata    4440
actcaacaac aacaaacaac agtaagcctt cgtcactgcc aaccttaggg agtaacactg    4500
agaccgtgca acctgaagta aaaagtgaaa ccgaacccca ttttatctta aaaagttcag    4560
acaacactaa aacttattcg ctgatgccat ccgctcctca cccagtgaaa gaggcatctc    4620
caggcttctc ctggtccccg aagactgctt cagccacacc agctccactg aagaatgacg    4680
caacagcctc atgcgggttt tcagaaagaa gcagcactcc ccactgtacg atgccttcgg    4740
gaagactcag tggtgccaat gcagctgctg ctgatggccc tggcatttca cagcttggcg    4800
aagtggctcc tctccccacc ctgtctgctc ctgtgatgga gcccctcatt aattctgagc    4860
cttccactgg tgtgactgag ccgctaacgc ctcatcagcc aaaccaccag ccctccttcc    4920
tcacctctcc tcaagacctt gcctcttctc caatggaaga agatgagcag cattctgaag    4980
cagatgagcc tccatcagac gaaccccctat ctgatgaccc cctgtcacct gctgaggaga    5040
aattgcccca cattgatgag tattggtcag acagtgagca catcttttg gatgcaaata    5100 ttggtggggt ggccatcgca cctgctcacg gctcggtttt gattgagtgt gcccggcgag    5160
agctgcacgc taccactcct gttgagcacc ccaaccgtaa tcatccaacc cgcctctccc    5220
ttgtctttta ccagcacaaa aacctaaata gccccaaca tggttttgaa ctaaacaaga    5280
ttaagtttga ggctaaagaa gctaagaata agaaaatgaa ggcctcagag caaaaagacc    5340
aggcagctaa tgaaggtcca gaacagtcct ctgaagtaaa tgaattgaac caaattcctt    5400
ctcataaagc attaacatta acccatgaca atgttgtcac cgtgtcccct tatgctctca    5460
cacacgttgc ggggccctat aaccattggg tctgagcggc cgcgactcta gatcataatc    5520
agccatacca catttgtaga ggttttactt gctttaaaaa acctcccaca cctcccctg    5580 aacctgaaac ataaaatgaa tgcaattgtt gttgttaact tgtttattgc agcttataat    5640
ggttacaaat aaagcaatag catcacaaat ttcacaaata aagcattttt ttcactgcat    5700
tctagttgtg gtttgtccaa actcatcaat gtatcttaag gcgtaaattg taagcgttaa    5760
tattttgtta aaattcgcgt taaattttg ttaaatcagc tcattttta accaataggc    5820 cgaaatcggc aaaatccctt ataaatcaaa agaatagacc gagatagggt tgagtgttgt    5880
tccagttggg aacaagagtc cactattaaa gaacgtggac tccaacgtca aagggcgaaa    5940
aaccgtctat cagggcgatg gcccactacg tgaaccatca ccctaatcaa gttttttggg    6000
gtcgaggtgc cgtaaagcac taaatcggaa ccctaaaggg agcccccgat ttagagcttg    6060
acggggaaag ccggcgaacg tggcgagaaa ggaagggaag aaagcgaaag gagcgggcgc    6120
tagggcgctg gcaagtgtag cggtcacgct gcgcgtaacc accacacccg ccgcgcttaa    6180
tgcgccgcta cagggcgcgt caggtggcac ttttcgggga aatgtgcgcg aaccccctat    6240
ttgtttattt ttctaaatac attcaaatat gtatccgctc atgagacaat aaccctgata    6300
aatgcttcaa taatattgaa aaaggaagag tcctgaggcg aaagaaccaa gctgtggaat    6360
gtgtgtcagt tagggtgtgg aaagtcccca ggctccccag caggcagaag tatgcaaagc    6420
atgcatctca attagtcagc aaccaggtgt ggaaagtccc caggctcccc agcaggcaga    6480
agtatgcaaa gcatgcatct caattagtca gcaaccatag tcccgcccct aactccgccc    6540
atcccgcccc taactccgcc cagttccgcc cattctccgc cccatggctg actaattttt    6600
tttatttatg cagaggccga ggccgcctcg gcctctgagc tattccagaa gtagtgagga    6660
ggcttttttg gaggcctagg cttttgcaaa gatcgatcaa gagacaggat gaggatcgtt    6720
```

```
tcgcatgatt gaacaagatg gattgcacgc aggttctccg gccgcttggg tggagaggct    6780
attcggctat gactgggcac aacagacaat cggctgctct gatgccgccg tgttccggct    6840
gtcagcgcag ggcgcccgg ttcttttgt caagaccgac ctgtccggtg ccctgaatga    6900
actgcaagac gaggcagcgc ggctatcgtg gctggcacg acgggcgttc cttgcgcagc    6960
tgtgctcgac gttgtcactg aagcgggaag ggactggctg ctattgggcg aagtgccggg    7020
gcaggatctc ctgtcatctc accttgctcc tgccgagaaa gtatccatca tggctgatgc    7080
aatgcggcgg ctgcatacgc ttgatccggc tacctgccca ttcgaccacc aagcgaaaca    7140
tcgcatcgag cgagcacgta ctcggatgga agccggtctt gtcgatcagg atgatctgga    7200
cgaagagcat caggggctcg cgccagccga actgttcgcc aggctcaagg cgagcatgcc    7260
cgacggcgag gatctcgtcg tgacccatgg cgatgcctgc ttgccgaata tcatggtgga    7320
aaatggccgc ttttctggat tcatcgactg tggccggctg ggtgtggcgg accgctatca    7380
ggacatagcg ttggctaccc gtgatattgc tgaagagctt gcggcgaat gggctgaccg    7440 cttcctcgtg ctttacggta tcgccgctcc cgattcgcag cgcatcgcct tctatcgcct    7500
tcttgacgag ttcttctgag cgggactctg gggttcgaaa tgaccgacca gcgacgccc    7560 aacctgccat cacgagattt cgattccacc gccgccttct atgaaaggtt gggcttcgga    7620
atcgttttcc gggacgccgg ctggatgatc ctccagcgcg gggatctcat gctggagttc    7680
ttcgcccacc ctaggggag gctaactgaa acacggaagg agacaatacc ggaaggaacc    7740
cgcgctatga cggcaataaa aagacagaat aaaacgcacg gtgttgggtc gtttgttcat    7800
aaacgcgggg ttcggtccca gggctggcac tctgtcgata ccccaccgag accccattgg    7860
ggccaatacg cccgcgtttc ttccttttcc cacccccacc ccccaagttc gggtgaaggc    7920
ccagggctcg cagccaacgt cggggcggca ggccctgcca tagcctcagg ttactcatat    7980
atactttaga ttgatttaaa acttcatttt taattttaaaa ggatctaggt gaagatcctt    8040
tttgataatc tcatgaccaa aatcccttaa cgtgagtttt cgttccactg agcgtcagac    8100
cccgtagaaa agatcaaagg atcttcttga tccttttttt ttctgcgcgt aatctgctgc    8160
ttgcaaacaa aaaaaccacc gctaccagcg gtggtttgtt tgccggatca agagctacca    8220 actcttttc cgaaggtaac tggcttcagc agagcgcaga taccaaatac tgtccttcta    8280
gtgtagccgt agttaggcca ccacttcaag aactctgtag caccgcctac atacctcgct    8340
ctgctaatcc tgttaccagt ggctgctgcc agtggcgata gtcgtgtct taccgggttg    8400 gactcaagac gatagttacc ggataaggcg cagcggtcgg gctgaacggg gggttcgtgc    8460
acacagccca gcttggagcg aacgacctac accgaactga gatacctaca gcgtgagcta    8520
tgagaaagcg ccacgcttcc cgaagggaga aaggcggaca ggtatccggt aagcggcagg    8580
gtcggaacag gagagcgcac gagggagctt ccaggggaa acgcctggta tctttatagt    8640
cctgtcgggt ttcgccacct ctgacttgag cgtcgatttt tgtgatgctc gtcagggggg    8700
cggagcctat ggaaaaacgc cagcaacgcg gcctttttac ggttcctggc cttttgctgg    8760
ccttttgctc acatgttctt tcctgcgtta tcccctgatt ctgtggataa ccgtattacc    8820
gccatgcat                                                            8829
```

<210> SEQ ID NO 9
<211> LENGTH: 10042
<212> TYPE: DNA
<213> ORGANISM: Artificial Sequence
<220> FEATURE:

<223> OTHER INFORMATION: pCAG-dCas9-5xPlat2AflD

<400> SEQUENCE: 9

| | | | | | |
|---|---|---|---|---|---:|
| tagttattaa | tagtaatcaa | ttacggggtc | attagttcat | agcccatata | tggagttccg | 60 |
| cgttacataa | cttacggtaa | atggcccgcc | tggctgaccg | cccaacgacc | cccgcccatt | 120 |
| gacgtcaata | atgacgtatg | ttcccatagt | aacgccaata | gggactttcc | attgacgtca | 180 |
| atgggtggac | tatttacggt | aaactgccca | cttggcagta | catcaagtgt | atcatatgcc | 240 |
| aagtacgccc | cctattgacg | tcaatgacgg | taaatggccc | gcctggcatt | atgcccagta | 300 |
| catgacctta | tgggactttc | ctacttggca | gtacatctac | gtattagtca | tcgctattac | 360 |
| catgggtcga | ggtgagcccc | acgttctgct | tcactctccc | catctccccc | cctccccac | 420 |
| ccccaatttt | gtatttattt | attttttaat | tattttgtgc | agcgatgggg | gcggggggg | 480 |
| gggggcgcg | cgccaggcgg | ggcggggcgg | ggcgagggc | gggcggggc | gaggcggaga | 540 |
| ggtgcggcgg | cagccaatca | gagcggcgcg | ctccgaaagt | ttcctttat | ggcgaggcgg | 600 |
| cggcggcggc | ggccctataa | aaagcgaagc | gcgcggcggg | cgggagtcgc | tgcgttgcct | 660 |
| tcgcccgtg | cccgctccg | cgccgcctcg | cgccgcccgc | cccggctctg | actgaccgcg | 720 |
| ttactcccac | aggtgagcgg | gcgggacggc | ccttctcctc | cgggctgtaa | ttagcgcttg | 780 |
| gtttaatgac | ggctcgtttc | ttttctgtgg | ctgcgtgaaa | gccttaaagg | gctccgggag | 840 |
| ggccctttgt | gcgggggga | gcggctcggg | gggtgcgtgc | gtgtgtgtgt | gcgtgggag | 900 |
| cgccgcgtgc | ggcccgcgct | gcccggcggc | tgtgagcgct | gcgggcgcgg | cgcggggctt | 960 |
| tgtgcgctcc | gcgtgtgcgc | gaggggagcg | cggccggggg | cggtgccccg | cggtgcgggg | 1020 |
| gggctgcgag | gggaacaaag | gctgcgtgcg | gggtgtgtgc | gtggggggt | gagcagggg | 1080 |
| tgtgggcgcg | gcgtcgggc | tgtaaccccc | ccctgcaccc | ccctcccga | gttgctgagc | 1140 |
| acggcccggc | ttcgggtgcg | gggctccgtg | cggggcgtgg | cgcggggctc | gccgtgccgg | 1200 |
| gcgggggtg | gcggcaggtg | ggggtgccgg | gcggggcggg | gccgcctcgg | gccggggagg | 1260 |
| gctcggggga | ggggcgcggc | ggccccggag | cgccggcggc | tgtcgaggcg | cggcgagccg | 1320 |
| cagccattgc | cttttatggt | aatcgtgcga | gagggcgcag | ggacttcctt | tgtcccaaat | 1380 |
| ctggcggagc | cgaaatctgg | gaggcgccgc | cgcacccct | ctagcgggcg | cgggcgaagc | 1440 |
| ggtgcggcgc | cggcaggaag | gaaatgggcg | ggagggcct | tcgtgcgtcg | ccgcgccgcc | 1500 |
| gtccccttct | ccatctccag | cctcggggct | gccgcagggg | gacggctgcc | ttcggggggg | 1560 |
| acggggcagg | gcggggttcg | gcttctggcg | tgtgaccggc | ggctctagag | cctctgctaa | 1620 |
| ccatgttcat | gccttcttct | ttttcctaca | gctcctgggc | aacgtgctgg | ttgttgtgct | 1680 |
| gtctcatcat | tttggcaaag | aattctgcag | tcgacggtac | cgcgggcccc | ctaggctacg | 1740 |
| cgcgccacca | tgcccaagaa | gaagcgcaag | gtgggacgcg | tctgcaggat | atcaagcttg | 1800 |
| cggtaccgcg | ggcccgggat | cgccaccatg | gacaagaagt | acagcatcgg | cctggccatc | 1860 |
| ggcaccaact | ctgtgggctg | ggccgtgatc | accgacgagt | acaaggtgcc | cagcaagaaa | 1920 |
| ttcaaggtgc | tgggcaacac | cgaccggcac | agcatcaaga | agaacctgat | cggcgccctg | 1980 |
| ctgttcgaca | gcggagaaac | agccgaggcc | acccggctga | agagaaccgc | cagaagaaga | 2040 |
| tacaccagac | ggaagaaccg | gatctgctat | ctgcaagaga | tcttcagcaa | cgagatggcc | 2100 |
| aaggtggacg | acagcttctt | ccacagactg | gaagagtcct | tcctggtgga | agaggataag | 2160 |
| aagcacgagc | ggcaccccat | cttcggcaac | atcgtgacg | aggtggccta | ccacgagaag | 2220 |
| tacccacca | tctaccacct | gagaaagaaa | ctggtggaca | gcaccgacaa | ggccgacctg | 2280 |

```
cggctgatct atctggccct ggcccacatg atcaagttcc ggggccactt cctgatcgag    2340
ggcgacctga accccgacaa cagcgacgtg gacaagctgt tcatccagct ggtgcagacc    2400
tacaaccagc tgttcgagga aaacccatc aacgccagcg cgtggacgc caaggccatc     2460 ctgtctgcca gactgagcaa gagcagacgg ctggaaaatc tgatcgccca gctgccggc    2520 gagaagaaga atggcctgtt cggcaacctg attgccctga gcctgggcct gaccccaac    2580 ttcaagagca acttcgacct ggccgaggat gccaaactgc agctgagcaa ggacacctac   2640
gacgacgacc tggacaacct gctggcccag atcggcgacc agtacgccga cctgtttctg   2700
gccgccaaga acctgtccga cgccatcctg ctgagcgaca tcctgagagt gaacaccgag   2760
atcaccaagg ccccctgag cgcctctatg atcaagagat acgacgagca ccaccaggac    2820
ctgaccctgc tgaaagctct cgtgcggcag cagctgcctg agaagtacaa agagattttc   2880
ttcgaccaga gcaagaacgg ctacgccggc tacatcgatg gcggagccag ccaggaagag   2940
ttctacaagt tcatcaagcc catcctggaa aagatggacg gcaccgagga actgctcgtg   3000
aagctgaaca gagaggacct gctgcggaag cagcggacct tcgacaacgg cagcatcccc   3060
caccagatcc acctgggaga gctgcacgcc attctgcggc ggcaggaaga ttttaccca    3120 ttcctgaagg acaaccggga aaagatcgag aagatcctga ccttccgcat cccctactac   3180
gtgggccctc tggccagggg aaacagcaga ttcgcctgga tgaccagaaa gagcgaggaa   3240
accatcaccc cctggaactt cgaggaagtg gtggacaagg gcgccagcgc ccagagcttc   3300
atcgagcgga tgaccaactt cgataagaac ctgcccaacg agaaggtgct gcccaagcac   3360
agcctgctgt acgagtactt caccgtgtac aacgagctga ccaaagtgaa atacgtgacc   3420
gagggaatga aaagcccgc cttcctgagc ggcgagcaga aaaagagccat cgtggacctg   3480 ctgttcaaga ccaaccggaa agtgaccgtg aagcagctga agaggactac ttcaagaaa    3540 atcgagtgct cgactccgt ggaaatctcc ggcgtggaag atcggttcaa cgcctccctg    3600
ggcacatacc acgatctgct gaaaattatc aaggacaagg acttcctgga caatgaggaa    3660
aacgaggaca ttctggaaga tatcgtgctg accctgacac tgtttgagga cagagagatg   3720
atcgaggaac ggctgaaaac ctatgccac ctgttcgacg acaaagtgat gaagcagctg    3780
aagcggcgga gatacaccgg ctggggcagg ctgagccgga agctgatcaa cggcatccgg   3840
gacaagcagt ccggcaagac aatcctggat ttcctgaagt ccgacggctt cgccaacaga    3900
aacttcatgc agctgatcca cgacgacagc ctgacctttta agaggacat ccagaaagcc    3960 caggtgtccg ccagggcga tagcctgcac gagcacattg ccaatctggc cggcagcccc   4020
gccattaaga agggcatcct gcagacagtg aaggtggtgg acgagctcgt gaaagtgatg   4080
ggccggcaca gcccgagaa catcgtgatc gaaatggcca gagagaacca gaccacccag   4140
aagggacaga agaacagccg cgagagaatg aagcggatcg aagagggcat caaagagctg   4200
ggcagccaga tcctgaaaga acaccccgtg gaaaacaccc agctgcagaa cgagaagctg    4260
tacctgtact acctgcagaa tgggcgggat atgtacgtgg accaggaact ggacatcaac    4320
cggctgtccg actacgatgt ggacgctatc gtgcctcaga gctttctgaa ggacgactcc    4380
atcgataaca aagtgctgac tcggagcgac aagaaccggg gcaagagcga caacgtgccc    4440
tccgaagagg tcgtgaagaa gatgaagaac tactggcgcc agctgctgaa tgccaagctg    4500
attacccaga ggaagttcga caatctgacc aaggccgaga gaggcggcct gagcgaactg    4560
gataaggccg gcttcatcaa gagacagctg gtggaaaccc ggcagatcac aaagcacgtg    4620
```

-continued

```
gcacagatcc tggactcccg gatgaacact aagtacgacg agaacgacaa actgatccgg     4680
gaagtgaaag tgatcaccct gaagtccaag ctggtgtccg atttccggaa ggatttccag     4740
ttttacaaag tgcgcgagat caacaactac caccacgccc acgacgccta cctgaacgcc     4800
gtcgtgggaa ccgcccctga tcaaaaagtac cctaagctgg aaagcgagtt cgtgtacggc     4860
gactacaagg tgtacgacgt gcggaagatg atcgccaaga gcgagcagga aatcggcaag     4920
gctaccgcca agtacttctt ctacagcaac atcatgaact tttcaagac cgagattacc     4980 ctggccaacg gcgagatccg gaagcggcct ctgatcgaga caaacggcga aacaggcgag     5040
atcgtgtggg ataagggccg ggactttgcc accgtgcgga aagtgctgtc tatgccccaa     5100
gtgaatatcg tgaaaaagac cgaggtgcag acaggcggct tcagcaaaga gtctatcctg     5160
cccaagagga acagcgacaa gctgatcgcc agaaagaagg actgggaccc taagaagtac     5220
ggcggcttcg acagccccac cgtggcctat tctgtgctgg tggtggccaa agtggaaaag     5280
ggcaagtcca gaaaactgaa gagtgtgaaa gagctgctgg ggatcaccat catggaaaga     5340
agcagcttcg agaagaatcc catcgacttt ctggaagcca agggctacaa agaagtgaaa     5400
aaggacctga tcatcaagct gcctaagtac tccctgttcg agctggaaaa cggccggaag     5460
agaatgctgg cctctgccgg cgaactgcag aagggaaacg aactggccct gccctccaaa     5520
tatgtgaact tcctgtacct ggccagccac tatgagaagc tgaagggctc ccccgaggat     5580
aatgagcaga acagctgttt tgtgaacag cacaaacact acctggacga gatcatcgag     5640
cagatcagcg agttctccaa gagagtgatc ctggccgacg ctaatctgga caaggtgctg     5700
agcgcctaca acaagcacag agacaagcct atcagagagc aggccgagaa tatcatccac     5760
ctgtttaccc tgaccaatct gggagcccct gccgccttca gtactttga caccaccatc     5820 gaccggaaga ggtacaccag caccaaagag gtgctggacg ccaccctgat ccaccagagc     5880
atcaccggcc tgtacgagac acggatcgac ctgtctcagc tgggaggcga cgcctatccc     5940
tatgacgtgc ccgattatgc cagcctgggc agcggctccc ccaagaaaaa acgcaaggtg     6000
gaagatccta gaaaaagcg gaaagtggac ggcattggta gtgggagcaa cggcagcagc     6060
ggatccaacg gtccgactga cgccgcggaa gaggagcttc tgagcaaaaa ctatcacctc     6120
gaaaacgagg ttgcgcgact gaagaaagga agcgggtccg gtggaagtgg ctccggatct     6180
ggaggttctg gcagcggagg tagcggcagt ggcgaagagc tccttagtaa gaactatcat     6240
ctggaaaatg aggtagcgcg cttaaagaaa gggtcgggaa gtggcggcag cggaagtggg     6300
agtggaggga gcggttctgg cggttccggc agtggagagg agttgctgtc taagaactac     6360
cacttagaaa acgaagtcgc acggctaaaa aaaggttccg gctccggcgg ctccggttct     6420
ggaagcgggg gctcgggatc aggtggatct ggatcaggag aggaattgct ttccaaaaac     6480
taccaccttg agaatgaggt ggccaggtta agaaggggga gcggctcggg gggtagtgga     6540
tcggggtcgg gcgggtcagg aagcggtggt agcggatctg ggaggagct gctctcgaag     6600 aattaccatt tggagaacga agtggcgaga ctaaagaagg gaagcggtag tggtggttca     6660
gggtctggtt caggtggcag tgggtctggg ggctcagggt ccgggtaggc ggccgcgact     6720
ctagatcata atcagccata ccacatttgt agaggtttta cttgctttaa aaaacctccc     6780
acacctcccc ctgaacctga aacataaaat gaatgcaatt gttgttgtta acttgtttat     6840
tgcagcttat aatggttaca ataaagcaa tagcatcaca aatttcacaa ataaagcatt     6900
tttttcactg cattctagtt gtggtttgtc caaactcatc aatgtatctt aaggcgtaaa     6960
ttgtaagcgt taatattttg ttaaaattcg cgttaaattt ttgttaaatc agctcatttt     7020
```

```
ttaaccaata ggccgaaatc ggcaaaatcc cttataaatc aaaagaatag accgagatag   7080
ggttgagtgt tgttccagtt tggaacaaga gtccactatt aaagaacgtg gactccaacg   7140
tcaaagggcg aaaaaccgtc tatcagggcg atggcccact acgtgaacca tcaccctaat   7200 caagttttt ggggtcgagg tgccgtaaag cactaaatcg gaaccctaaa gggagccccc    7260
gatttagagc ttgacgggga aagccggcga acgtggcgag aaaggaaggg aagaaagcga   7320
aaggagcggg cgctagggcg ctggcaagtg tagcggtcac gctgcgcgta accaccacac   7380
ccgccgcgct taatgcgccg ctacagggcg cgtcaggtgg cacttttcgg ggaaatgtgc   7440
gcggaacccc tatttgttta ttttctaaa tacattcaaa tatgtatccg ctcatgagac    7500
aataaccctg ataaatgctt caataatatt gaaaaaggaa gagtcctgag gcggaaagaa   7560
ccagctgtgg aatgtgtgtc agttagggtg tggaaagtcc ccaggctccc cagcaggcag   7620
aagtatgcaa agcatgcatc tcaattagtc agcaaccagg tgtggaaagt ccccaggctc   7680
cccagcaggc agaagtatgc aaagcatgca tctcaattag tcagcaacca tagtcccgcc   7740
cctaactccg cccatcccgc cctaactcc gcccagttcc gcccattctc cgccccatgg    7800
ctgactaatt ttttattt atgcagaggc cgaggccgcc tcggcctctg agctattcca     7860
gaagtagtga ggaggctttt ttggaggcct aggcttttgc aaagatcgat caagagacag   7920
gatgaggatc gtttcgcatg attgaacaag atggattgca cgcaggttct ccggccgctt   7980
gggtggagag gctattcggc tatgactggg cacaacagac aatcggctgc tctgatgccg   8040
ccgtgttccg gctgtcagcg caggggcgcc cggttctttt tgtcaagacc gacctgtccg   8100
gtgccctgaa tgaactgcaa gacgaggcag cgcggctatc gtggctggcc acgacgggcg   8160
ttccttgcgc agctgtgctc gacgttgtca ctgaagcggg aagggactgg ctgctattgg   8220
gcgaagtgcc ggggcaggat ctcctgtcat ctcaccttgc tcctgccgag aaagtatcca   8280
tcatggctga tgcaatgcgg cggctgcata cgcttgatcc ggctacctgc ccattcgacc   8340
accaagcgaa acatcgcatc gagcgagcac gtactcggat ggaagccggt cttgtcgatc   8400
aggatgatct ggacgaagag catcaggggc tcgcgccagc cgaactgttc gccaggctca   8460
aggcgagcat gcccgacggc gaggatctcg tcgtgaccca tggcgatgcc tgcttgccga   8520
atatcatggt ggaaaatggc cgcttttctg gattcatcga ctgtggccgg ctgggtgtgg   8580
cggaccgcta tcaggacata gcgttggcta cccgtgatat tgctgaagag cttggcggcg   8640
aatgggctga ccgcttcctc gtgctttacg gtatcgccgc tcccgattcg cagcgcatcg   8700
ccttctatcg ccttcttgac gagttcttct gagcgggact ctggggttcg aaatgaccga   8760
ccaagcgacg cccaacctgc catcacgaga tttcgattcc accgccgcct tctatgaaag   8820 gttggcttc ggaatcgttt tccgggacgc cggctgatg atcctccagc gcggggatct     8880
catgctggag ttcttcgccc accctagggg gaggctaact gaaacacgga aggagacaat   8940
accggaagga acccgcgcta tgacggcaat aaaaagacag aataaaacgc acggtgttgg   9000
gtcgtttgtt cataaacgcg gggttcggtc ccagggctgg cactctgtcg ataccccacc   9060
gagaccccat tggggccaat acgcccgcgt ttcttccttt tccccacccc accccccaag   9120
ttcgggtgaa ggcccagggc tcgcagccaa cgtcggggcg gcaggccctg ccatagcctc   9180
aggttactca tatatacttt agattgattt aaaacttcat ttttaattta aaaggatcta   9240
ggtgaagatc cttttgata atctcatgac caaaatccct aacgtgagt ttcgttcca      9300 ctgagcgtca gaccccgtag aaaagatcaa aggatcttct tgagatcctt ttttctgcg    9360
```

| | |
|---|---|
| cgtaatctgc tgcttgcaaa caaaaaaacc accgctacca gcggtggttt gtttgccgga | 9420 |
| tcaagagcta ccaactcttt ttccgaaggt aactggcttc agcagagcgc agataccaaa | 9480 |
| tactgtcctt ctagtgtagc cgtagttagg ccaccacttc aagaactctg tagcaccgcc | 9540 |
| tacataccctc gctctgctaa tcctgttacc agtggctgct gccagtggcg ataagtcgtg | 9600 |
| tcttaccggg ttggactcaa gacgatagtt accggataag gcgcagcggt cgggctgaac | 9660 |
| ggggggttcg tgcacacagc ccagcttgga gcgaacgacc tacaccgaac tgagatacct | 9720 |
| acagcgtgag ctatgagaaa gcgccacgct tcccgaaggg agaaaggcgg acaggtatcc | 9780 |
| ggtaagcggc agggtcggaa caggagagcg cacgagggag cttccagggg gaaacgcctg | 9840 |
| gtatctttat agtcctgtcg ggtttcgcca cctctgactt gagcgtcgat ttttgtgatg | 9900 |
| ctcgtcaggg gggcggagcc tatgaaaaa cgccagcaac gcggcctttt tacggttcct | 9960 |
| ggccttttgc tggccttttg ctcacatgtt ctttcctgcg ttatcccctg attctgtgga | 10020 |
| taaccgtatt accgccatgc at | 10042 |

<210> SEQ ID NO 10
<211> LENGTH: 10042
<212> TYPE: DNA
<213> ORGANISM: Artificial Sequence
<220> FEATURE:
<223> OTHER INFORMATION: pCAG-dCas9-3.5xSuper

<400> SEQUENCE: 10

| | |
|---|---|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggac tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catgggtcga ggtgagcccc acgttctgct tcactctccc catctccccc cctccccac | 420 |
| ccccaatttt gtatttattt attttttaat tattttgtgc agcgatgggg gcgggggggg | 480 |
| gggggggcgcg cgccaggcgg ggcggggcgg ggcgagggg ggggcggggc gaggcggaga | 540 |
| ggtgcggcgg cagccaatca gagcggcgcg ctccgaaagt ttcctttat ggcgaggcgg | 600 |
| cggcggcggc ggccctataa aaagcgaagc gcgcggcggg cgggagtcgc tgcgttgcct | 660 |
| tcgccccgtg ccccgctccg cgccgcctcg cgccgcccgc cccggctctg actgaccgcg | 720 |
| ttactcccac aggtgagcgg gcgggacggc ccttctcctc cgggctgtaa ttagcgcttg | 780 |
| gtttaatgac ggctcgtttc ttttctgtgg ctgcgtgaaa gccttaaagg ctccgggag | 840 |
| ggccctttgt gcgggggga gcggctcggg gggtgcgtgc gtgtgtgtgt gcgtggggag | 900 |
| cgccgcgtgc ggcccgcgct gcccggcggc tgtgagcgct gcgggcgcgg cgcggggctt | 960 |
| tgtgcgctcc gcgtgtgcgc gaggggagcg cggccggggg cggtgccccg cggtgcgggg | 1020 |
| gggctgcgag gggaacaaag gctgcgtgcg gggtgtgtgc gtgggggggt gagcagggg | 1080 |
| tgtgggcgcg gcgtcgggc tgtaacccc ccctgcaccc cctccccga gttgctgagc | 1140 |
| acggcccggc ttcgggtgcg gggctccgtg cggggcgtgg cgcggggctc gccgtgccgg | 1200 |
| gcgggggtg gcggcaggtg ggggtgccgg gcggggcggg gccgcctcgg gccggggagg | 1260 |
| gctcggggga gggcgcggc ggccccgag cgccggcggc tgtcgaggcg cggcgagccg | 1320 |
| cagccattgc ctttatggt aatcgtgcga gagggcgcag ggacttcctt tgtcccaaat | 1380 |

```
ctggcggagc cgaaatctgg gaggcgccgc cgcacccct ctagcgggcg cgggcgaagc   1440
ggtgcggcgc cggcaggaag gaaatgggcg gggagggcct tcgtgcgtcg ccgcgccgcc   1500
gtccccttct ccatctccag cctcgggct gccgcagggg gacggctgcc ttcgggggg    1560 acggggcagg gcggggttcg gcttctggcg tgtgaccggc ggctctagag cctctgctaa   1620
ccatgttcat gccttcttct ttttcctaca gctcctgggc aacgtgctgg ttgttgtgct   1680
gtctcatcat tttggcaaag aattctgcag tcgacggtac cgcgggccc ctaggctacg    1740 cgcgccacca tgcccaagaa gaagcgcaag gtgggacgcg tctgcaggat atcaagcttg   1800
cggtaccgcg ggcccgggat cgccaccatg gacaagaagt acagcatcgg cctggccatc   1860
ggcaccaact ctgtgggctg gccgtgatc accgacgagt acaaggtgcc cagcaagaaa    1920
ttcaaggtgc tgggcaacac cgaccggcac agcatcaaga gaacctgat cggcgccctg    1980 ctgttcgaca gcggagaaac agccgaggcc accggctga agagaaccgc cagaagaaga   2040
tacaccagac ggaagaaccg gatctgctat ctgcaagaga tcttcagcaa cgagatggcc   2100
aaggtggacg acagcttctt ccacagactg gaagagtcct tcctggtgga agaggataag   2160
aagcacgagc ggcaccccat cttcggcaac atcgtggacg aggtggccta ccacgagaag   2220
taccccacca tctaccacct gagaaagaaa ctggtggaca gcaccgacaa ggccgacctg   2280
cggctgatct atctggccct ggcccacatg atcaagttcc ggggccactt cctgatcgag   2340
ggcgacctga ccccgacaa cagcgacgtg gacaagctgt tcatccagct ggtgcagacc   2400
tacaaccagc tgttcgagga aaaccccatc aacgccagcg gcgtggacgc caaggccatc   2460
ctgtctgcca gactgagcaa gagcagacgg ctggaaaatc tgatcgccca gctgcccggc   2520
gagaagaaga atggcctgtt cggcaacctg attgccctga gcctgggcct gaccccaac    2580 ttcaagagca acttcgacct ggccgaggat gccaaactgc agctgagcaa ggacacctac   2640
gacgacgacc tggacaacct gctggcccag atcggcgacc agtacgccga cctgtttctg   2700
gccgccaaga acctgtccga cgccatcctg ctgagcgaca tcctgagagt gaacaccgag   2760
atcaccaagg ccccctgag cgcctctatg atcaagagat acgacgagca ccaccaggac   2820
ctgaccctgc tgaaagctct cgtgcggcag cagctgcctg agaagtacaa agagattttc   2880
ttcgaccaga gcaagaacgg ctacgccggc tacatcgatg gcggagccag ccaggaagag   2940
ttctacaagt tcatcaagcc catcctggaa aagatggacg gcaccgagga actgctcgtg   3000
aagctgaaca gagaggacct gctgcggaag cagcggacct tcgacaacgg cagcatcccc   3060
caccagatcc acctgggaga gctgcacgcc attctgcgc ggcaggaaga ttttacccca   3120
ttcctgaagg acaaccggga aaagatcgag aagatcctga ccttccgcat ccctactac    3180 gtgggccctc tggccagggg aaacagcaga ttcgcctgga tgaccagaaa gagcgaggaa   3240
accatcaccc cctggaactt cgaggaagtg gtggacaagg gcgccagcgc ccagagcttc   3300
atcgagcgga tgaccaactt cgataagaac ctgcccaacg agaaggtgct gcccaagcac   3360
agcctgctgt acgagtactt caccgtgtac aacgagctga ccaaagtgaa atacgtgacc   3420
gagggaatga gaaagcccgc cttcctgagc ggcgagcaga aaaaagccat cgtggacctg   3480
ctgttcaaga ccaaccggaa agtgaccgtg aagcagctga aagaggacta cttcaagaaa   3540
atcgagtgct tcgactccgt ggaaatctcc ggcgtggaag atcggttcaa cgcctccctg   3600
ggcacatacc acgatctgct gaaaattatc aaggacaagg acttcctgga caatgaggaa   3660
aacgaggaca ttctggaaga tatcgtgctg accctgacac tgtttgagga cagagagatg   3720
```

```
atcgaggaac ggctgaaaac ctatgcccac ctgttcgacg acaaagtgat gaagcagctg   3780
aagcggcgga gatacaccgg ctggggcagg ctgagccgga agctgatcaa cggcatccgg   3840
gacaagcagt ccggcaagac aatcctggat ttcctgaagt ccgacggctt cgccaacaga   3900
aacttcatgc agctgatcca cgacgacagc ctgaccttta agaggacat  ccagaaagcc   3960 caggtgtccg gccagggcga tagcctgcac gagcacattg ccaatctggc cggcagcccc   4020
gccattaaga agggcatcct gcagacagtg aaggtggtgg acgagctcgt gaaagtgatg   4080
ggccggcaca agcccgagaa catcgtgatc gaaatggcca gagagaacca gaccacccag   4140
aagggacaga agaacagccg cgagagaatg aagcggatcg aagagggcat caaagagctg   4200
ggcagccaga tcctgaaaga acaccccgtg gaaaacaccc agctgcagaa cgagaagctg   4260
tacctgtact acctgcagaa tgggcgggat atgtacgtgg accaggaact ggacatcaac   4320
cggctgtccg actacgatgt ggacgctatc gtgcctcaga gctttctgaa ggacgactcc   4380
atcgataaca aagtgctgac tcggagcgac aagaaccggg gcaagagcga caacgtgccc   4440
tccgaagagg tcgtgaagaa gatgaagaac tactggcgcc agctgctgaa tgccaagctg   4500
attacccaga ggaagttcga caatctgacc aaggccgaga gaggcggcct gagcgaactg   4560
gataaggccg gcttcatcaa gagacagctg gtggaaaccc ggcagatcac aaagcacgtg   4620
gcacagatcc tggactcccg gatgaacact aagtacgacg agaacgacaa actgatccgg   4680
gaagtgaaag tgatcaccct gaagtccaag ctggtgtccg atttccggaa ggatttccag   4740
ttttacaaag tgcgcgagat caacaactac caccacgccc acgacgccta cctgaacgcc   4800
gtcgtgggaa ccgccctgat caaaaagtac cctaagctgg aaagcgagtt cgtgtacggc   4860
gactacaagg tgtacgacgt gcggaagatg atcgccaaga gcgagcagga aatcggcaag   4920
gctaccgcca gtactttctt ctacagcaac atcatgaact ttttcaagac cgagattacc   4980
ctggccaacg gcgagatccg gaagcggcct ctgatcgaga caaacggcga aacaggcgag   5040
atcgtgtggg ataagggccg ggactttgcc accgtgcgga aagtgctgtc tatgccccaa   5100
gtgaatatcg tgaaaaagac cgaggtgcag acaggcggct tcagcaaaga gtctatcctg   5160
cccaagagga cagcgacaa gctgatcgcc agaaagaagg actgggaccc taagaagtac   5220
ggcggcttcg acagccccac cgtggcctat tctgtgctgg tggtggccaa agtggaaaag   5280
ggcaagtcca gaaactgaa gagtgtgaaa gagctgctgg ggatcaccat catggaaaga   5340
agcagcttcg agaagaatcc catcgacttt ctggaagcca agggctacaa agaagtgaaa   5400
aaggacctga tcatcaagct gcctaagtac tcccctgttcg agctgaaaaa cggccggaag   5460
agaatgctgg cctctgccgg cgaactgcag aagggaaacg aactggccct gccctccaaa   5520
tatgtgaact tcctgtacct ggccagccac tatgagaagc tgaagggctc ccccgaggat   5580
aatgagcaga aacagctgtt tgtggaacag cacaaacact acctggacga gatcatcgag   5640
cagatcagcg agttctccaa gagagtgatc ctggccgacg ctaatctgga caaggtgctg   5700
agcgcctaca acaagcacag agacaagcct atcagagagg aggccgagaa tatcatccac   5760
ctgtttaccc tgaccaatct gggagcccct gccgccttca gtactttgga caccaccatc   5820
gaccggaaga ggtacaccag caccaaagag gtgctggacg ccaccctgat ccaccagagc   5880
atcaccggcc tgtacgagac acggatcgac ctgtctcagc tgggaggcga cgcctatccc   5940
tatgacgtgc ccgattatgc cagcctgggc agcggctccc ccaagaaaaa acgcaaggtg   6000
gaagatccta gaaaaagcg gaaagtggac ggcattggta gtgggagcaa cggcagcagc   6060
ggatccaacg gtccgactga cgccgcggaa gaggaactcc tatcaaagaa ttatcacttg   6120
```

```
gaaaacgaag tggctagact gaaaaagggg tcgggaagcg gaggtagtgg gtctggagga      6180
agcggatcag gaggtagcgg ctccggcgga tcggtgggt ccggctcagg cggatcgggt       6240 tctgggggt caggttcagg tggatctggt ccggcgaag aactcctttc caagaactac        6300
catttggaga atgaagtggc cagactcaag aaagggagcg gtccggtgg ctccggatct       6360 ggtggatcgg gaagtggggg atcaggttcc ggagggtcag gcggttcagg gtcaggaggc      6420
agtggctcgg gggggagcgg ctctggcggc tcagggtcgg gagaggagtt actcagtaag      6480
aactatcacc tcgaaaatga agtcgctcgc ctcaaaaaag gatcaggatc tggcgggtct      6540
gggagtggcg gcagcggtag cggcggaagt ggttctggtg ggtcagggg ctccggtagc       6600 ggggaagtg gcagtggagg gtcgggtagc ggtggttcag gttcggggga agaacttctc       6660
agcaagaatt accacctaga gaacgaagta gcccgcctaa aaagtaggc ggccgcgact       6720 ctagatcata atcagccata ccacatttgt agaggtttta cttgctttaa aaaacctccc     6780
acacctcccc ctgaacctga aacataaaat gaatgcaatt gttgttgtta acttgtttat      6840
tgcagcttat aatggttaca aataaagcaa tagcatcaca aatttcacaa ataaagcatt      6900
tttttcactg cattctagtt gtggtttgtc caaactcatc aatgtatctt aaggcgtaaa      6960
ttgtaagcgt taatatttg ttaaaattcg cgttaaattt ttgttaaatc agctcatttt        7020
ttaaccaata ggccgaaatc ggcaaaatcc cttataaatc aaaagaatag accgagatag      7080
ggttgagtgt tgttccagtt tggaacaaga gtccactatt aaagaacgtg gactccaacg     7140
tcaaagggcg aaaaaccgtc tatcagggcg atggcccact acgtgaacca tcaccctaat     7200
caagtttttt ggggtcgagg tgccgtaaag cactaaatcg gaaccctaaa gggagccccc     7260
gatttagagc ttgacgggga aagccggcga acgtggcgag aaaggaaggg aagaaagcga     7320
aaggagcggg cgctagggcg ctggcaagtg tagcggtcac gctgcgcgta accaccacac     7380
ccgccgcgct taatgcgccg ctacagggcg cgtcaggtgg cacttttcgg ggaaatgtgc     7440 gcggaaccc tatttgttta ttttttctaaa tacattcaaa tatgtatccg ctcatgagac     7500
aataaccctg ataaatgctt caataatatt gaaaaaggaa gagtcctgag gcggaaagaa     7560
ccagctgtgg aatgtgtgtc agttagggtg tggaaagtcc ccaggctccc cagcaggcag     7620
aagtatgcaa agcatgcatc tcaattagtc agcaaccagg tgtggaaagt ccccaggctc      7680
cccagcaggc agaagtatgc aaagcatgca tctcaattag tcagcaacca tagtcccgcc     7740
cctaactccg cccatcccgc ccctaactcc gcccagttcc gcccattctc cgccccatgg     7800
ctgactaatt ttttttattt atgcagaggc cgaggccgcc tcggcctctg agctattcca     7860
gaagtagtga ggaggctttt ttggaggcct aggcttttgc aaagatcgat caagagacag     7920
gatgaggatc gtttcgcatg attgaacaag atggattgca cgcaggttct ccggccgctt     7980
gggtggagag gctattcggc tatgactggg cacaacagac aatcggctgc tctgatgccg     8040
ccgtgttccg gctgtcagcg caggggcgcc cggttctttt tgtcaagacc gacctgtccg     8100
gtgccctgaa tgaactgcaa gacgaggcag cgcggctatc gtggctggcc acgacgggcg     8160
ttccttgcgc agctgtgctc gacgttgtca ctgaagcggg aagggactgg ctgctattgg     8220
gcgaagtgcc ggggcaggat ctcctgtcat ctcaccttgc tcctgccgag aaagtatcca     8280
tcatggctga tgcaatgcgg cggctgcata cgcttgatcc ggctacctgc ccattcgacc     8340
accaagcgaa acatcgcatc gagcgagcac gtactcggat ggaagccggt cttgtcgatc     8400
aggatgatct ggacgaagag catcaggggc tcgcgccagc cgaactgttc gccaggctca     8460
```

| | |
|---|---:|
| aggcgagcat gcccgacggc gaggatctcg tcgtgaccca tggcgatgcc tgcttgccga | 8520 |
| atatcatggt ggaaaatggc cgcttttctg gattcatcga ctgtggccgg ctgggtgtgg | 8580 |
| cggaccgcta tcaggacata gcgttggcta cccgtgatat tgctgaagag cttggcggcg | 8640 |
| aatgggctga ccgcttcctc gtgctttacg gtatcgccgc tcccgattcg cagcgcatcg | 8700 |
| ccttctatcg ccttcttgac gagttcttct gagcgggact ctggggttcg aaatgaccga | 8760 |
| ccaagcgacg cccaacctgc catcacgaga tttcgattcc accgccgcct tctatgaaag | 8820 |
| gttgggcttc ggaatcgttt ccgggacgc cggctggatg atcctccagc gcggggatct | 8880 |
| catgctggag ttcttcgccc accctagggg gaggctaact gaaacacgga aggagacaat | 8940 |
| accggaagga acccgcgcta tgacggcaat aaaaagacag aataaaacgc acggtgttgg | 9000 |
| gtcgtttgtt cataaacgcg gggttcggtc cagggctgg cactctgtcg atacccacc | 9060 |
| gagacccat tggggccaat acgcccgcgt tcttcctttt tccccacccc accccccaag | 9120 |
| ttcgggtgaa ggcccagggc tcgcagccaa cgtcggggcg gcaggccctg ccatagcctc | 9180 |
| aggttactca tatatacttt agattgattt aaaacttcat ttttaattta aaaggatcta | 9240 |
| ggtgaagatc cttttgata atctcatgac caaaatccct taacgtgagt tttcgttcca | 9300 |
| ctgagcgtca gaccccgtag aaaagatcaa aggatcttct tgagatcctt tttttctgcg | 9360 |
| cgtaatctgc tgcttgcaaa caaaaaaacc accgctacca gcggtggttt gtttgccgga | 9420 |
| tcaagagcta ccaactcttt ttccgaaggt aactggcttc agcagagcgc agataccaaa | 9480 |
| tactgtcctt ctagtgtagc cgtagttagg ccaccacttc aagaactctg tagcaccgcc | 9540 |
| tacatacctc gctctgctaa tcctgttacc agtggctgct gccagtggcg ataagtcgtg | 9600 |
| tcttaccggg ttggactcaa gacgatagtt accggataag gcgcagcggt cgggctgaac | 9660 |
| ggggggttcg tgcacacagc ccagcttgga gcgaacgacc tacaccgaac tgagatacct | 9720 |
| acagcgtgag ctatgagaaa gcgccacgct tcccgaaggg agaaaggcgg acaggtatcc | 9780 |
| ggtaagcggc agggtcggaa caggagagcg cacgagggag cttccagggg gaaacgcctg | 9840 |
| gtatctttat agtcctgtcg ggtttcgcca cctctgactt gagcgtcgat ttttgtgatg | 9900 |
| ctcgtcaggg gggcggagcc tatggaaaaa cgccagcaac gcggcctttt tacgttcct | 9960 |
| ggccttttgc tggccttttg ctcacatgtt ctttcctgcg ttatcccctg attctgtgga | 10020 |
| taaccgtatt accgccatgc at | 10042 |

```
<210> SEQ ID NO 11
<211> LENGTH: 14283
<212> TYPE: DNA
<213> ORGANISM: Artificial Sequence
<220> FEATURE:
<223> OTHER INFORMATION: pPlatTET-gRNA2

<400> SEQUENCE: 11
```

| | |
|---|---:|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggac tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catgggtcga ggtgagcccc acgttctgct tcactctccc catctccccc cctccccac | 420 |
| ccccaatttt gtatttattt attttttaat tattttgtgc agcgatgggg gcggggggg | 480 |

```
gggggggcgcg cgccaggcgg ggcggggcgg ggcgagggc ggggcggggc gaggcggaga       540
ggtgcggcgg cagccaatca gagcggcgcg ctccgaaagt ttcctttat ggcgaggcgg       600
cggcggcggc ggccctataa aaagcgaagc gcgcggcggg cgggagtcgc tgcgttgcct       660
tcgcccgtg ccccgctccg cgccgcctcg cgccgcccgc cccggctctg actgaccgcg       720
ttactcccac aggtgagcgg gcgggacggc ccttctcctc cgggctgtaa ttagcgcttg       780
gtttaatgac ggctcgtttc ttttctgtgg ctgcgtgaaa gccttaaagg gctccgggag       840
ggccctttgt gcggggggga gcggctcggg gggtgcgtgc gtgtgtgtgt gcgtggggag       900
cgccgcgtgc ggcccgcgct gcccggcggc tgtgagcgct gcgggcgcgg cgcggggctt       960
tgtgcgctcc gcgtgtgcgc gaggggagcg cggccggggg cggtgccccg cggtgcgggg      1020
gggctgcgag gggaacaaag gctgcgtgcg gggtgtgtgc gtgggggggt gagcaggggg      1080
tgtgggcgcg gcggtcgggc tgtaaccccc ccctgcaccc ccctccccga gttgctgagc      1140
acggccccggc ttcgggtgcg gggctccgtg cggggcgtgg cgcggggctc gccgtgccgg      1200
gcgggggtg gcggcaggtg ggggtgccgg gcggggcggg gccgcctcgg gccggggagg      1260
gctcggggga ggggcgcggc ggccccggag cgccggcggc tgtcgaggcg cggcgagccg      1320
cagccattgc ctttatggt aatcgtgcga gagggcgcag ggacttcctt tgtcccaaat      1380
ctggcggagc cgaaatctgg gaggcgccgc cgcacccct ctagcgggcg cgggcgaagc      1440
ggtgcggcgc cggcaggaag gaaatgggcg gggagggcct tcgtgcgtcg ccgcgccgcc      1500
gtccccttct ccatctccag cctcggggct gccgcagggg gacggctgcc ttcgggggg      1560
acggggcagg gcggggttcg gcttctggcg tgtgaccggc ggctctagag cctctgctaa      1620
ccatgttcat gccttcttct ttttcctaca gctcctgggc aacgtgctgg ttgttgtgct      1680
gtctcatcat tttggcaaag aattcccccg cgatcgcgcc accatgccca agaagaagcg      1740
caaggtggga cgcgtctgca ggatatcaag cttgcggtac cgcggccccg ggatcgccac      1800
catggacaag aagtacagca tcggcctggc catcggcacc aactctgtgg gctgggccgt      1860
gatcaccgac gagtacaagg tgcccagcaa gaaattcaag gtgctgggca acaccgaccg      1920
gcacagcatc aagaagaacc tgatcggcgc cctgctgttc gacagcggag aaacagccga      1980
ggccaccccgg ctgaagagaa ccgccagaag aagatacacc agacggaaga accggatctg      2040
ctatctgcaa gagatcttca gcaacagat ggccaaggtg gacgacagct tcttccacag      2100
actggaagag tccttcctgg tggaagagga taagaagcac gagcggcacc ccatcttcgg      2160
caacatcgtg gacgaggtgg cctaccacga gaagtacccc accatctacc acctgagaaa      2220
gaaactggtg gacagcaccg acaaggccga cctgcggctg atctatctgg ccctggccca      2280
catgatcaag ttccggggcc acttcctgat cgagggcgac ctgaaccccg acaacagcga      2340
cgtggacaag ctgttcatcc agctggtgca gacctacaac cagctgttcg aggaaaaccc      2400
catcaacgcc agcggcgtgg acgccaaggc catcctgtct gccagactga gcaagagcag      2460
acggctggaa aatctgatcg cccagctgcc cggcgagaag aagaatggcc tgttcggcaa      2520
cctgattgcc ctgagcctgg gcctgacccc caacttcaag agcaacttcg acctggccga      2580
ggatgccaaa ctgcagctga gcaaggacac ctacgacgac gacctggaca acctgctggc      2640
ccagatcggc gaccagtacg ccgacctgtt tctggccgcc aagaacctgt ccgacgccat      2700
cctgctgagc gacatcctga gagtgaacac cgagatcacc aaggccccc tgagcgcctc      2760
tatgatcaag agatacgacg agcaccacca ggacctgacc ctgctgaaag ctctcgtgcg      2820
```

```
gcagcagctg cctgagaagt acaaagagat tttcttcgac cagagcaaga acggctacgc   2880
cggctacatc gatggcggag ccagccagga agagttctac aagttcatca agcccatcct   2940
ggaaaagatg gacggcaccg aggaactgct cgtgaagctg aacagagagg acctgctgcg   3000
gaagcagcgc accttcgaca acggcagcat ccccccaccag atccacctgg agagctgca   3060 cgccattctg cggcggcagg aagattttta cccattcctg aaggacaacc gggaaaagat   3120
cgagaagatc ctgacctccc gcatccccta ctacgtgggc cctctggcca ggggaaacag   3180
cagattcgcc tggatgacca aaagagcga ggaaaccatc accccctgga acttcgagga   3240
agtggtggac aagggcgcca cgcccagag cttcatcgag cggatgacca acttcgataa   3300
gaacctgccc aacgagaagg tgctgcccaa gcacagcctg ctgtacgagt acttcaccgt   3360
gtacaacgag ctgaccaaag tgaaatacgt gaccgaggga atgagaaagc ccgccttcct   3420
gagcggcgag cagaaaaaag ccatcgtgga cctgctgttc aagaccaacc ggaaagtgac   3480
cgtgaagcag ctgaaagagg actacttcaa gaaaatcgag tgcttcgact ccgtggaaat   3540
ctccggcgtg gaagatcggt tcaacgcctc cctgggcaca taccacgatc tgctgaaaat   3600
tatcaaggac aaggacttcc tggacaatga ggaaaacgag gacattctgg aagatatcgt   3660
gctgaccctg acactgtttg aggacagaga gatgatcgag aacggctga aaacctatgc   3720 ccacctgttc gacgacaaag tgatgaagca gctgaagcgg cggagataca ccggctgggg   3780
caggctgagc cggaagctga tcaacggcat ccggacaag cagtccggca agacaatcct   3840
ggatttcctg aagtccgacg gcttcgccaa cagaaacttc atgcagctga tccacgacga   3900
cagcctgacc tttaaagagg acatccagaa agcccaggtg tccggccagg gcgatagcct   3960
gcacgagcac attgccaatc tggccggcag ccccgccatt aagaagggca tcctgcagac   4020
agtgaaggtg gtggacgagc tcgtgaaagt gatgggccgg cacaagcccg agaacatcgt   4080
gatcgaaatg gccagagaga accagaccac ccagaagga cagaagaaca gccgcgagag   4140
aatgaagcgg atcgaagagg gcatcaaaga gctgggcagc cagatcctga aagaacaccc   4200
cgtggaaaac acccagctgc agaacgagaa gctgtacctg tactacctgc agaatgggcg   4260
ggatatgtac gtggaccagg aactggacat caaccggctg tccgactacg atgtggacgc   4320
tatcgtgcct cagagctttc tgaaggacga ctccatcgat aacaaagtgc tgactcggag   4380
cgacaagaac cggggcaaga gcgacaacgt gcccctccgaa gaggtcgtga agaagatgaa   4440
gaactactgg cgccagctgc tgaatgccaa gctgattacc cagaggaagt tcgacaatct   4500
gaccaaggcc gagagaggcg gcctgagcga actggataag gccggcttca tcaagagaca   4560
gctggtggaa acccggcaga tcacaaagca cgtggcacag atcctggact cccggatgaa   4620
cactaagtac gacgagaacg acaaactgat ccgggaagtg aaagtgatca ccctgaagtc   4680
caagctggtg tccgatttcc ggaaggattt ccagttttac aaagtgcgcg agatcaacaa   4740
ctaccaccac gcccacgacg cctacctgaa cgccgtcgtg ggaaccgccc tgatcaaaaa   4800
gtaccctaag ctggaaagcg agttcgtgta cggcgactac aaggtgtacg acgtgcggaa   4860
gatgatcgcc aagagcgagc aggaaatcgg caaggctacc gccaagtact tcttctacag   4920
caacatcatg aacttttttca agaccgagat taccctggcc aacggcgaga tccggaagcg   4980
gcctctgatc gagacaaacg gcgaaacagg cgagatcgtg tgggataagg ccgggactt   5040 tgccaccgtg cggaaagtgc tgtctatgcc ccaagtgaat atcgtgaaaa agaccgaggt   5100
gcagacaggc ggcttcagca agagtctat cctgcccaag aggaacagcg acaagctgat   5160
cgccagaaag aaggactggg accctaagaa gtacggcggc ttcgacagcc ccaccgtggc   5220
```

```
ctattctgtg ctggtggtgg ccaaagtgga aagggcaag tccaagaaac tgaagagtgt    5280
gaaagagctg ctgggatca ccatcatgga aagaagcagc ttcgagaaga atcccatcga    5340
ctttctggaa gccaagggct acaaagaagt gaaaaaggac ctgatcatca agctgcctaa    5400
gtactccctg ttcgagctgg aaaacggccg aagagaatg ctggcctctg ccggcgaact    5460
gcagaaggga aacgaactgg ccctgccctc caaatatgtg aacttcctgt acctggccag    5520
ccactatgag aagctgaagg gctcccccga ggataatgag cagaaacagc tgtttgtgga    5580
acagcacaaa cactacctgg acgagatcat cgagcagatc agcgagttct ccaagagagt    5640
gatcctggcc gacgctaatc tggacaaggt gctgagcgcc tacaacaagc acagagacaa    5700
gcctatcaga gagcaggccg agaatatcat ccacctgttt accctgacca atctgggagc    5760
ccctgccgcc ttcaagtact ttgacaccac catcgaccgg aagaggtaca ccagcaccaa    5820
agaggtgctg gacgccaccc tgatccacca gagcatcacc ggcctgtacg agacacggat    5880
cgacctgtct cagctgggag cgacgccta tccctatgac gtgcccgatt atgccagcct    5940
gggcagcggc tcccccaaga aaaacgcaa ggtggaagat cctaagaaaa agcggaaagt    6000
ggacggcatt ggtagtggga gcaacggcag cagcggatcc aacggtccga ctgacgccgc    6060
ggaagaggag cttctgagca aaaactatca cctcgaaaac gaggttgcgc gactgaagaa    6120
aggaagcggg tccggtggaa gtggctccgg atctggaggt tctggcagcg gaggtagcgg    6180
cagtggcgaa gagctcctta gtaagaacta tcatctggaa aatgaggtag cgcgcttaaa    6240
gaaagggtcg ggaagtggcg gcagcggaag tgggagtgga gggagcggtt ctggcggttc    6300
cggcagtgga gaggagttgc tgtctaagaa ctaccactta gaaaacgaag tcgcacggct    6360
aaaaaaaggt tccggctccg gcggctccgg ttctggaagc gggggctcgg gatcaggtgg    6420
atctggatca ggagaggaat tgctttccaa aaactaccac cttgagaatg aggtggccag    6480
gttaaagaag gggagcggct cgggggtag tggatcgggg tcgggcgggt caggaagcgg    6540
tggtagcgga tctgggagg agctgctctc gaagaattac catttggaga acgaagtggc    6600
gagactaaag aagggaagcg gtagtggtgg ttcagggtct ggttcaggtg cagtgggtc    6660 tgggggctca gggtccggga cggccggcct cggaagcgga gctactaact tcagcctgct    6720
gaagcaggct ggagacgtgg aggagaaccc tggacctagt accatgggcc ccgacatcgt    6780
gatgacccag agcccccagca gcctgagcgc cagcgtgggc gaccgcgtga ccatcacctg    6840
ccgcagcagc accggcgccg tgaccaccag caactacgcc agctgggtgc aggagaagcc    6900
cggcaagctg ttcaagggcc tgatcggcgg caccaacaac cgcgccccg gcgtgcccag    6960 ccgcttcagc ggcagcctga tcggcgacaa ggccaccctg accatcagca gcctgcagcc    7020
cgaggacttc gccaccctact tctgcgcccct gtggtacagc aaccactggg tgttcggcca    7080
gggcaccaag gtggagctga agcgcggcgg cggcggcagc ggcggcggcg cagcggcgg    7140 cggcggcagc agcggcggcg cagcgaggt gaagctgctg gagagcggcg gcggcctggt    7200
gcagcccggc ggcagcctga gctgagctg cgccgtgagc ggcttcagcc tgaccgacta    7260
cggcgtgaac tgggtgcgcc aggccccccgg ccgcggcctg gagtggatcg gcgtgatctg    7320
gggcgacggc atcaccgact acaacagcgc cctgaaggac cgcttcatca tcagcaagga    7380
caacggcaag aacaccgtgt acctgcagat gagcaaggtg cgcagcgacg acaccgccct    7440
gtactactgc gtgaccggcc tgttcgacta ctggggccag ggcacccctgg tgaccgtgag    7500 cagctaccca tacgatgttc cagattacgc tggtggaggc ggaggttctg ggggaggagg    7560
```

```
tagtggcggt ggtggttcag gaggcggcgg aagcttggat ccaggtggag gtggaagcgg    7620
tagcaaagga gaagaacttt tcactggagt tgtcccaatt cttgttgaat tagatggtga    7680
tgttaatggg cacaaatttt ctgtccgtgg agagggtgaa ggtgatgcta caaacggaaa    7740
actcacccct aaatttattt gcactactgg aaaactacct gttccgtggc caacacttgt    7800
cactactctg acctatggtg ttcaatgctt ttcccgttat ccggatcaca tgaaacggca    7860 tgacttttc aagagtgcca tgcccgaagg ttatgtacag aacgcacta tatctttcaa     7920 agatgacggg acctacaaga cgcgtgctga agtcaagttt gaaggtgata cccttgttaa    7980
tcgtatcgag ttaaagggta ttgattttaa agaagatgga acattcttg gacacaaact     8040 cgagtacaac tttaactcac acaatgtata catcacggca gacaaacaaa gaatggaat     8100 caaagctaac ttcaaaattc gccacaacgt tgaagatggt tccgttcaac tagcagacca    8160
ttatcaacaa aatactccaa ttggcgatgg ccctgtcctt ttaccagaca accattacct    8220
gtcgacacaa tctgtccttt cgaaagatcc aacgaaaag cgtgaccaca tggtccttct      8280
tgagtttgta actgctgctg ggattacaca tggcatggat gagctctaca aaggtggagg    8340
tcggaccggt ggcggtggcg gaggggctag cagatccgaa ctgcccacct gcagctgtct    8400
tgatcgagtt atacaaaaag acaaaggccc atattataca caccttgggg caggaccaag    8460
tgttgctgct gtcagggaaa tcatggagaa taggtatggt caaaaaggaa acgcaataag    8520
gatagaaata gtagtgtaca ccggtaaaga agggaaaagc tctcatgggt gtccaattgc    8580
taagtgggtt ttaagaagaa gcagtgatga agaaaagtt ctttgtttgg tccggcagcg     8640
tacaggccac cactgtccaa ctgctgtgat ggtggtgctc atcatggtgt gggatggcat    8700
ccctcttcca atggccgacc ggctatacac agagctcaca gagaatctaa agtcatacaa    8760
tgggcaccct accgacagaa gatgcaccct caatgaaaat cgtacctgta catgtcaagg    8820
aattgatcca gagacttgtg agcttcatt ctcttttggc tgttcatgga gtatgtactt      8880
taatggctgt aagtttggta gaagcccaag ccccagaaga tttagaattg atccaagctc    8940
tcccttacat gaaaaaaacc ttgaagataa cttacagagt ttggctacac gattagctcc    9000
aatttataag cagtatgctc cagtagctta ccaaaatcag gtggaatatg aaaatgttgc    9060
ccgagaatgt cggcttggca gcaaggaagg tcgtccctic tctggggtca ctgcttgcct    9120
ggacttctgt gctcatcccc acagggacat tcacaacatg aataatggaa gcactgtggt    9180
ttgtacctta actcgagaag ataaccgctc tttgggtgtt attcctcaag atgagcagct    9240
ccatgtgcta cctctcttata agctttcaga cacagatgag tttggctcca aggaaggaat    9300
ggaagccaag atcaaatctg gggccatcga ggtcctggca ccccgccgca aaaaagaac    9360 gtgtttcact cagcctgttc cccgttctgg aaagaagagg gctgcgatga tgacagaggt    9420
tcttgcacat aagataaggg cagtggaaaa gaaacctatt ccccgaatca gcggaagaa    9480 taactcaaca acaacaaaca acagtaagcc ttcgtcactg ccaaccttag ggagtaacac    9540
tgagaccgtg caacctgaag taaaaagtga accgaaccc cattttatct aaaaagttc     9600 agacaacact aaaacttatt cgctgatgcc atccgctcct cacccagtga agaggcatc    9660 tccaggcttc tcctggtccc cgaagactgc ttcagccaca ccagctccac tgaagaatga   9720
cgcaacagcc tcatgcgggt tttcagaaag aagcagcact ccccactgta cgatgccttc    9780
gggaagactc agtggtgcca atgcagctgc tgctgatggc cctggcattt cacagcttgg    9840
cgaagtggct cctctcccca ccctgtctgc tcctgtgatg gagcccctca ttaattctga    9900
gccttccact ggtgtgactg agccgctaac gcctcatcag ccaaaccacc agccctcctt    9960
```

```
cctcacctct cctcaagacc ttgcctcttc tccaatggaa gaagatgagc agcattctga   10020
agcagatgag cctccatcag acgaacccct atctgatgac ccctgtcac ctgctgagga    10080 gaaattgccc cacattgatg agtattggtc agacagtgag cacatctttt tggatgcaaa   10140
tattggtggg gtggccatcg cacctgctca cggctcggtt ttgattgagt gtgcccggcg   10200
agagctgcac gctaccactc ctgttgagca ccccaaccgt aatcatccaa cccgcctctc   10260
ccttgtcttt taccagcaca aaaacctaaa taagccccaa catggttttg aactaaacaa   10320
gattaagttt gaggctaaag aagctaagaa taagaaaatg aaggcctcag agcaaaaaga   10380
ccaggcagct aatgaaggtc cagaacagtc ctctgaagta aatgaattga accaaattcc   10440
ttctcataaa gcattaacat aacccatga caatgttgtc accgtgtccc cttatgctct    10500
cacacacgtt gcggggccct ataaccattg ggtctgagcg gccgcgactc tagatcataa   10560
tcagccatac cacatttgta gaggttttac ttgctttaaa aaacctccca cacctccccc   10620
tgaacctgaa acataaaatg aatgcaattg ttgttgttaa cttgtttatt gcagcttata   10680
atggttacaa ataaagcaat agcatcacaa atttcacaaa taaagcattt ttttcactgc   10740
attctagttg tggtttgtcc aaactcatca atgtatcttg gcgcgcctgt acaaaaaagc   10800
aggctttaaa ggaaccaatt cagtcgactg gatccggtac caaggtcggg caggaagagg   10860
gcctatttcc catgattcct tcatatttgc atatacgata caaggctgtt agagagataa   10920
ttagaattaa tttgactgta aacacaaaga tattagtaca aaatacgtga cgtagaaagt   10980
aataatttct tgggtagttt gcagttttaa aattatgttt taaatggac tatcatatgc    11040 ttaccgtaac ttgaaagtat ttcgatttct tggctttata tatcttaagt taaaataagg   11100
ctagtccgtt atcaacttga aaaagtggca ccgagtcggt gctttttttc tagacccagc   11160
tttcttgtac aaagttggca ttaggcgcgc caaggcgtaa attgtaagcg ttaatatttt   11220
gttaaaattc gcgttaaatt tttgttaaat cagctcattt tttaaccaat aggccgaaat   11280
cggcaaaatc ccttataaat caaaagaata gaccgagata gggttgagtg ttgttccagt   11340
ttggaacaag agtccactat taagaacgt ggactccaac gtcaaagggc gaaaaaccgt    11400
ctatcagggc gatggcccac tacgtgaacc atcaccctaa tcaagttttt tggggtcgag   11460
gtgccgtaaa gcactaaatc ggaaccctaa agggagcccc cgatttagag cttgacgggg   11520
aaagccggcg aacgtggcga gaaaggaagg gaagaaagcg aaaggagcgg gcgctagggc   11580
gctggcaagt gtagcggtca cgctgcgcgt aaccaccaca cccgccgcgc ttaatgcgcc   11640
gctacagggc gcgtcaggtg gcacttttcg ggaaatgtg cgcggaaccc ctatttgttt     11700
atttttctaa atacattcaa atatgtatcc gctcatgaga caataaccct gataaatgct   11760
tcaataatat tgaaaagga agagtcctga ggcggaaaga accagctgtg gaatgtgtgt    11820
cagttagggt gtggaaagtc cccaggctcc ccagcaggca gaagtatgca aagcatgcat   11880
ctcaattagt cagcaaccag gtgtggaaag tccccaggct ccccagcagg cagaagtatg   11940
caaagcatgc atctcaatta gtcagcaacc atagtcccgc ccctaactcc gcccatcccg   12000
cccctaactc cgcccagttc cgcccattct ccgccccatg ctgactaat ttttttttatt    12060 tatgcagagg ccgaggccgc ctcggcctct gagctattcc agaagtagtg aggaggcttt   12120
tttggaggcc taggcttttg caaagatcga tcaagagaca ggatgaggat cgtttcgcat   12180
gattgaacaa gatggattgc acgcaggttc tccggccgct tgggtggaga ggctattcgg   12240
ctatgactgg gcacaacaga caatcggctg ctctgatgcc gccgtgttcc ggctgtcagc   12300
```

```
gcaggggcgc ccggttctttt tgtcaagac cgacctgtcc ggtgccctga atgaactgca    12360
agacgaggca gcgcggctat cgtggctggc cacgacgggc gttccttgcg cagctgtgct    12420
cgacgttgtc actgaagcgg gaagggactg gctgctattg ggcgaagtgc cggggcagga    12480
tctcctgtca tctcacccttg ctcctgccga gaaagtatcc atcatggctg atgcaatgcg    12540
gcggctgcat acgcttgatc cggctacctg cccattcgac caccaagcga acatcgcat    12600 cgagcgagca cgtactcgga tggaagccgg tcttgtcgat caggatgatc tggacgaaga    12660
gcatcagggg ctcgcgccag ccgaactgtt cgccaggctc aaggcgagca tgcccgacgg    12720
cgaggatctc gtcgtgaccc atggcgatgc ctgcttgccg aatatcatgg tggaaaatgg    12780
ccgcttttct ggattcatcg actgtggccg gctgggtgtg gcggaccgct atcaggacat    12840
agcgttggct acccgtgata ttgctgaaga gcttggcggc gaatgggctg accgcttcct    12900
cgtgctttac ggtatcgccg ctcccgattc gcagcgcatc gccttctatc gccttcttga    12960
cgagttcttc tgagcgggac tctggggttc gaaatgaccg accaagcgac gcccaacctg    13020
ccatcacgag atttcgattc caccgccgcc ttctatgaaa ggttgggctt cggaatcgtt    13080
ttccgggacg ccggctggat gatcctccag cgcggggatc tcatgctgga gttcttcgcc    13140
caccctaggg ggaggctaac tgaaacacgg aaggagacaa taccggaagg aacccgcgct    13200
atgacggcaa taaaaagaca gaataaaacg cacggtgttg ggtcgtttgt tcataaacgc    13260
ggggttcggt cccagggctg gcactctgtc gatacccac cgagacccca ttggggccaa    13320
tacgcccgcg tttcttcctt tccccaccc cacccccaa gttcgggtga aggcccaggg    13380
ctcgcagcca acgtcgggc ggcaggcct gccatagcct caggttactc atatatactt    13440
tagattgatt taaaacttca tttttaattt aaaaggatct aggtgaagat cctttttgat    13500
aatctcatga ccaaaatccc ttaacgtgag ttttcgttcc actgagcgtc agaccccgta    13560
gaaaagatca aggatcttc ttgagatcct ttttttctgc gcgtaatctg ctgcttgcaa    13620
acaaaaaaac caccgctacc agcggtggtt tgtttgccgg atcaagagct accaactctt    13680
tttccgaagg taactggctt cagcagagcg cagataccaa atactgtcct tctagtgtag    13740
ccgtagttag gccaccactt caagaactct gtagcaccgc ctacatacct cgctctgcta    13800
atcctgttac cagtggctgc tgccagtggc gataagtcgt gtcttaccgg gttggactca    13860
agacgatagt taccggataa ggcgcagcgg tcggctgaa cggggggttc gtgcacacag    13920
cccagcttgg agcgaacgac ctacaccgaa ctgagatacc tacagcgtga gctatgagaa    13980
agcgccacgc ttcccgaagg gagaaaggcg gacaggtatc cggtaagcgg cagggtcgga    14040
acaggagagc gcacgaggga gcttccaggg ggaaacgcct ggtatcttta tagtcctgtc    14100
gggtttcgcc acctctgact tgagcgtcga ttttttgtgat gctcgtcagg ggggcggagc    14160
ctatggaaaa acgccagcaa cgcggccttt ttacggttcc tggccttttg ctggccttttt    14220 gctcacatgt tctttcctgc gttatcccct gattctgtgg ataaccgtat taccgccatg    14280
cat                                                                  14283
```

<210> SEQ ID NO 12
<211> LENGTH: 23
<212> TYPE: DNA
<213> ORGANISM: Artificial Sequence
<220> FEATURE:
<223> OTHER INFORMATION: Gfap_1

<400> SEQUENCE: 12
atagacataa tggtcagggg tgg                                             23

<210> SEQ ID NO 13
<211> LENGTH: 23
<212> TYPE: DNA
<213> ORGANISM: Artificial Sequence
<220> FEATURE:
<223> OTHER INFORMATION: Gfap_2

<400> SEQUENCE: 13
ggatgccagg atgtcagccc cgg                                        23

<210> SEQ ID NO 14
<211> LENGTH: 23
<212> TYPE: DNA
<213> ORGANISM: Artificial Sequence
<220> FEATURE:
<223> OTHER INFORMATION: Gfap_3

<400> SEQUENCE: 14
atatggcaag ggcagccccg tgg                                        23

<210> SEQ ID NO 15
<211> LENGTH: 23
<212> TYPE: DNA
<213> ORGANISM: Artificial Sequence
<220> FEATURE:
<223> OTHER INFORMATION: H19DMR_1

<400> SEQUENCE: 15
gtgggggggc tctttaggtt tgg                                        23

<210> SEQ ID NO 16
<211> LENGTH: 23
<212> TYPE: DNA
<213> ORGANISM: Artificial Sequence
<220> FEATURE:
<223> OTHER INFORMATION: H19DMR_2

<400> SEQUENCE: 16
accctggtct ttacacacaa agg                                        23

<210> SEQ ID NO 17
<211> LENGTH: 23
<212> TYPE: DNA
<213> ORGANISM: Artificial Sequence
<220> FEATURE:
<223> OTHER INFORMATION: H19DMR_3

<400> SEQUENCE: 17
gaagctgtta tgtgcaacaa ggg                                        23

<210> SEQ ID NO 18
<211> LENGTH: 23
<212> TYPE: DNA
<213> ORGANISM: Artificial Sequence
<220> FEATURE:
<223> OTHER INFORMATION: H19DMR_4

<400> SEQUENCE: 18
cagatttggc tatagctaaa tgg                                        23

<210> SEQ ID NO 19
<211> LENGTH: 20
<212> TYPE: DNA
<213> ORGANISM: Artificial Sequence
<220> FEATURE:

<223> OTHER INFORMATION: UR_1

<400> SEQUENCE: 19
ccattattgc attaatctga                                              20

<210> SEQ ID NO 20
<211> LENGTH: 20
<212> TYPE: DNA
<213> ORGANISM: Artificial Sequence
<220> FEATURE:
<223> OTHER INFORMATION: UR_2

<400> SEQUENCE: 20
taatgcagcc agaaaatgac                                              20

<210> SEQ ID NO 21
<211> LENGTH: 20
<212> TYPE: DNA
<213> ORGANISM: Artificial Sequence
<220> FEATURE:
<223> OTHER INFORMATION: UR_3

<400> SEQUENCE: 21
tcagggatca aattctgagc                                              20

<210> SEQ ID NO 22
<211> LENGTH: 25
<212> TYPE: DNA
<213> ORGANISM: Artificial Sequence
<220> FEATURE:
<223> OTHER INFORMATION: GfapSTAT3-B3

<400> SEQUENCE: 22
ttggttagtt tttaggattt ttttt                                        25

<210> SEQ ID NO 23
<211> LENGTH: 26
<212> TYPE: DNA
<213> ORGANISM: Artificial Sequence
<220> FEATURE:
<223> OTHER INFORMATION: GfapSTAT3-B4

<400> SEQUENCE: 23
aaaacttcaa acccatctat ctcttc                                       26

<210> SEQ ID NO 24
<211> LENGTH: 25
<212> TYPE: DNA
<213> ORGANISM: Artificial Sequence
<220> FEATURE:
<223> OTHER INFORMATION: H19DMR-B1

<400> SEQUENCE: 24
aaggagatta tgttttattt ttgga                                        25

<210> SEQ ID NO 25
<211> LENGTH: 25
<212> TYPE: DNA
<213> ORGANISM: Artificial Sequence
<220> FEATURE:
<223> OTHER INFORMATION: H19DMR-B2

<400> SEQUENCE: 25
aaaaaaactc aatcaattac aatcc                                        25

```
<210> SEQ ID NO 26
<211> LENGTH: 28
<212> TYPE: DNA
<213> ORGANISM: Artificial Sequence
<220> FEATURE:
<223> OTHER INFORMATION: Gfap_O1B1

<400> SEQUENCE: 26
ttgtaaaggt aggattaata agggaatt                                          28

<210> SEQ ID NO 27
<211> LENGTH: 26
<212> TYPE: DNA
<213> ORGANISM: Artificial Sequence
<220> FEATURE:
<223> OTHER INFORMATION: Gfap_O1B2

<400> SEQUENCE: 27
aaaaaaaacc cttcaaaaaa aatcta                                            26

<210> SEQ ID NO 28
<211> LENGTH: 25
<212> TYPE: DNA
<213> ORGANISM: Artificial Sequence
<220> FEATURE:
<223> OTHER INFORMATION: Gfap_O2B1

<400> SEQUENCE: 28
ttattattta tatttggagg gaggg                                             25

<210> SEQ ID NO 29
<211> LENGTH: 25
<212> TYPE: DNA
<213> ORGANISM: Artificial Sequence
<220> FEATURE:
<223> OTHER INFORMATION: Gfap_O2B2

<400> SEQUENCE: 29
attacaccaa aaaaatttta aaaac                                             25

<210> SEQ ID NO 30
<211> LENGTH: 25
<212> TYPE: DNA
<213> ORGANISM: Artificial Sequence
<220> FEATURE:
<223> OTHER INFORMATION: Gfap_O3B1

<400> SEQUENCE: 30 tttaaattt tttatgtgaa tatgg                                              25

<210> SEQ ID NO 31
<211> LENGTH: 25
<212> TYPE: DNA
<213> ORGANISM: Artificial Sequence
<220> FEATURE:
<223> OTHER INFORMATION: Gfap_O3B2

<400> SEQUENCE: 31
aaacatttaa ttcattaata cacac                                             25

<210> SEQ ID NO 32
<211> LENGTH: 25
<212> TYPE: DNA
<213> ORGANISM: Artificial Sequence
<220> FEATURE:
<223> OTHER INFORMATION: GfapSTAT3-B1
```

<400> SEQUENCE: 32
gttgaagatt tggtagtgtt gagtt                                         25

<210> SEQ ID NO 33
<211> LENGTH: 25
<212> TYPE: DNA
<213> ORGANISM: Artificial Sequence
<220> FEATURE:
<223> OTHER INFORMATION: GfapSTAT3-B2

<400> SEQUENCE: 33
taaaacatat aacaaaaaca acccc                                         25

<210> SEQ ID NO 34
<211> LENGTH: 26
<212> TYPE: DNA
<213> ORGANISM: Artificial Sequence
<220> FEATURE:
<223> OTHER INFORMATION: H19DMR-B3

<400> SEQUENCE: 34
gggttttttt ggttattgaa ttttaa                                        26

<210> SEQ ID NO 35
<211> LENGTH: 26
<212> TYPE: DNA
<213> ORGANISM: Artificial Sequence
<220> FEATURE:
<223> OTHER INFORMATION: H19DMR-B4

<400> SEQUENCE: 35
aatacacaca tcttaccacc cctata                                        26

<210> SEQ ID NO 36
<211> LENGTH: 25
<212> TYPE: DNA
<213> ORGANISM: Artificial Sequence
<220> FEATURE:
<223> OTHER INFORMATION: H19DMR-B5

<400> SEQUENCE: 36
tttttgggta gttttttag ttttg                                          25

<210> SEQ ID NO 37
<211> LENGTH: 28
<212> TYPE: DNA
<213> ORGANISM: Artificial Sequence
<220> FEATURE:
<223> OTHER INFORMATION: H19DMR-B6

<400> SEQUENCE: 37
acacaaatac ctaatcccctt tattaaac                                     28

<210> SEQ ID NO 38
<211> LENGTH: 23
<212> TYPE: DNA
<213> ORGANISM: Artificial Sequence
<220> FEATURE:
<223> OTHER INFORMATION: off target 1

<400> SEQUENCE: 38
gtgacacagg atgtcagccc ggg                                           23

<210> SEQ ID NO 39
<211> LENGTH: 23

```
<212> TYPE: DNA
<213> ORGANISM: Artificial Sequence
<220> FEATURE:
<223> OTHER INFORMATION: off target 2

<400> SEQUENCE: 39
ccatgctggg atgtcagccc tgg                                              23

<210> SEQ ID NO 40
<211> LENGTH: 23
<212> TYPE: DNA
<213> ORGANISM: Artificial Sequence
<220> FEATURE:
<223> OTHER INFORMATION: off target 3

<400> SEQUENCE: 40
gtcaccttgg atgtcagccc cgg                                              23

<210> SEQ ID NO 41
<211> LENGTH: 9243
<212> TYPE: DNA
<213> ORGANISM: Artificial Sequence
<220> FEATURE:
<223> OTHER INFORMATION: pCAG-scFvGCN4sfGFPDnmt3bF

<400> SEQUENCE: 41
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggac tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catgggtcga ggtgagcccc acgttctgct tcactctccc catctccccc cctccccac      420 ccccaatttt gtatttattt attttttaat tattttgtgc agcgatgggg gcggggggg      480 gggggcgcg cgccaggcgg ggcggggcgg ggcgagggc ggggcgggc gaggcggaga        540 ggtgcggcgg cagccaatca gagcggcgcg ctccgaaagt ttcctttat ggcgaggcgg      600 cggcggcggc ggccctataa aaagcgaagc gcgggcggg cgggagtcgc tgcgttgcct      660
tcgccccgtg ccccgctccg cgccgcctcg cgccgcccgc cccggctctg actgaccgcg     720
ttactcccac aggtgagcgg gcgggacggc ccttctcctc cgggctgtaa ttagcgcttg     780
gtttaatgac ggctcgtttc ttttctgtgg ctgcgtgaaa gccttaaagg ctccggagag    840 ggcccttgt gcggggggga gcggctcggg gggtgcgtgc gtgtgtgtgt gcgtggggag     900
cgccgcgtgc ggcccgcgct gcccggcggc tgtgagcgct gcgggcgcgg cgcgggctt     960 tgtgcgctcc gcgtgtgcgc gagggagcg cggccggggg cggtgccccg cggtgcgggg    1020
gggctgcgag gggaacaaag gctgcgtgcg gggtgtgtgc gtggggggt gagcaggggg    1080 tgtgggcgcg gcggtcgggc tgtaaccccc ccctgcaccc ccctccccga gttgctgagc   1140
acggcccggc ttcgggtgcg gggctccgtg cggggcgtgg cgcggggctc gccgtgccgg   1200
gcggggggtg gcggcaggtg ggggtgccgg cggggcgggg ccgcctcgg gccggggagg   1260 gctcggggga ggggcgcggc ggcccccgag cgccggcggc tgtcgaggcg cggcgagccg   1320
cagccattgc cttttatggt aatcgtgcga gagggcgcag ggacttcctt tgtcccaaat   1380
ctggcggagc cgaaatctgg gaggcgccgc cgcacccct ctagcgggcg cgggcgaagc    1440
```

```
ggtgcggcgc cggcaggaag gaaatgggcg gggagggcct tcgtgcgtcg ccgcgccgcc    1500
gtccccttct ccatctccag cctcggggct gccgcagggg gacggctgcc ttcgggggg     1560 acggggcagg gcggggttcg gcttctggcg tgtgaccggc ggctctagag cctctgctaa   1620
ccatgttcat gccttcttct ttttcctaca gctcctgggc aacgtgctgg ttgttgtgct   1680
gtctcatcat tttggcaaag aattctgcag tcgacggtac catgggcccc gacatcgtga   1740
tgacccagag ccccagcagc ctgagcgcca gcgtgggcga ccgcgtgacc atcacctgcc   1800
gcagcagcac cggcgccgtg accaccagca actacgccag ctgggtgcag agaagcccg    1860 gcaagctgtt caagggcctg atcggcggca ccaacaaccg cgcccccggc gtgcccagcc   1920
gcttcagcgg cagcctgatc ggcgacaagg ccaccctgac catcagcagc ctgcagcccg   1980
aggacttcgc cacctacttc tgcgccctgt ggtacagcaa ccactgggtg ttcggccagg   2040
gcaccaaggt ggagctgaag cgcggcggcg gcggcagcgg cggcggcggc agcggcggcg   2100
gcggcagcag cggcggcggc agcgaggtga agctgctgga gagcggcggc ggcctggtgc   2160
agcccggcgg cagcctgaag ctgagctgcg ccgtgagcgg cttcagcctg accgactacg   2220
gcgtgaactg ggtgcgccag gccccccggcc gcggcctgga gtggatcggc gtgatctggg   2280
gcgacggcat caccgactac aacagcgccc tgaaggaccg cttcatcatc agcaaggaca   2340
acggcaagaa caccgtgtac ctgcagatga gcaaggtgcg cagcgacgac accgccctgt   2400
actactgcgt gaccggcctg ttcgactact ggggccaggg caccctggtg accgtgagca   2460
gctacccata cgatgttcca gattacgctg gtggaggcgg aggttctggg ggaggaggta   2520
gtggcggtgg tggttcagga ggcggcggaa gcttggatcc aggtggaggt ggaagcggta   2580
gcaaaggaga agaacttttc actggagttg tcccaattct tgttgaatta gatggtgatg   2640
ttaatgggca caaattttct gtccgtggag agggtgaagg tgatgctaca aacggaaaac   2700
tcacccttaa atttatttgc actactggaa aactacctgt tccgtggcca cacttgtca    2760 ctactctgac ctatggtgtt caatgctttt cccgttatcc ggatcacatg aaacggcatg   2820 acttttcaa gagtgccatg cccgaaggtt atgtacagga acgcactata tctttcaaag    2880
atgacgggac ctacaagacg cgtgctgaag tcaagtttga aggtgatacc cttgttaatc   2940
gtatcgagtt aaagggtatt gattttaaag aagatggaaa cattcttgga cacaaactcg   3000
agtacaactt taactcacac aatgtataca tcacggcaga caaacaaaag aatggaatca   3060
aagctaactt caaaattcgc cacaacgttg aagatggttc cgttcaacta gcagaccatt   3120
atcaacaaaa tactccaatt ggcgatggcc ctgtccttt accagacaac cattacctgt    3180
cgacacaatc tgtcctttcg aaagatccca acgaaaagcg tgaccacatg gtccttcttg   3240
agtttgtaac tgctgctggg attacacatg gcatggatga actctacaaa ggtgaggtc    3300 ggaccggtgg cggtggcgga ggggctagca tgaagggaga cagcagacat ctgaatgaag   3360
aagagggtgc cagcgggtat gaggagtgca ttatcgttaa tgggaacttc agtgaccagt   3420
cctcagacac gaaggatgct ccctcacccc cagtcttgga ggcaatctgc acagagccag   3480
tctgcacacc agagaccaga ggccgcaggt caagctcccg gctgtctaag agggaggtct   3540
ccagccttct gaattacacg caggacatga cagagatgg agacagagat gatgaagtag   3600
atgatgggaa tggctctgat attctaatgc aaagctcac ccgtgagacc aaggacacca   3660
ggacgcgctc tgaaagcccg ctgtccgaa cccgacatag caatgggacc tccagcttgg   3720
agaggcaaag agcctccccc agaatcaccc gaggtcggca gggccgccac catgtgcagg   3780
agtaccctgt ggagtttccg gctaccaggt ctcggagacg tcgagcatca tcttcagcaa   3840
```

```
gcacgccatg gtcatcccct gccagcgtcg acttcatgga agaagtgaca cctaagagcg    3900
tcagtacccc atcagttgac ttgagccagg atggagatca ggagggtatg gataccacac    3960
aggtggatgc agagagcaga gatggagaca gcacagagta tcaggatgat aaagagtttg    4020
gaataggtga cctcgtgtgg ggaaagatca agggcttctc ctggtggcct gccatggtgg    4080
tgtcctggaa agccacctcc aagcgacagg ccatgcccgg aatgcgctgg gtacagtggt    4140
ttggtgatgg caagttttct gagatctctg ctgacaaact ggtggctctg gggctgttca    4200
gccagcactt taatctggct accttcaata agctggtttc ttataggaag gccatgtacc    4260
acactctgga gaaagccagg gttcgagctg caagaccttc tccagcagt cctggagagt    4320 cactggagga ccagctgaag cccatgctgg agtgggccca cggtggcttc aagcctactg    4380
ggatcgaggg cctcaaaccc aacaagaagc aaccagtggt taataagtcg aaggtgcgtc    4440
gttcagacag taggaactta gaacccagga gacgcgagaa caaaagtcga agacgcacaa    4500
ccaatgactc tgctgcttct gagtccccc cacccaagcg cctcaagaca aatagctatg    4560
gcgggaagga ccgaggggag gatgaggaga gccgagaacg gatggcttct gaagtcacca    4620
acaacaaggg caatctggaa gaccgctgtt gtcctgtgg aaagaagaac cctgtgtcct    4680
tccaccccct ctttgagggt gggctctgtc agagttgccg ggatcgcttc ctagagctct    4740
tctacatgta tgatgaggac ggctatcagt cctactgcac cgtgtgctgt gagggccgtg    4800
aactgctgct gtgcagtaac acaagctgct gcagatgctt ctgtgtggag tgtctggagg    4860
tgctggtggg cgcaggcaca gctgaggatg ccaagctgca ggaaccctgg agctgctata    4920
tgtgcctccc tcagcgctgc catggggtcc tccgacgcag gaaagattgg aacatgcgcc    4980
tgcaagactt cttcactact gatcctgacc tggaagaatt tgagccaccc aagttgtacc    5040
cagcaattcc tgcagccaaa aggaggccca ttagagtcct gtctctgttt gatggaattg    5100
caacggggta cttggtgctc aaggagttgg gtattaaagt ggaaaagtac attgcctccg    5160
aagtctgtgc agagtccatc gctgtgggaa ctgttaagca tgaaggccag atcaaatatg    5220
tcaatgacgt ccggaaaatc accaagaaaa atattgaaga gtgggcccg ttcgacttgg    5280 tgattggtgg aagcccatgc aatgatctct ctaacgtcaa tcctgcccgc aaaggtttat    5340
atgagggcac aggaaggctc ttcttcgagt tttaccactt gctgaattat acccgccca    5400 aggagggcga caaccgtcca ttcttctgga tgttcgagaa tgttgtggcc atgaaagtga    5460
atgacaagaa agacatctca agattcctgg catgtaaccc agtgatgatc gatgccatca    5520
aggtgtctgc tgctcacagg gcccggtact tctggggtaa cctacccgga atgaacaggc    5580
ccgtgatggc ttcaaagaat gataagctcg agctgcagga ctgcctggag ttcagtagga    5640
cagcaaagtt aaagaaagtg cagacaataa ccaccaagtc gaactccatc agacagggca    5700
aaaaccagct tttccctgta gtcatgaatg caaggacga cgttttgtgg tgcactgagc    5760
tcgaaaggat cttcggcttc cctgctcact acacggacgt gtccaacatg ggccgcggcg    5820
cccgtcagaa gctgctgggc aggtcctgga gtgtaccggt catcagacac ctgtttgccc    5880
ccttgaagga ctactttgcc tgtgaatagg cggccgcgac tctagatcat aatcagccat    5940
accacatttg tagaggtttt acttgcttta aaaaacctcc cacacctccc cctgaacctg    6000
aaacataaaa tgaatgcaat tgttgttgtt aacttgttta ttgcagctta taatggttac    6060
aaataaagca atagcatcac aaatttcaca aataaagcat ttttttcact gcattctagt    6120
tgtggtttgt ccaaactcat caatgtatct taaggcgtaa attgtaagcg ttaatatttt    6180
```

```
gttaaaattc gcgttaaatt tttgttaaat cagctcattt tttaaccaat aggccgaaat    6240
cggcaaaatc ccttataaat caaaagaata gaccgagata gggttgagtg ttgttccagt    6300
ttggaacaag agtccactat taaagaacgt ggactccaac gtcaaagggc gaaaaaccgt    6360
ctatcagggc gatggcccac tacgtgaacc atcaccctaa tcaagttttt tggggtcgag    6420
gtgccgtaaa gcactaaatc ggaaccctaa agggagcccc cgatttagag cttgacgggg    6480
aaagccggcg aacgtggcga aaaggaagg gaagaaagcg aaaggagcgg cgctagggc     6540 gctggcaagt gtagcggtca cgctgcgcgt aaccaccaca cccgccgcgc ttaatgcgcc    6600
gctacagggc gcgtcaggtg gcacttttcg gggaaatgtg cgcggaaccc ctatttgttt    6660 attttttctaa atacattcaa atatgtatcc gctcatgaga caataaccct gataaatgct    6720
tcaataatat tgaaaaagga agagtcctga ggcggaaaga accagctgtg gaatgtgtgt    6780
cagttagggt gtggaaagtc cccaggctcc ccagcaggca gaagtatgca aagcatgcat    6840
ctcaattagt cagcaaccag gtgtggaaag tccccaggct ccccagcagg cagaagtatg    6900
caaagcatgc atctcaatta gtcagcaacc atagtcccgc ccctaactcc gcccatcccg    6960
cccctaactc cgcccagttc cgcccattct ccgccccatg ctgactaat ttttttt att     7020 tatgcagagg ccgaggccgc ctcggcctct gagctattcc agaagtagtg aggaggcttt    7080
tttggaggcc taggcttttg caaagatcga tcaagagaca ggatgaggat cgtttcgcat    7140
gattgaacaa gatggattgc acgcaggttc tccggccgct tgggtggaga ggctattcgg    7200
ctatgactgg gcacaacaga caatcggctg ctctgatgcc gccgtgttcc ggctgtcagc    7260
gcaggggcgc ccggttcttt ttgtcaagac cgacctgtcc ggtgccctga atgaactgca    7320
agacgaggca gcgcggctat cgtggctggc cacgacgggc gttccttgcg cagctgtgct    7380
cgacgttgtc actgaagcgg gaagggactg gctgctattg ggcgaagtgc cggggcagga    7440
tctcctgtca tctcaccttg ctcctgccga gaaagtatcc atcatggctg atgcaatgcg    7500
gcggctgcat acgcttgatc cggctacctg cccattcgac caccaagcga aacatcgcat    7560
cgagcgagca cgtactcgga tggaagccgg tcttgtcgat caggatgatc tggacgaaga    7620
gcatcagggg ctcgcgccag ccgaactgtt cgccaggctc aaggcgagca tgcccgacgg    7680
cgaggatctc gtcgtgaccc atggcgatgc ctgcttgccg aatatcatgg tggaaaatgg    7740
ccgcttttct ggattcatcg actgtggccg ctgggtgtg gcggaccgct atcaggacat    7800
agcgttggct acccgtgata ttgctgaaga gcttggcggc gaatgggctg accgcttcct    7860
cgtgctttac ggtatcgccg ctcccgattc gcagcgcatc gccttctatc gccttcttga    7920
cgagttcttc tgagcgggac tctggggttc gaaatgaccg accaagcgac gcccaacctg    7980
ccatcacgag atttcgattc caccgccgcc ttctatgaaa ggttgggctt cggaatcgtt    8040
ttccgggacg ccggctggat gatcctccag cgcgggatc tcatgctgga gttcttcgcc     8100
caccctaggg ggaggctaac tgaaacacgg aaggagacaa taccggaagg aacccgcgct    8160
atgacggcaa taaaaagaca gaataaaacg cacggtgttg ggtcgtttgt tcataaacgc    8220
ggggttcggt cccagggctg gcactctgtc gatacccca cgagaccca ttggggccaa     8280 tacgcccgcg tttcttcctt ttccccaccc caccccccaa gttcgggtga aggcccaggg    8340
ctcgcagcca acgtcgggc ggcaggccct gccatagcct caggttactc atatatactt     8400
tagattgatt taaaacttca ttttttaattt aaaaggatct aggtgaagat ccttttttgat    8460 aatctcatga ccaaaatccc ttaacgtgag ttttcgttcc actgagcgtc agaccccgta    8520
gaaaagatca aaggatcttc ttgagatcct ttttttctgc gcgtaatctg ctgcttgcaa    8580
```

```
acaaaaaaac caccgctacc agcggtggtt tgtttgccgg atcaagagct accaactctt    8640
tttccgaagg taactggctt cagcagagcg cagataccaa atactgtcct tctagtgtag    8700
ccgtagttag gccaccactt caagaactct gtagcaccgc ctacatacct cgctctgcta    8760
atcctgttac cagtggctgc tgccagtggc gataagtcgt gtcttaccgg gttggactca    8820
agacgatagt taccggataa ggcgcagcgg tcgggctgaa cggggggttc gtgcacacag    8880
cccagcttgg agcgaacgac ctacaccgaa ctgagatacc tacagcgtga gctatgagaa    8940
agcgccacgc ttcccgaagg gagaaaggcg gacaggtatc cggtaagcgg cagggtcgga    9000
acaggagagc gcacgaggga gcttccaggg ggaaacgcct ggtatcttta tagtcctgtc    9060
gggtttcgcc acctctgact tgagcgtcga ttttttgtgat gctcgtcagg ggggcggagc    9120
ctatggaaaa acgccagcaa cgcggccttt ttacggttcc tggccttttg ctggccttt    9180 gctcacatgt tctttcctgc gttatcccct gattctgtgg ataaccgtat taccgccatg    9240
cat                                                                  9243

<210> SEQ ID NO 42
<211> LENGTH: 9264
<212> TYPE: DNA
<213> ORGANISM: Artificial Sequence
<220> FEATURE:
<223> OTHER INFORMATION: pCAG-scFvGCN4sfGFPDnmt3bFNLS

<400> SEQUENCE: 42
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggac tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catgggtcga ggtgagcccc acgttctgct tcactctccc catctccccc ccctccccac     420
ccccaatttt gtatttattt attttttaat tattttgtgc agcgatgggg gcggggggg      480 ggggggcgcg cgccaggcgg ggcggggcgg ggcgaggggc ggggcggggc gaggcggaga     540
ggtgcggcgg cagccaatca gagcggcgcg ctccgaaagt ttcctttat ggcgaggcgg     600 cggcggcggc ggccctataa aaagcgaagc gcgcggcggg cgggagtcgc tgcgttgcct     660
tcgccccgtg ccccgctccg cgccgcctcg cgccgcccgc cccggctctg actgaccgcg     720
ttactcccac aggtgagcgg gcgggacggc ccttctcctc cgggctgtaa ttagcgcttg     780
gtttaatgac ggctcgtttc ttttctgtgg ctgcgtgaaa gccttaaagg ctccggagg     840 ggccctttgt gcgggggga gcggctcggg gggtgcgtgc gtgtgtgtgt gcgtggggag     900
cgccgcgtgc ggcccgcgct gcccggccgg tgtgagcgct gcgggcgcgg cgcggggctt     960
tgtgcgctcc gcgtgtgcgc gaggggagcg cggccggggg cggtgccccg cggtgcgggg    1020
gggctgcgag gggaacaaag gctgcgtgcg gggtgtgtgc gtgggggggt gagcagggg     1080 tgtgggcgcg gcgtcgggc tgtaaccccc ccctgcaccc ccctccccga gttgctgagc    1140
acggcccggc ttcgggtgcg gggctccgtg cggggcgtgg cgcggggctc gccgtgccgg    1200 gcgggggtg gcggcaggtg ggggtgccgg cggggcggg gccgcctcgg gccggggagg    1260
gctcggggga ggggcgcggc ggccccggag cgccggcggc tgtcgaggcg cggcgagccg    1320
```

```
cagccattgc cttttatggt aatcgtgcga gagggcgcag ggacttcctt tgtcccaaat    1380
ctggcggagc cgaaatctgg gaggcgccgc cgcaccccct ctagcgggcg cgggcgaagc    1440
ggtgcggcgc cggcaggaag gaaatgggcg gggagggcct tcgtgcgtcg ccgcgccgcc    1500
gtccccttct ccatctccag cctcggggct gccgcagggg gacggctgcc ttcggggggg    1560
acggggcagg gcggggttcg gcttctggcg tgtgaccggc ggctctagag cctctgctaa    1620
ccatgttcat gccttcttct ttttcctaca gctcctgggc aacgtgctgg ttgttgtgct    1680
gtctcatcat tttggcaaag aattctgcag tcgacggtac catgggcccc gacatcgtga    1740
tgacccagag ccccagcagc ctgagcgcca gcgtgggcga ccgcgtgacc atcacctgcc    1800
gcagcagcac cggcgccgtg accaccagca actacgccag ctgggtgcag gagaagcccg    1860
gcaagctgtt caagggcctg atcggcggca ccaacaaccg cgcccccggc gtgcccagcc    1920
gcttcagcgg cagcctgatc ggcgacaagg ccaccctgac catcagcagc ctgcagcccg    1980
aggacttcgc cacctacttc tgcgccctgt ggtacagcaa ccactgggtg ttcggccagg    2040
gcaccaaggt ggagctgaag cgcggcggcg gcggcagcgg cggcggcggc agcggcggcg    2100
gcggcagcag cggcggcggc agcgaggtga gctgctggga gagcggcggc ggcctggtgc    2160
agcccggcgg cagcctgaag ctgagctgcg ccgtgagcgg cttcagcctg accgactacg    2220
gcgtgaactg ggtgcgccag gcccccggcc gcggcctgga gtggatcggc gtgatctggg    2280
gcgacggcat caccgactac aacagcgccc tgaaggaccg cttcatcatc agcaaggaca    2340
acggcaagaa caccgtgtac ctgcagatga gcaaggtgcg cagcgacgac accgccctgt    2400
actactgcgt gaccggcctg ttcgactact ggggccaggg caccctggtg accgtgagca    2460 gctaccccata cgatgttcca gattacgctg gtggaggcgg aggttctggg ggaggaggta    2520
gtggcggtgg tggttcagga ggcggcggaa gcttggatcc aggtgaggt ggaagcggta    2580 gcaaaggaga agaactttc actggagttg tcccaattct tgttgaatta gatggtgatg    2640
ttaatgggca caattttct gtccgtggag agggtgaagg tgatgctaca aacggaaaac    2700
tcacccttaa atttatttgc actactggaa aactacctgt tccgtggcca cacttgtca    2760 ctactctgac ctatggtgtt caatgctttt cccgttatcc ggatcacatg aaacggcatg    2820 acttttcaa gagtgccatg cccgaaggtt atgtacagga acgcactata tctttcaaag    2880
atgacgggac ctacaagacg cgtgctgaag tcaagtttga aggtgatacc cttgttaatc    2940
gtatcgagtt aaagggtatt gattttaaag aagatggaaa cattcttgga cacaaactcg    3000
agtacaactt taactcacac aatgtataca tcacggcaga caaacaaaag aatggaatca    3060
aagctaactt caaaattcgc cacaacgttg aagatggttc cgttcaacta gcagaccatt    3120
atcaacaaaa tactccaatt ggcgatggcc ctgtcctttt accagacaac cattacctgt    3180
cgacacaatc tgtcctttcg aaagatccca acgaaaagcg tgaccacatg gtccttcttg    3240
agtttgtaac tgctgctggg attacacatg gcatggatga actctacaaa ggtgaggtc    3300 ggaccggtgg cggtggcgga ggggctagca tgaagggaga cagcagacat ctgaatgaag    3360
aagagggtgc cagcgggtat gaggagtgca ttatcgttaa tgggaacttc agtgaccagt    3420
cctcagacac gaaggatgct ccctcacccc cagtcttgga ggcaatctgc acagagccag    3480
tctgcacacc agagaccaga ggccgcaggt caagctcccg gctgtctaag agggaggtct    3540
ccagccttct gaattacacg caggacatga caggagatgg agacagagat gatgaagtag    3600
atgatgggaa tggctctgat attctaatgc caaagctcac ccgtgagacc aaggacacca    3660
ggacgcgctc tgaaagcccg gctgtccgaa cccgacatag caatgggacc tccagcttgg    3720
```

```
agaggcaaag agcctccccc agaatcaccc gaggtcggca gggccgccac catgtgcagg   3780
agtaccctgt ggagtttccg gctaccaggt ctcggagacg tcgagcatca tcttcagcaa   3840
gcacgccatg gtcatcccct gccagcgtcg acttcatgga agaagtgaca cctaagagcg   3900
tcagtacccc atcagttgac ttgagccagg atggagatca ggagggtatg gataccacac   3960
aggtggatgc agagagcaga gatggagaca gcacagagta tcaggatgat aaagagtttg   4020
gaataggtga cctcgtgtgg ggaaagatca agggcttctc ctggtggcct gccatggtgg   4080
tgtcctggaa agccacctcc aagcgacagg ccatgcccgg aatgcgctgg gtacagtggt   4140
ttggtgatgg caagttttct gagatctctg ctgacaaact ggtggctctg ggctgttca    4200
gccagcactt taatctggct accttcaata agctggtttc ttataggaag gccatgtacc   4260
acactctgga gaaagccagg gttcgagctg caagaccttc tccagcagt cctggagagt    4320
cactggagga ccagctgaag cccatgctgg agtgggccca cggtggcttc aagcctactg   4380
ggatcgaggc cctcaaaccc aacaagaagc aaccagtggt taataagtcg aaggtgcgtc   4440
gttcagacag taggaactta gaacccagga gacgcgagaa caaaagtcga agacgcacaa   4500
ccaatgactc tgctgcttct gagtcccccc cacccaagcg cctcaagaca aatagctatg   4560
gcgggaagga ccgaggggag gatgaggaga gccgagaacg gatggcttct gaagtcacca   4620
acaacaaggg caatctggaa gaccgctgtt tgtcctgtgg aaagaagaac cctgtgtcct   4680
tccacccct ctttgagggt gggctctgtc agagttgccg ggatcgcttc ctagagctct    4740
tctacatgta tgatgaggac ggctatcagt cctactgcac cgtgtgctgt gagggccgtg   4800
aactgctgct gtgcagtaac acaagctgct gcagatgctt ctgtgtggag tgtctggagg   4860
tgctggtggg cgcaggcaca gctgaggatg ccaagctgca ggaaccctgg agctgctata   4920
tgtgcctccc tcagcgctgc catggggtcc tccgacgcag gaaagattgg aacatgcgcc   4980
tgcaagactt cttcactact gatcctgacc tggaagaatt tgagccaccc aagttgtacc   5040
cagcaattcc tgcagccaaa aggaggccca ttagagtcct gtctctgttt gatggaattg   5100
caacggggta cttggtgctc aaggagttgg gtattaaagt ggaaaagtac attgcctccg   5160
aagtctgtgc agagtccatc gctgtgggaa ctgttaagca tgaaggccag atcaaatatg   5220
tcaatgacgt ccggaaaatc accaagaaaa atattgaaga gtggggcccg ttcgacttgg   5280
tgattggtgg aagcccatgc aatgatctct ctaacgtcaa tcctgcccgc aaaggtttat   5340
atgagggcac aggaaggctc ttcttcgagt tttaccactt gctgaattat acccgcccca   5400
aggagggcga caaccgtcca ttcttctgga tgttcgagaa tgttgtggcc atgaaagtga   5460
atgacaagaa agacatctca agattcctgg catgtaaccc agtgatgatc gatgccatca   5520
aggtgtctgt tgctcacagg gcccggtact tctggggtaa cctacccgga atgaacaggc   5580
ccgtgatggc ttcaaagaat gataagctcg agctgcagga ctgcctggag ttcagtagga   5640
cagcaaagtt aaagaaagtg cagacaataa ccaccaagtc gaactccatc agacagggca   5700
aaaaccagct tttccctgta gtcatgaatg gcaaggacga cgttttgtgg tgcactgagc   5760
tcgaaaggat cttcggcttc cctgctcact acacggacgt gtccaacatg ggccgcggcg   5820
cccgtcagaa gctgctgggc aggtcctgga gtgtaccggt catcagacac ctgtttgccc   5880
ccttgaagga ctactttgcc tgtgaaccaa aaaagaagcg gaaagtctag gcggccgcga   5940
ctctagatca taatcagcca taccacattt gtagaggttt tacttgcttt aaaaaacctc   6000
ccacacctcc ccctgaacct gaaacataaa atgaatgcaa ttgttgttgt taacttgttt   6060
```

```
attgcagctt ataatggtta caaataaagc aatagcatca caaatttcac aaataaagca    6120
ttttttcac tgcattctag ttgtggtttg tccaaactca tcaatgtatc ttaaggcgta    6180
aattgtaagc gttaatattt tgttaaaatt cgcgttaaat ttttgttaaa tcagctcatt    6240
ttttaaccaa taggccgaaa tcggcaaaat cccttataaa tcaaaagaat agaccgagat    6300
agggttgagt gttgttccag tttggaacaa gagtccacta ttaaagaacg tggactccaa    6360
cgtcaaaggg cgaaaaaccg tctatcaggg cgatggccca ctacgtgaac catcacccta    6420
atcaagtttt tgggggtcga ggtgccgtaa agcactaaat cggaaccctca aagggagccc    6480
ccgatttaga gcttgacggg gaaagccggc gaacgtggcg agaaaggaag ggaagaaagc    6540
gaaaggagcg ggcgctaggg cgctggcaag tgtagcggtc acgctgcgcg taaccaccac    6600
acccgccgcg cttaatgcgc cgctacaggg cgcgtcaggt ggcactttc ggggaaatgt    6660
gcgcggaacc cctatttgtt tatttttcta aatacattca aatatgtatc cgctcatgag    6720
acaataaccc tgataaatgc ttcaataata ttgaaaaagg aagagtcctg aggcggaaag    6780
aaccagctgt ggaatgtgtg tcagttaggg tgtggaaagt ccccaggctc cccagcaggc    6840
agaagtatgc aaagcatgca tctcaattag tcagcaacca ggtgtggaaa gtccccaggc    6900
tcccagcag gcagaagtat gcaaagcatg catctcaatt agtcagcaac catagtcccg    6960
cccctaactc cgcccatccc gcccctaact ccgcccagtt ccgcccattc tccgccccat    7020
ggctgactaa ttttttttat ttatgcagag gccgaggccg cctcggcctc tgagctattc    7080
cagaagtagt gaggaggctt ttttggaggc ctaggctttt gcaaagatcg atcaagagac    7140
aggatgagga tcgtttcgca tgattgaaca agatggattg cacgcaggtt ctccggccgc    7200
ttgggtggag aggctattcg gctatgactg ggcacaacag acaatcggct gctctgatgc    7260
cgccgtgttc cggctgtcag cgcaggggcg cccggttctt tttgtcaaga ccgacctgtc    7320
cggtgccctg aatgaactgc aagacgaggc agcgcggcta tcgtggctgg ccacgacggg    7380
cgttccttgc gcagctgtgc tcgacgttgt cactgaagcg ggaagggact ggctgctatt    7440
gggcgaagtg ccggggcagg atctcctgtc atctcacctt gctcctgccg agaaagtatc    7500
catcatggct gatgcaatgc ggcggctgca tacgcttgat ccggctacct gcccattcga    7560
ccaccaagcg aaacatcgca tcgagcgagc acgtactcgg atggaagccg gtcttgtcga    7620
tcaggatgat ctggacgaag agcatcaggg gctcgcgcca gccgaactgt tcgccaggct    7680
caaggcgagc atgcccgacg gcgaggatct cgtcgtgacc catggcgatg cctgcttgcc    7740
gaatatcatg gtggaaaatg gccgcttttc tggattcatc gactgtggcc ggctgggtgt    7800
ggcggaccgc tatcaggaca tagcgttggc tacccgtgat attgctgaag agcttggcgg    7860
cgaatgggct gaccgcttcc tcgtgcttta cggtatcgcc gctcccgatt cgcagcgcat    7920
cgccttctat cgccttcttg acgagttctt ctgagcggga ctctggggtt cgaaatgacc    7980
gaccaagcga cgcccaacct gccatcacga gatttcgatt ccaccgccgc cttctatgaa    8040
aggttgggct tcggaatcgt tttccgggac gccggctgga tgatcctcca gcgcgggat    8100
ctcatgctgg agttcttcgc ccaccctagg gggaggctaa ctgaaacacg gaaggagaca    8160
ataccggaag gaacccgcgc tatgacggca ataaaaagac agaataaaac gcacggtgtt    8220
gggtcgtttg ttcataaacg cggggttcgg tcccagggct ggcactctgt cgatacccca    8280
ccgagacccc attggggcca atacgcccgc gtttcttcct tttccccacc caccccccca    8340
agttcgggtg aaggcccagg gctcgcagcc aacgtcgggg cggcaggccc tgccatagcc    8400
tcaggttact catatatact ttagattgat ttaaaacttc atttttaatt taaaaggatc    8460
```

```
taggtgaaga tccttttga taatctcatg accaaaatcc cttaacgtga gttttcgttc    8520
cactgagcgt cagaccccgt agaaaagatc aaaggatctt cttgagatcc ttttttctg    8580 cgcgtaatct gctgcttgca acaaaaaaaa ccaccgctac cagcggtggt ttgtttgccg    8640
gatcaagagc taccaactct ttttccgaag gtaactggct tcagcagagc gcagatacca    8700
aatactgtcc ttctagtgta gccgtagtta ggccaccact tcaagaactc tgtagcaccg    8760
cctacatacc tcgctctgct aatcctgtta ccagtggctg ctgccagtgg cgataagtcg    8820
tgtcttaccg ggttggactc aagacgatag ttaccggata aggcgcagcg gtcgggctga    8880
acggggggtt cgtgcacaca gcccagcttg gagcgaacga cctacaccga actgagatac    8940
ctacagcgtg agctatgaga aagcgccacg cttcccgaag ggagaaaggc ggacaggtat    9000
ccggtaagcg gcagggtcgg aacaggagag cgcacgaggg agcttccagg gggaaacgcc    9060
tggtatcttt atagtcctgt cgggtttcgc cacctctgac ttgagcgtcg attttgtga     9120 tgctcgtcag gggggcggag cctatggaaa aacgccagca acgcggcctt tttacggttc    9180
ctggcctttt gctggccttt tgctcacatg ttctttcctg cgttatcccc tgattctgtg    9240
gataaccgta ttaccgccat gcat                                          9264

<210> SEQ ID NO 43
<211> LENGTH: 9264
<212> TYPE: DNA
<213> ORGANISM: Artificial Sequence
<220> FEATURE:
<223> OTHER INFORMATION: pCAG-scFvGCN4sfGFPDnmt3bS1

<400> SEQUENCE: 43
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggac tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catgggtcga ggtgagcccc acgttctgct tcactctccc catctccccc cctccccac      420 ccccaattt gtatttattt atttttaat tattttgtgc agcgatgggg gcggggggg        480 gggggcgcg cgccaggcgg ggcggggcgg ggcgaggggc ggggcgggc gaggcggaga       540 ggtgcggcgg cagccaatca gagcggcgcg ctccgaaagt ttccttttat ggcgaggcgg     600
cggcggcggc ggccctataa aaagcgaagc gcgcggcggg cgggagtcgc tgcgttgcct     660
tcgccccgtg cccgctccg cgccgcctcg cgccgcccgc cccggctctg actgaccgcg      720
ttactcccac aggtgagcgg gcgggacggc ccttctcctc cgggctgtaa ttagcgcttg     780
gtttaatgac ggctcgtttc ttttctgtgg ctgcgtgaaa gccttaaagg gctccggag      840 ggccctttgt gcgggggga gcggctcggg gggtgcgtgc gtgtgtgtgt gcgtggggag      900
cgccgcgtgc ggcccgcgct gcccggcggc tgtgagcgct gcgggcgcgg cgcggggctt     960
tgtgcgctcc gcgtgtgcgc gaggggagcg cggccggggc ggtgccccg cggtgcgggg     1020 gggctgcgag gggaacaaag gctgcgtgcg gggtgtgtgc gtgggggggt gagcagggg      1080 tgtgggcgcg gcgtcgggc tgtaaccccc cctgcacccc cctccccga gttgctgagc      1140 acggcccggc ttcgggtgcg gggctccgtg cggggcgtgg cgcggggctc gccgtgccgg    1200
```

```
gcgggggtg  gcggcaggtg  ggggtgccgg  gcggggcggg  gccgcctcgg  gccggggagg   1260
gctcggggga  ggggcgcggc  ggccccggag  cgccggcggc  tgtcgaggcg  cggcgagccg   1320
cagccattgc  cttttatggt  aatcgtgcga  gagggcgcag  ggacttcctt  tgtcccaaat   1380
ctggcggagc  cgaaatctgg  gaggcgccgc  cgcacccccct ctagcgggcg  cgggcgaagc   1440
ggtgcggcgc  cggcaggaag  gaaatgggcg  gggagggcct  tcgtgcgtcg  ccgcgccgcc   1500
gtccccttct  ccatctccag  cctcggggct  gccgcagggg  gacggctgcc  ttcgggggg    1560
acggggcagg  gcggggttcg  gcttctggcg  tgtgaccggc  ggctctagag  cctctgctaa   1620
ccatgttcat  gccttcttct  ttttcctaca  gctcctgggc  aacgtgctgg  ttgttgtgct   1680
gtctcatcat  tttggcaaag  aattctgcag  tcgacggtac  catgggcccc  gacatcgtga   1740
tgacccagag  ccccagcagc  ctgagcgcca  gcgtgggcga  ccgcgtgacc  atcacctgcc   1800
gcagcagcac  cggcgccgtg  accaccagca  actacgccag  ctgggtgcag  agaagcccg    1860
gcaagctgtt  caagggcctg  atcgcggca  ccaacaaccg  cgcccccggc  gtgcccagcc    1920
gcttcagcgg  cagcctgatc  ggcgacaagg  ccaccctgac  catcagcagc  ctgcagcccg   1980
aggacttcgc  cacctacttc  tgcgccctgt  ggtacagcaa  ccactgggtg  ttcggccagg   2040
gcaccaaggt  ggagctgaag  cgcggcggcg  gcggcagcgg  cggcggcggc  agcggcggcg   2100
gcggcagcag  cggcggcggc  agcgaggtga  agctgctgga  gagcggcggc  ggcctggtgc   2160
agcccggcgg  cagcctgaag  ctgagctgcg  ccgtgagcgg  cttcagcctg  accgactacg   2220
gcgtgaactg  ggtgcgccag  gcccccggcc  gcggcctgga  gtggatcggc  gtgatctggg   2280
gcgacggcat  caccgactac  aacagcgccc  tgaaggaccg  cttcatcatc  agcaaggaca   2340
acggcaagaa  caccgtgtac  ctgcagatga  gcaaggtgcg  cagcgacgac  accgccctgt   2400
actactgcgt  gaccggcctg  ttcgactact  ggggccaggg  caccctggtg  accgtgagca   2460
gctacccata  cgatgttcca  gattacgctg  gtggaggcgg  aggttctggg  ggaggaggta   2520
gtggcggtgg  tggttcagga  ggcggcggaa  gcttggatcc  aggtgaggt  ggaagcggta    2580
gcaaaggaga  agaacttttc  actggagttg  tcccaattct  tgttgaatta  gatggtgatg   2640
ttaatgggca  caattttct   gtccgtggag  agggtgaagg  tgatgctaca  aacgaaaaac   2700
tcacccttaa  atttatttgc  actactggaa  aactacctgt  tccgtggcca  acacttgtca   2760
ctactctgac  ctatggtgtt  caatgctttt  cccgttatcc  ggatcacatg  aaacggcatg   2820
acttttcaa   gagtgccatg  cccgaaggtt  atgtacagga  acgcactata  tctttcaaag   2880
atgacgggac  ctacaagacg  cgtgctgaag  tcaagtttga  aggtgatacc  cttgttaatc   2940
gtatcgagtt  aaagggtatt  gattttaaag  aagatggaaa  cattcttgga  cacaaactcg   3000
agtacaactt  taactcacac  aatgtataca  tcacggcaga  caaacaaaag  aatggaatca   3060
aagctaactt  caaaattcgc  cacaacgttg  aagatggttc  cgttcaacta  gcagaccatt   3120
atcaacaaaa  tactccaatt  ggcgatggcc  ctgtcctttt  accagacaac  cattacctgt   3180
cgacacaatc  tgtcctttcg  aaagatccca  acgaaaagcg  tgaccacatg  gtccttcttg   3240
agtttgtaac  tgctgctggg  attacacatg  gcatggatga  gctctacaaa  ggtggaggtc   3300
ggaccggtgg  cggtggcgga  ggggctagca  tgaaggagga  cagcagacat  ctgaatgaag   3360
aagagggtgc  cagcgggtat  gaggagtgca  ttatcgttaa  tgggaacttc  agtgaccagt   3420
cctcagacac  gaaggatgct  ccctcacccc  cagtcttgga  ggcaatctgc  acagagccag   3480
tctgcacacc  agagaccaga  ggccgcaggt  caagctcccg  gctgtctaag  agggaggtct   3540
ccagccttct  gaattacacg  caggacatga  caggagatgg  agacagagat  gatgaagtag   3600
```

```
atgatgggaa tggctctgat attctaatgc caaagctcac ccgtgagacc aaggacacca   3660
ggacgcgctc tgaaagcccg gctgtccgaa cccgacatag caatgggacc tccagcttgg   3720
agaggcaaag agcctccccc agaatcaccc gaggtcggca gggccgccac catgtgcagg   3780
agtaccctgt ggagtttccg gctaccaggt ctcggagacg tcgagcatca tcttcagcaa   3840
gcacgccatg gtcatcccct gccagcgtcg acttcatgga agaagtgaca cctaagagcg   3900
tcagtacccc atcagttgac ttgagccagg atggagatca ggagggtatg gataccacac   3960
aggtggatgc agagagcaga gatggagaca gcacagagta tcaggatgat aaagagtttg   4020
gaataggtga cctcgtgtgg ggaaagatca agggcttctc ctggtggcct gccatggtgg   4080
tgtcctggaa agccacctcc aagcgacagg ccatgcccgg aatgcgctgg gtacagtggt   4140
ttggtgatgg caagttttct gagatctctg ctgacaaact ggtggctctg gggctgttca   4200
gccagcactt taatctggct accttcaata agctggtttc ttataggaag gccatgtacc   4260
acactctgga gaaagccagg gttcgagctg gcaagacctt ctccagcagt cctggagagt   4320
cactggagga ccagctgaag cccatgctgg agtgggccca cggtggcttc aagcctactg   4380
ggatcgaggc cctcaaaccc aacaagaagc aaccagtggt taataagtcg aaggtgcgtc   4440
gttcagacag taggaactta gaacccagga gacgcgagaa caaaagtcga agacgcacaa   4500
ccaatgactc tgctgcttct gagtcccccc cacccaagcg cctcaagaca aatagctatg   4560
gcgggaagga ccgaggggag gatgaggaga gccgagaacg gatggcttct gaagtcacca   4620
acaacaaggg caatctggaa gaccgctgtt tgtcctgtgg aaagaagaac cctgtgtcct   4680 tccacccct ctttgagggt gggctctgtc agagttgccg ggatcgcttc ctagagctct   4740
tctacatgta tgatgaggac ggctatcagt cctactgcac cgtgtgctgt gagggccgtg   4800
aactgctgct gtgcagtaac acaagctgct gcagatgctt ctgtgtggag tgtctggagg   4860
tgctggtggg cgcaggcaca gctgaggatg ccaagctgca ggaaccctgg agctgctata   4920
tgtgcctccc tcagcgctgc catggggtcc tccgacgcag gaaagattgg aacatgcgcc   4980
tgcaagactt cttcactact gatcctgacc tggaagaatt tgagccaccc aagttgtacc   5040
cagcaattcc tgcagccaaa aggaggccca ttagagtcct gtctctgttt gatggaattg   5100
caacggggta cttggtgctc aaggagttgg gtattaaagt ggaaaagtac attgcctccg   5160
aagtctgtgc agagtccatc gctgtgggaa ctgttaagca tgaaggccag atcaaatatg   5220
tcaatgacgt ccggaaaatc accaagaaaa atattgaaga gtggggcccg ttcgacttgg   5280
tgattggtgg aagcccatgc aatgatctct ctagagtcaa tcctgcccgc aaaggtttat   5340
atgagggcac aggaaggctc ttcttcgagt tttaccactt gctgaattat acccgcccca   5400
aggagggcga caaccgtcca ttcttctgga tgttcgagaa tgttgtggcc atgaaagtga   5460
atgacaagaa agacatctca agattcctgg catgtaaccc agtgatgatc gatgccatca   5520
aggtgtctgc tgctcacagg gcccggtact tctgggtaa cctacccgga atgaacaggc   5580
ccgtgatggc ttcaaagaat gataagctcg agctgcagga ctgcctggag ttcagtagga   5640
cagcaaagtt aaagaaagtg cagacaataa ccaccaagtc gaactccatc agacagggca   5700
aaaaccagct tttccctgta gtcatgaatg caaggacga cgttttgtgg tgcactgagc   5760
tcgaaaggat cttcggcttc cctgctcact acacggacgt gtccaacatg ggccgcggcg   5820
cccgtcagaa gctgctgggc aggtcctgga gtgtaccggt catcagacac ctgtttgccc   5880
ccttgaagga ctactttgcc tgtgaaccaa aaaagaagcg gaaagtctag gcggccgcga   5940
```

```
ctctagatca taatcagcca taccacattt gtagaggttt tacttgcttt aaaaaacctc    6000
ccacacctcc ccctgaacct gaaacataaa atgaatgcaa ttgttgttgt taacttgttt    6060
attgcagctt ataatggtta caaataaagc aatagcatca caaatttcac aaataaagca    6120 ttttttcac tgcattctag ttgtggtttg tccaaactca tcaatgtatc ttaaggcgta     6180
aattgtaagc gttaatattt tgttaaaatt cgcgttaaat ttttgttaaa tcagctcatt    6240
ttttaaccaa taggccgaaa tcggcaaaat cccttataaa tcaaaagaat agaccgagat    6300
agggttgagt gttgttccag tttggaacaa gagtccacta ttaaagaacg tggactccaa    6360
cgtcaaaggg cgaaaaaccg tctatcaggg cgatggccca ctacgtgaac catcacccta    6420
atcaagtttt tggggtcga ggtgccgtaa agcactaaat cggaaccta aagggagccc      6480 ccgatttaga gcttgacggg gaaagccggc gaacgtggcg agaaaggaag ggaagaaagc    6540
gaaaggagcg ggcgctaggg cgctggcaag tgtagcggtc acgctgcgcg taaccaccac    6600
acccgccgcg cttaatgcgc cgctacaggg cgcgtcaggt ggcactttc ggggaaatgt     6660 gcgcggaacc cctatttgtt tattttcta aatacattca aatatgtatc cgctcatgag     6720
acaataaccc tgataaatgc ttcaataata ttgaaaaagg aagagtcctg aggcggaaag    6780
aaccagctgt ggaatgtgtg tcagttaggg tgtggaaagt ccccaggctc cccagcaggc    6840
agaagtatgc aaagcatgca tctcaattag tcagcaacca ggtgtggaaa gtccccaggc    6900
tccccagcag gcagaagtat gcaaagcatg catctcaatt agtcagcaac catagtcccg    6960
cccctaactc cgcccatccc gcccctaact ccgcccagtt ccgcccattc tccgccccat    7020
ggctgactaa ttttttttat ttatgcagag gccgaggccg cctcggcctc tgagctattc    7080
cagaagtagt gaggaggctt ttttggaggc ctaggctttt gcaaagatcg atcaagagac    7140
aggatgagga tcgtttcgca tgattgaaca agatggattg cacgcaggtt ctccggccgc    7200
ttgggtggag aggctattcg gctatgactg ggcacaacag acaatcggct gctctgatgc    7260
cgccgtgttc cggctgtcag cgcaggggcg cccggttctt tttgtcaaga ccgacctgtc    7320
cggtgccctg aatgaactgc aagacgaggc agcgcggcta tcgtggctgg ccacgacggg    7380
cgttccttgc gcagctgtgc tcgacgttgt cactgaagcg ggaagggact ggctgctatt    7440
gggcgaagtg ccggggcagg atctcctgtc atctcacctt gctcctgccg agaaagtatc    7500
catcatggct gatgcaatgc ggcggctgca tacgcttgat ccggctacct gcccattcga    7560
ccaccaagcg aaacatcgca tcgagcgagc acgtactcgg atggaagccg gtcttgtcga    7620
tcaggatgat ctggacgaag agcatcaggg gctcgcgcca gccgaactgt tcgccaggct    7680
caaggcgagc atgcccgacg gcgaggatct cgtcgtgacc catggcgatg cctgcttgcc    7740
gaatatcatg gtggaaaatg gccgcttttc tggattcatc gactgtggcc ggctgggtgt    7800
ggcggaccgc tatcaggaca tagcgttggc tacccgtgat attgctgaag agcttggcgg    7860
cgaatgggct gaccgcttcc tcgtgcttta cggtatcgcc gctcccgatt cgcagcgcat    7920
cgccttctat cgccttcttg acgagttctt ctgagcggga ctctggggtt cgaaatgacc    7980
gaccaagcga cgcccaacct gccatcacga gatttcgatt ccaccgccgc cttctatgaa    8040
aggttgggct tcggaatcgt tttccgggac gccggctgga tgatcctcca gcgcggggat    8100
ctcatgctgg agttcttcgc ccaccctagg gggaggctaa ctgaaacacg gaaggagaca    8160
ataccggaag gaacccgcgc tatgacggca ataaaaagac agaataaaac gcacggtgtt    8220
gggtcgtttg ttcataaacg cggggttcgg tcccagggct ggcactctgt cgataccca     8280 ccgagacccc attggggcca atacgcccgc gtttcttcct tttccccacc ccaccccca    8340
```

```
agttcgggtg aaggcccagg gctcgcagcc aacgtcgggg cggcaggccc tgccatagcc    8400
tcaggttact catatatact ttagattgat ttaaaacttc atttttaatt taaaaggatc    8460
taggtgaaga tccttttga taatctcatg accaaaatcc cttaacgtga gttttcgttc     8520
cactgagcgt cagaccccgt agaaaagatc aaaggatctt cttgagatcc ttttttttctg   8580 cgcgtaatct gctgcttgca acaaaaaaaa ccaccgctac cagcggtggt ttgtttgccg    8640
gatcaagagc taccaactct ttttccgaag gtaactggct tcagcagagc gcagatacca    8700
aatactgtcc ttctagtgta gccgtagtta ggccaccact tcaagaactc tgtagcaccg    8760
cctacatacc tcgctctgct aatcctgtta ccagtggctg ctgccagtgg cgataagtcg    8820
tgtcttaccg ggttggactc aagacgatag ttaccggata aggcgcagcg gtcgggctga    8880 acgggggggtt cgtgcacaca gcccagcttg gagcgaacga cctacaccga actgagatac    8940
ctacagcgtg agctatgaga aagcgccacg cttcccgaag ggagaaaggc ggacaggtat    9000
ccggtaagcg gcagggtcgg aacaggagag cgcacgaggg agcttccagg gggaaacgcc    9060
tggtatcttt atagtcctgt cgggtttcgc cacctctgac ttgagcgtcg attttgtga    9120 tgctcgtcag gggggcggag cctatggaaa aacgccagca acgcggcctt tttacggttc    9180
ctggcctttt gctggccttt tgctcacatg ttctttcctg cgttatcccc tgattctgtg    9240
gataaccgta ttaccgccat gcat                                           9264
```

<210> SEQ ID NO 44
<211> LENGTH: 7
<212> TYPE: PRT
<213> ORGANISM: Artificial Sequence
<220> FEATURE:
<223> OTHER INFORMATION: tag peptide

<400> SEQUENCE: 44

Gly Val Lys Glu Ser Leu Val
1               5

<210> SEQ ID NO 45
<211> LENGTH: 5
<212> TYPE: PRT
<213> ORGANISM: Artificial Sequence
<220> FEATURE:
<223> OTHER INFORMATION: GS linker

<400> SEQUENCE: 45

Gly Ser Gly Ser Gly
1               5

<210> SEQ ID NO 46
<211> LENGTH: 22
<212> TYPE: PRT
<213> ORGANISM: Artificial Sequence
<220> FEATURE:
<223> OTHER INFORMATION: GS linker

<400> SEQUENCE: 46

Gly Ser Gly Ser Gly Gly Ser Gly Ser Gly Ser Gly Gly Ser Gly Ser
1               5                   10                  15

Gly Gly Ser Gly Ser Gly
            20

<210> SEQ ID NO 47
<211> LENGTH: 43
<212> TYPE: PRT

```
<213> ORGANISM: Artificial Sequence
<220> FEATURE:
<223> OTHER INFORMATION: GS linker

<400> SEQUENCE: 47

Gly Ser Gly Ser Gly Ser Gly Ser Gly Gly Ser Gly Ser Gly Gly
1               5                   10                  15

Ser Gly Ser Gly Gly Ser Gly Gly Ser Gly Ser Gly Gly Ser Gly Ser
            20                  25                  30

Gly Gly Ser Gly Ser Gly Gly Ser Gly Ser Gly
        35                  40
```

DNA METHYLATION EDITING KIT AND DNA METHYLATION EDITING METHOD

TECHNICAL FIELD

The present invention relates to a DNA methylation editing kit and a DNA methylation editing method.

BACKGROUND ART

The methylation of cytosine in genomic DNA is a typical modification of epigenetics (epigenome) regulating gene expression. Possible regulation of the methylation of a particular gene enables elucidation of epigenome diseases such as cancer, production of models of the diseases, and its application to epigenome treatment. Currently, treatment of cancer using the demethylation of the whole genome with 5-azacytosine or the like is put into practical use. However, the treatment affects all genes, and therefore, some doubt remains as to safety concerns. Therefore, development of a technology for regulating the methylation of a particular site has been desired.

As such a technology for regulating the methylation of a particular site, a technology for demethylating a particular gene by using a protein obtained by fusing TALEN and the catalytic domain of TET1 which is an enzyme involved in demethylation has been previously reported (Non Patent Literature 1). However, it was very time-consuming due to use of TALEN, which is a genome editing technology of the previous-generation, and the degree of demethylation has not been very high.

Examples of new-generation genome editing methods include a method of using CRISPR/Cas (Non Patent Literature 2). Although use and application of an array in which plural peptide epitopes are linked, and scFv which is a single-chain antibody for signal amplification have been reported (Non Patent Literature 3) as a CRISPR/Cas genome editing method, the method has not been known to be applied to regulation of DNA methylation.

CITATION LIST

Non Patent Literature

Non Patent Literature 1: Maeder M L et al. Nat Biotechnol, 31, 1137-1142, 2013
Non Patent Literature 2: JIKKEN IGAKU (YODOSHA CO., LTD.), July, 2014, pp. 1690-1714
Non Patent Literature 3: Tanenbaum M E et al. Cell 159, 635-646, 2014

SUMMARY OF INVENTION

Technical Problem

In view of the problems described above, an object of the present invention is to provide a DNA methylation editing kit and a DNA methylation editing method.

Solution to Problem

As a result of intensive study for solving the problems described above, the present inventors found that use of a CRISPR/Cas genome editing method enables the methylation of a particular site to be effectively regulated, and the present invention was thus accomplished.

In other words, the gist of the present invention is as follows.

[1] A DNA methylation editing kit comprising:
(1) a fusion protein of inactivated CRISPR-associated endonuclease Cas9 (dCas9) having no nuclease activity and a tag peptide array in which a plurality of tag peptides are linked by linkers, or an RNA or DNA coding therefor;
(2) a fusion protein(s) of a tag peptide-binding portion and a methylase or demethylase, or an RNA(s) or DNA(s) coding therefor; and
(3) a guide RNA(s) (gRNA(s)) comprising a sequence complementary to a DNA sequence within 1 kb of a desired site of methylation or demethylation, or a DNA(s) expressing the gRNA(s).

[2] The DNA methylation editing kit according to [1], wherein the demethylase is a catalytic domain (TET1CD) of ten-eleven translocation 1.

[3] The DNA methylation editing kit according to [1], wherein the methylase is DNA methyltransferase 3 beta (DNMT3B).

[4] The DNA methylation editing kit according to any one of [1] to [3], wherein the tag peptides are peptide epitopes, and the tag peptide-binding portion is an anti-peptide-epitope antibody.

[5] The DNA methylation editing kit according to [4], wherein the peptide epitopes are general control non-derepressible 4 (GCN4) peptide epitopes, and the anti-peptide-epitope antibody is an anti-GCN4 peptide epitope antibody.

[6] The DNA methylation editing kit according to [4], wherein the peptide epitopes are His tags or EE tags, and the anti-peptide-epitope antibody is an anti-His tag antibody or an anti-EE tag antibody.

[7] The DNA methylation editing kit according to any one of [4] to [6], wherein the antibody is a single-chain antibody (scFv).

[8] The DNA methylation editing kit according to any one of [1] to [3], wherein the tag peptides are a small fragment of a split protein, and the tag peptide-binding portion is a large fragment of the split protein.

[9] The DNA methylation editing kit according to [8], wherein the split protein is GFP.

[10] The DNA methylation editing kit according to any one of [1] to [3], wherein the tag peptides are GVKESLV, and the tag peptide-binding portion is PDZ protein.

[11] The DNA methylation editing kit according to any one of [1] to [10], wherein the linkers consist of 5 to 100 amino acids.

[12] The DNA methylation editing kit according to any one of [1] to [11], wherein the linkers consist of 5 to 50 amino acids.

[13] The DNA methylation editing kit according to any one of [1] to [12], wherein the linkers consist of 10 to 50 amino acids.

[14] The DNA methylation editing kit according to any one of [1] to [13], wherein the fusion proteins of the (1) and/or (2) further include a selection marker.

[15] The DNA methylation editing kit according to any one of [1] to [14], which contains plural gRNAs [16] The DNA methylation editing kit according to any one of [1] to [15], wherein all the DNAs of the (1) to (3) are contained in one vector.

[17] A DNA methylation editing method comprising transfecting a cell with the following (1) to (3):
(1) a fusion protein of inactivated CRISPR-associated endonuclease Cas9 (dCas9) having no nuclease activity and a tag peptide array in which a plurality of tag peptides are linked by linkers, or an RNA or DNA coding therefor;

(2) a fusion protein(s) of a tag peptide-binding portion and a methylase or demethylase, or an RNA(s) or DNA(s) coding therefor; and (3) a guide RNA(s) (gRNA(s)) comprising a sequence complementary to a DNA sequence within 1 kb of a desired site of methylation or demethylation, or a DNA(s) expressing the gRNA(s).

[18] The DNA methylation editing method according to [17], wherein the fusion proteins of the (1) and/or (2) further include a selection marker.

[19] The DNA methylation editing method according to [18], further comprising selecting and collecting a cell expressing the selection marker.

Advantageous Effects of Invention

According to the present invention, it is possible to regulate the DNA methylation of a particular site, for example, to demethylate a methylated site, and to methylate an unmethylated site.

DESCRIPTION OF EMBODIMENTS

Embodiments of the present invention will be described in detail below.

Figure 3A:
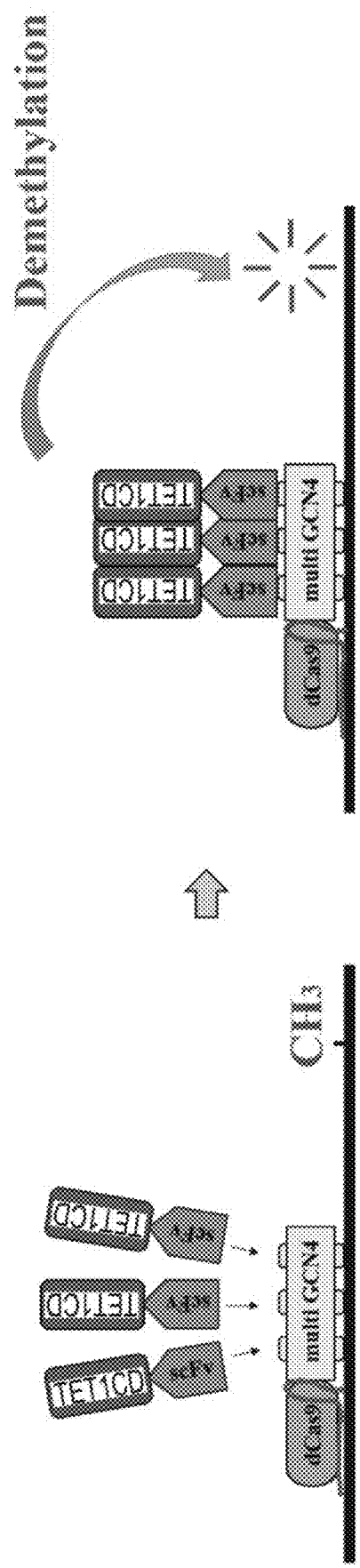
FIG. 3A is a view illustrating a scheme of demethylation amplification based on dCas9 and a repeating peptide array. Inactivated Cas9 (dCas9) fused with the repeating peptide array and having no nuclease activity can recruit plural pieces of scFv antibody-fused TET1CD. Therefore, the plural pieces of TET1CD can more effectively demethylate a target.

In CRISPR/Cas, Cas9, which is a DNA-cleaving enzyme, forms a complex with a short RNA (guide RNA (gRNA)) comprising an about-20-bp sequence complementary to a target, and cleaves DNA as a target (Non Patent Literature 2). In such a case, when a mutant enzyme having no DNA cleavage activity, referred to as dCas9, is used, only binding to a target can be achieved without cleaving the target. Thus, recruitment of factors that perform methylation and demethylation by linking various components to dCas9 enables the methylation of a particular gene to be regulated. When a system where dCas9 linked with a tag peptide array comprising plural tag peptides, and a tag peptide-binding portion such as a single-chain antibody (scFv) for a tag peptide fused with a factor performing methylation and demethylation are used, and plural methylation factors or demethylation factors can be recruited for one molecule of dCas9, and an ability to perform the methylation or demethylation can be enhanced (FIG. 3a).

In the present invention, first, a sequence (target sequence) complementary to a DNA sequence within 1 kb from a desired site of methylation or demethylation is produced, and a gRNA comprising the target sequence is produced. The gRNA has a property of forming a complex, with dCas9 having no nuclease activity.

When a fusion protein of dCas9 and a tag peptide array is produced, the gRNA forms a complex with the fusion protein, through dCas9, and therefore, a gRNA-dCas9-tag peptide array complex is formed. The gRNA is bound to a sequence complementary to a target sequence included in the gRNA, and therefore, the gRNA-dCas9-tag peptide array complex is bound to a DNA sequence within 1 kb from a desired site of methylation or demethylation. A fusion protein of a tag peptide-binding portion and a methylase or demethylase is recruited within 1 kb from the desired site of methylation or demethylation by binding of the tag peptide-binding portion to the tag peptide array. The recruited methylase or demethylase methylates or demethylates a site within 1 kb from its recruited portion (FIG. 3a).

(DNA Methylation Editing Kit and DNA Methylation Editing Method)

The present invention relates to a DNA methylation editing kit comprising: (1) a fusion protein of inactivated CRISPR-associated endonuclease Cas9 (dCas9) having no nuclease activity and a tag peptide array in which plural tag peptides such as GCN4 are linked by linkers, or an RNA or DNA coding therefor; (2) a fusion protein(s) of a tag peptide-binding portion such as an anti-tag peptide antibody and a methylase or demethylase, or an RNA(s) or DNA(s) coding therefor; and (3) a guide RNA(s) (gRNA(s)) comprising a sequence complementary to a DNA sequence within 1 kb from a desired site of demethylation, or a DNA(s) expressing the gRNA(s). In addition, the present invention relates to a DNA methylation editing method comprising transfecting a cell with the (1) to (3) described above.

The DNA methylation editing includes both of the methylation of a DNA unmethylated site and the demethylation of a DNA methylated site.

(Inactivated Cas9 Having No Nuclease Activity)

CRISPR-associated endonuclease Cas9 (Cas9) includes two lobes of a REC lobe (REC: recognition) and a NUC lobe (NUC: nuclease), in which the NUC lobe is a site responsible for nuclease activity (Non Patent Literature 2). Thus, inactivated Cas9 (dCas9) having no nuclease activity in the present invention can be produced by introducing a mutation into the NUC lobe of Cas9. As a result, the nuclease activity of Cas9 can be inactivated while maintaining the capacity of binding to a target site. A site in which the mutation is introduced into the NUC lobe is not limited as long as only the nuclease activity can be inactivated. For example, mutation of Asp10 to alanine (D10A), mutation of His840 to alanine (H840A), and mutation of Asn863 to alanine (N863A) in Cas9 (UniProtKB/Swiss-Prot: Q99ZW2) are preferred. Such mutations may be one kind or a combination of two or more kinds thereof.

DNAs encoding dCas9 can be produced by introducing mutations into DNAs encoding Cas9 that can be obtained from GenBank and the like. Alternatively, plasmids comprising commercially available dCas9 may be obtained from Addgene and the like and used, DNAs encoding dCas9 may be obtained by PCR with the plasmids as templates or may be artificially produced using an artificial gene synthesis technology known to those skilled in the art, and methods of obtaining the DNAs are not limited. RNAs encoding dCas9 may be obtained by known molecular biological techniques, of which any may be used. For example, such an RNA may be obtained by using a DNA encoding the dCas9 as a template and triggering an RNA polymerase.

(Tag Peptide Array)

The tag peptide array in the present invention refers to a tag peptide array in which plural tag peptides are linked by linkers.

The tag peptides can be optionally selected in combination with a tag peptide-binding portion described later. Examples of the combination of the tag peptides and the tag peptide-binding portion include a combination of a peptide epitope and an antibody recognizing the peptide epitope, and a combination of the small fragment and large fragment of a split protein.

Examples of the combination of a peptide epitope and an antibody recognizing the peptide epitope include: GCN4 and an anti-GCN4 antibody; a His tag and an anti-His tag antibody; an EE hexapeptide and an anti-EE hexapeptide antibody; a c-Myc tag and an anti-c-Myc tag antibody; an HA tag and an anti-HA tag antibody; an S tag and an anti-S tag antibody; and a FLAG tag and an anti-FLAG tag antibody (Protein Engineering, Design & Selection vol. 24 no. 5 pp. 419-428, 2011). Among them, a peptide included in GCN4 is preferably used, the amino acid sequence of GCN4 can be obtained from, for example, PDB, and the DNA sequence of GCN4 can be obtained from GenBank or the like. Those skilled in the art can also obtain an RNA sequence corresponding to the DNA sequence on the basis of information on the DNA sequence by using nucleotide sequence conversion software and the like. The GCN4 peptide epitope can be used without limitation as long as being an epitope in GCN4, and an amino acid sequence represented by SEQ ID NO: 1 is preferred. Information on the amino acid sequences of the other tag peptides and the nucleotide sequences encoding the amino acid sequences can be obtained from known databases and the like.

The split protein refers to a pair of proteins in which, in the case of dividing a certain protein into two portions, the two portions of the protein are reassociated, thereby enabling formation of the same structure as that of the original protein. Particularly in the case of dividing the original protein into the two portions, one portion as a short peptide (small fragment) may be used with a tag peptide, and the other longer portion (large fragment) may be used as a tag peptide-binding portion (Current Opinion in Chemical Biology 2011, 15: 789-797). A known split protein can be used as the split protein which can be used for such a purpose, and examples thereof include GFP (green fluorescent protein).

Further, binding of a peptide and a protein domain is compiled into a database, and a combination of a tag peptide and a tag peptide-binding portion can be found with reference to, for example, Peptide Binding Proteins Database. For example, since PDZAlpha-Syntrophin PDZ protein interaction domain can be bound to GVKESLV (SEQ ID NO: 44), GVKESLV can be used with a tag peptide, and the PDZ domain can be used as a tag peptide-binding portion.

Further, the binding strength of a pair of a peptide and a peptide binding portion can be increased by connecting another unrelated domain with a linker and performing domain interface evolution. Methylation can be further efficiently regulated by using such a pair (Proc. Natl. Acad. Sci. USA, 2008, vol. 105 no. 18, 6578-6583).

Linkers interposed in a tag peptide array comprising such plural tag peptides as described above include any sequence as long as the linkers do not inhibit binding of the peptides and peptide-binding portions or the desired effect of the present invention. Examples of the linkers include a repeating sequence of glycine and serine. The length of such a linker can be set as appropriate according to the kind of a methylase or demethylase and the like, and is preferably 5 to 100 amino acids, more preferably 5 to 50 amino acids, and still more preferably 10 to 50 amino acids. In the case of TET and DNMT described later, the length is more preferably 15 to 40 amino acids, still more preferably 17 to 30 amino acids, and most preferably 22 amino acids. When the length of the linker is 10 amino acids in the case of the repeating sequence of glycine (G) and serine (S), for example, the linker sequence may be GSGSG (SEQ ID NO: 45), GSGSGGSGSGSGGSGS GGSGSG (SEQ ID NO: 46), or GSGSGGSGSGGSGSGGSGSGGSGSGGSGSGGSG SGGSGSG (SEQ ID NO: 47).

The tag peptide array in the present invention refers to a tag peptide array in which assuming that a combination of a tag peptide and a linker is one unit, one or plural units are repeatedly linked. The plural units mean two or more units. The number of repeated units can be increased or decreased as appropriate depending on the distance between a target site and a methylated or demethylated site, the kind of a methylase or demethylase, and the like, and may be, for example, 3 to 5.

DNA encoding a tag peptide array can be produced by adding a DNA sequence encoding a desired linker to DNA encoding a tag peptide that can be obtained from GenBank or the like. A method of obtaining the DNA by a molecular biological technique based on information on a DNA sequence is known. For example, the DNA can be artificially produced using an artificial gene synthesis technology known to those skilled in the art, and the method of obtaining the DNA is not limited. Those skilled in the art can also obtain an RNA sequence corresponding to the DNA sequence on the basis of information on the DNA sequence by using nucleotide sequence conversion software and the like.

(Fusion Protein of dCas9 and Tag Peptide Array, or RNA or DNA Coding Therefor)

DNA encoding a fusion protein of dCas9 and a tag peptide array can be produced by binding of DNA encoding the dCas9 defined above and DNA encoding the tag peptide array by using an optional method including a well-known gene manipulation method, and is not particularly limited. A DNA sequence encoding a selection marker may also be inserted into the DNA encoding the fusion protein. The selection marker enables cells into which the DNA encoding the fusion protein is introduced to be selected by cell sorting or the like. Examples of the selection marker include, but are not limited to, genes encoding fluorescent proteins such as GFP, Ds-Red, and mCherry, and drug resistance genes such as puromycin resistance genes and neomycin resistance genes. The fusion protein or RNA encoding the fusion protein can be obtained by a known molecular biological technique using DNA encoding the fusion protein, and can be obtained by, for example, inserting DNA encoding the fusion protein into an appropriate expression vector and expressing the protein or the RNA.

(Tag Peptide-Binding Portion)

As the tag peptide-binding portion, an anti-tag peptide (peptide epitope) antibody, the large fragment of a split protein, or the like can be used depending on the kind of a tag peptide, as described above. The anti-tag peptide antibody means an antibody that specifically recognizes a tag peptide. The anti-tag peptide antibody includes polyclonal antibodies and monoclonal antibodies. The monoclonal antibodies include monoclonal antibodies, the fragments of monoclonal antibodies, $F(ab')_2$ antibodies, F(ab') antibodies, short-chain antibodies (scFv), diabodies, and minibodies. DNA encoding the anti-tag peptide antibody can be obtained by a known molecular biological technique, can be obtained by amplifying, for example, a commercially available plasmid such as Addgene plasmid 60904 by PCR, or may be artificially produced using an artificial gene synthesis technology known to those skilled in the art, and a method of obtaining the DNA is not limited. The anti-tag peptide antibody or RNA encoding the anti-tag peptide antibody can be obtained by inserting the DNA encoding the anti-tag peptide antibody into an appropriate expression vector and expressing the protein or the RNA.

(Methylase and Demethylase)

The methylase in the present invention can be used without limitation as long as being an enzyme that catalyzes the methylation of an unmethylated site, and includes a methylase which is an enzyme that methylates a particular base on a DNA nucleotide sequence, and a methyltransferase which is an enzyme transferring a methyl group to a particular base, and more specific examples thereof include DNA methyltransferase 3 beta (DNMT3B), DNA methyltransferase 3 alpha (DNMT3A), and DNA methyltransferase 1 (DNMT1). The demethylase in the present invention can be used without limitation as long as being an enzyme catalyzing a series of reaction leading to the demethylation of a methylation site, and includes ten-eleven translocation 1 (TET1), ten-eleven translocation 2 (TET2), ten-eleven translocation 3 (TET3), and thymine-DNA glycosylase (TDG). These enzymes may be a portion or the whole of an enzyme protein. Preferred examples of the portion of the enzyme protein include a catalytic domain of an enzyme. Information on the sequence of DNAs encoding the enzymes can be obtained from GenBank and the like, and the DNAs can be produced from the cDNAs of target animals such as human by PCR. Alternatively, the DNAs encoding the enzymes may be artificially produced using an artificial gene synthesis technology known to those skilled in the art, and methods of obtaining the DNAs are not limited. The enzymes or RNAs encoding the enzymes can be obtained by inserting the DNAs into an appropriate expression vector and expressing the proteins or RNAs.

(Fusion Protein of Tag Peptide-Binding Portion and Methylase or Demethylase, or RNA or DNA Encoding Fusion Protein)

DNA encoding a fusion protein of a tag peptide-binding portion such as an anti-peptide-epitope antibody and a methylase or demethylase can be produced by linking DNA encoding the tag peptide-binding portion defined above with DNA encoding a methylase or demethylase by using an optional method including a well-known gene manipulation method, and is not particularly limited. A DNA sequence encoding a selection marker may also be inserted into DNA encoding the fusion protein. The selection marker enables cells into which the DNA encoding the fusion protein is introduced to be selected by cell sorting or the like. Examples of the selection marker include, but are not limited to, genes encoding fluorescent proteins such as GFP, Ds-Red, and mCherry, and drug resistance genes such as puromycin resistance genes and neomycin resistance genes. When a DNA sequence encoding a selection marker is inserted into the DNA encoding the fusion protein of the dCas9 and the tag peptide array, a selection marker different from the selection marker may be inserted into DNA encoding a fusion protein of a tag peptide-binding portion and a methylase or demethylase. The fusion protein or RNA encoding the fusion protein can be obtained by a known molecular biological technique using DNA encoding the fusion protein, and can be obtained by, for example, inserting DNA encoding the fusion protein into an appropriate expression vector and expressing the protein or the RNA.

(Guide RNA (gRNA) or DNA Expressing Guide RNA)

The guide RNA (gRNA) in the present invention is a guide RNA in which a tracrRNA and a crRNA are artificially linked in a CRISPER/Cas method. By a known technique based on an RNA sequence described in Non Patent Literature 2 (p. 1698), DNA corresponding to the RNA sequence can be obtained as DNA expressing tracrRNA. For example, the DNA may be artificially produced using an artificial gene synthesis technology known to those skilled in the art, and a method of obtaining the DNA is not limited. Alternatively, a plasmid that enables a desired gRNA to be expressed by inserting a DNA sequence corresponding to an arbitrary crRNA is commercially available (Addgene plasmid 41824 or the like) and may be therefore used. A sequence complementary to a DNA sequence within 1 kb from a desired site of methylation or demethylation is used as the crRNA. One kind of the gRNA is acceptable, or plural gRNAs each comprising different crRNAs may be used.

(All-in-One Vector)

The DNAs encoding the two fusion proteins described above may be further linked, resulting in DNA encoding a fusion protein of dCas9, a tag peptide array, a tag peptide-binding portion, and a methylase or demethylase, which may be incorporated into a vector and may be used. The vector comprising the DNA is referred to as an all-in-one vector. A linker may be inserted as appropriate into the DNA encoding the fusion protein. For example, when a 2A peptide derived from a virus is inserted as a linker between a fusion protein (regarded as a component 1) of dCas9 and a tag peptide array and a fusion protein (regarded as a component 2) of a tag peptide-binding portion and a methylase or demethylase, the 2A peptide is cleaved by the 2A peptidase in a cell, and therefore, the components 1 and 2 are prevented from being linked and expressed as two separated proteins. The all-in-one vector may also include a gRNA.

Examples of vectors comprising desired genes in the present invention include a vector that can be replicated in a eukaryotic cell, a vector which maintaining an episome, and a vector incorporated into a host cell genome, and viral vectors are preferred, and adenovirus vectors, lentiviral vectors, and adeno-associated virus vectors are more preferred. Such a vector may include a selection marker. "Selection marker" refers to a genetic element which provides a selectable phenotype to a cell into which the selection marker is introduced, and is commonly a gene of which a gene product imparts resistance to an agent that inhibits cell proliferation or kills or wounds a cell. Specific examples thereof include Neo gene, Hyg gene, hisD gene, Gpt gene, and Ble gene. Examples of a drug useful for selecting the presence of the selection marker include G418 for Neo, hygromycin for Hyg, histidinol for hisD, xanthine for Gpt, and bleomycin for Ble.

(Transfection into Cell)

Transfection of DNA, RNA, and a protein into a cell can be performed by using known optional means or may be performed using a commercially available reagent for transfection. For example, electroporation, Lipofectamine 2000 (Invitrogen), jetPRIME Kit (Polyplus-transfection), DreamFect (OZ Biosciences), GenePorter3000 (OZ Biosciences), Calcium Phosphate Transfection Kit (OZ Biosciences), and the like can be used for transfection of DNA. Electroporation, Lipofectamine 3000 (Invitrogen), RNAi Max (Invitrogen), MessengerMAX (Invitrogen), and the like can be used for transfection of RNA. Electroporation, Lipofectamine CRISPRMAX (Invitrogen), PULSin (Polyplus-transfection), Pro-DeliverIN (OZ Biosciences), BioPORTER Protein Delivery Reagent (Genlantis), and the like can be used for transfection of a protein. Transfection into a cell may also performed by forming a complex of a gRNA and a fusion protein of dCas9 and a tag peptide array, in advance, and transfecting the complex into the cell. DNA, RNA, or a protein can also be introduced into a fertilized egg by microinjection or electroporation.

EXAMPLES

The present invention will be further described below with reference to non-limiting examples. In the present examples, GCN4 was used as a tag peptide. However, the GCN4 can be replaced with another tag peptide.

Example 1. Demethylation of Target Using TET1CD

<Plasmid Construction for Target Demethylation>

A dCas9-TET1 catalytic domain (CD) fusion protein expression vector (pCAG-dCas9TET1CD) was produced by fusing cDNA encoding codon-optimized *S. pyogenes* Cas9 (dCas9) as a catalytically inactive nuclease to a catalytic domain in the N-terminus of human TET1CD (System 1). A dCas9 fragment was amplified from Addgene plasmid 48240 by PCR. A TET1CD fragment was amplified from human cDNA by PCR.

Figure 1:
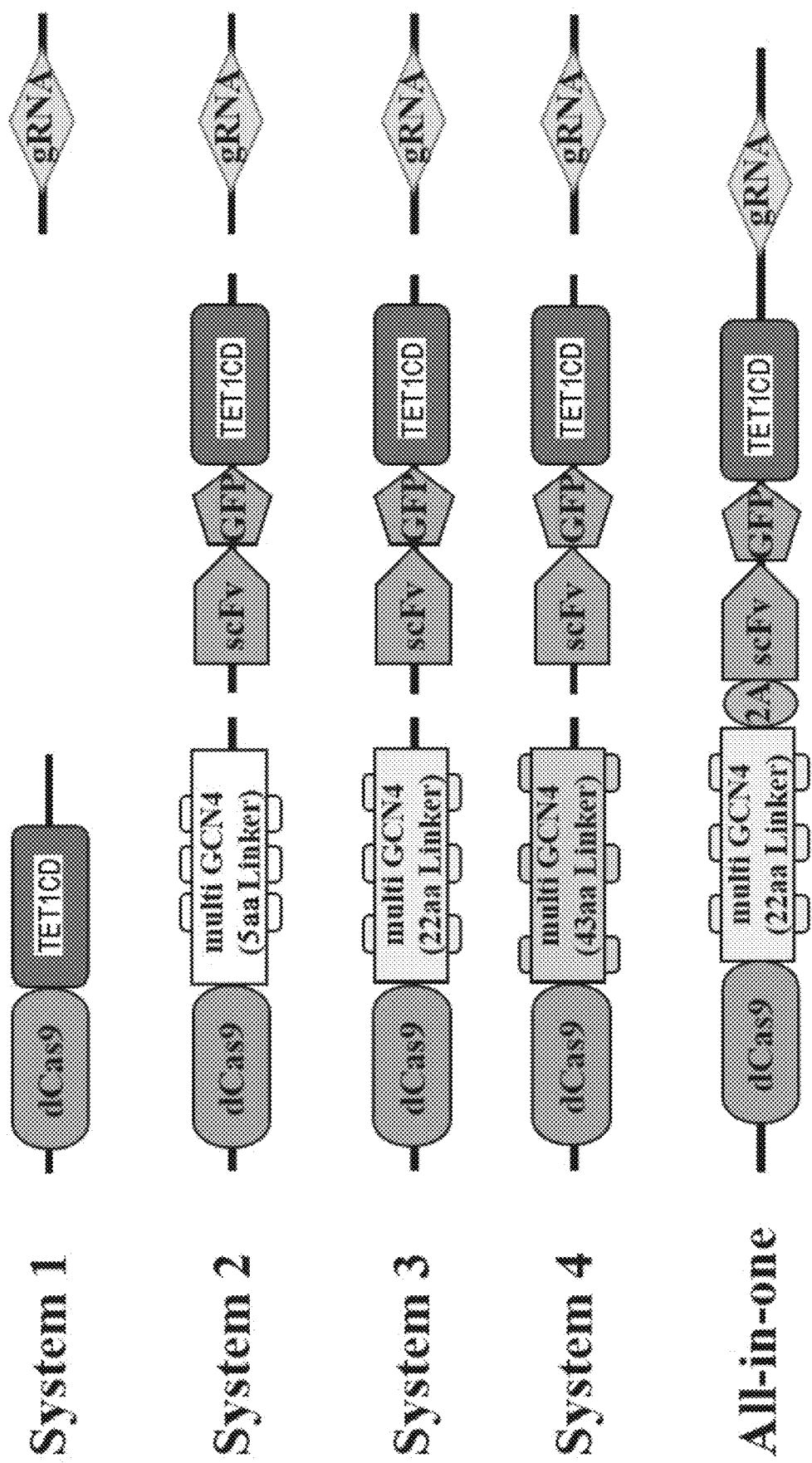
FIG. 1 is a view illustrating the components of transfected vectors (Example 1).

The dCas9 fragments of Systems 1 to 4 in FIG. 1 were amplified from Addgene plasmid 60903 by PCR. The amino acid sequence of used GCN4 was EELLSKNYHLENE-VARLKK (SEQ ID NO: 1). Linker sequences between GCN4 are GSGSG (SEQ ID NO: 2: System 2), GSGSGGSGSGSGGSGSG GSGSG (SEQ ID NO: 3: System 3), and GSGSGGSGSGGSGSGGSGSGGSGSGGSGSGGSGSGGSG SGGSGSG (SEQ ID NO: 4: System 4). A GFP fragment was amplified from Addgene plasmid 60904. An ScFv fragment was also amplified from Addgene plasmid 60904. All the fusion proteins were expressed under the control of a CAG promoter. An all-in-one vector was produced by fusing a 2A peptide (SEQ ID NO: 5: GSGATNFSLLKQAGDVEEN-PGP) into between the components 1 and 2 of System 3. Vector sequences are shown in SEQ ID NOS: 6 to 11 (which are System 1 (pCAG-dCas9TET1CD), dCas9-GCN4 fusion protein of System 2 (pCAG-dCas9-10×GCN4_v4), scFv-TET1CD fusion protein of Systems 2 to 4 (pCAG-scFvGCN4sfGFPTET1CD), dCas9-GCN4 fusion protein of System 3 (pCAG-dCas9-5×Plat2AflD), dCas9-GCN4 fusion protein of System 4 (pCAG-dCas9-3.5×Super), and all-in-one vector (pPlatTET-gRNA2), respectively).

<Construction of gRNA>

A gRNA vector for Gfap or H19 was produced by inserting a target sequence into Addgene plasmid 41824. Cloning was performed by Gibson assembly system via the linearization of an AflII site and the insertion of a gRNA fragment.

Target sequences are set forth in Table 1.

TABLE 1

Target Sequence

| Target Name | Target Sequence | Methylation-Sensitive Site around Target |
|---|---|---|
| Gfap_1 | ATAGACATAATGGTCAGGGGTGG | Gfap STAT3-binding site |
| Gfap_2 | GGAFGCCAGGATGTCAGCCCCGG | Gfap STAT3-binding site |
| Gfap_3 | ATATGGCAAGGGCAGCCCCGTGG | Gfap STAT3-binding site |
| H19DMR_1 | GTGGGGGGCTCTTTAGGTTTGG | H19DMR CTCF-binding site 1 |
| H19DMR_2 | ACCCTGGTCTTTACACACAAAGG | H19DMR CTCF-binding site 2 |
| H19DMR_3 | GAAGCTGTTATGTGCAACAAGGG | H19DMR CTCF-binding site 3 |
| H19DMR_4 | CAGATTTGGCTATAGCTAAATGG | H19DMR CTCF-binding site 4 |

The underlines show PAM sequences.

Unrelated gRNA Sequence

| Target Name | gRNA Sequence |
|---|---|
| UR_1 | CCATTATTGCATTAATCTGA |
| UR_2 | TAATGCAGCCAGAAAATGAC |
| UR_3 | TCAGGGATCAAATTCTGAGC |

<Cell Culture>

Embryonic stem cells (ESCs) were cultured in Dulbecco's modified Eagle's medium-high-concentration glucose (D6429-500ML, Sigma) to which 1% FBS, 17.5% KSR100 (10828028, Gibco), 0.2% of 2-mercaptoethanol (21985-023, Gibco), and $1 \times 10^3$ unit/mL (ESGI 107, Millipore) of ESGRO mLIF were added under 37° C. and 5% $CO_2$. The ESCs were transfected using Lipofectamine 2000 (Invitrogen) according to an attached protocol, and the cells were collected 48 hours after the transfection and directly used for an assay and a sort by FACSAriaII (BD Biosciences).

<DNA Methylation Analysis>

Genomic DNA was treated using Epitect Plus DNA Bisulfite Kit (QIAGEN) according to an attached instruction. The modified DNA was amplified using the following PCR primers in Table 2.

TABLE 2

PCR Primer Sequence for Bisulfite Sequence

| Primer Name | Primer Sequence | Methylation-Sensitive Site around Target |
|---|---|---|
| GfapSTAT3-B3 | TTGGTTAGTTTTTAGGATTTTTTTT | Gfap STAT3-binding site (ES) |
| GfapSTAT3-B4 | AAAACTTCAAACCCATCTATCTCTTC | |
| H19DMR-B1 | AAGGAGATTATGTTTTATTTTTGGA | H19DMR CTCF-binding site 1 |
| H19DMR-B2 | AAAAAAACTCAATCAATTACAATCC | |
| Gfap_O1B1 | TTGTAAAGGTAGGATTAATAAGGGAATT | Gfap off-target site 1 |
| Gfap_O1B2 | AAAAAAAACCCTTCAAAAAAAATCTA | |
| Gfap_O2B1 | TTATTATTTATATTTGGAGGGAGGG | Gfap off-target site 2 |
| Gfap_O2B2 | ATTACACCAAAAAAATTTTAAAAAC | |
| Gfap_O3B1 | TTTAAATTTTTTATGTGAATATGG | Gfap off-target site 3 |
| Gfap_O3B2 | AAACATTTAATTCATTAATACACAC | |

The percentages of the demethylation of the STAT3 site of Gfap and the m1 to m4 sites of H19 were determined by Combined Bisulfite Restriction Analysis (COBRA). The fragments amplified using the primers in Table 3 were cleaved with restriction enzymes having recognition sites in the sites and set forth in in Table 3 below and subjected to polyacrylamide gel electrophoresis.

TABLE 3

COBRA Primer Sequence

| primer name | primer sequence | Restriction enzyme | methylation sensitive site near the targets |
|---|---|---|---|
| GfapSTAT3-B1 | GTTGAAGATTTGGTAGTGTTGAGTT | Hpy188III | Gfap STAT3-binding site |
| GfapSTAT3-B2 | TAAAACATATAACAAAAACAACCCC | | |
| H19DMR-B1 | AAGGAGATTATGTTTTATTTTTGGA | BstUI | H19DMR CTCF-binding site 1 |
| H19DMR-B2 | AAAAAAACTCAATCAATTACAATCC | | |
| H19DMR-B1 | AAGGAGATTATGTTTTATTTTTGGA | RsaI | H19DMR CTCF-binding site 2 |
| H19DMR-B2 | AAAAAAACTCAATCAATTACAATCC | | |
| H19DMR-B3 | GGGTTTTTTTGGTTATTGAATTTTAA | BstUI | H19DMR CTCF-binding site 3 |
| H19DMR-B4 | AATACACACATCTTACCACCCCTATA | | |
| H19DMR-B5 | TTTTTGGGTAGTTTTTTAGTTTTG | BstUI | H19DMR CTCF-binding site 4 |
| H19DMR-B6 | ACACAAATACCTAATCCCTTTATTAAAC | | |

The methylation was calculated as the ratio of cleaved DNA by densitometry analysis of a gel stained with ethidium bromide. In each assay, the methylation of cells transfected with a control vector (empty gRNA vector) was defined as 100% methylation (0% demethylation), and the demethylation of each sample was standardized by the control using the following Numerical Formula 1.

Demethylation of sample (%)=(methylation of control-methylation of sample)/methylation of control×100     Numerical Formula 1

Bisulfite sequencing was carried out for the methylation analysis and off-target analysis of a peripheral region. The amplified fragment was ligated into a TOPO vector (Invitrogen), and sequencing of at least 14 clones was carried out. The sequencing was analyzed by a methylation analysis tool referred to as QUantification tool for Methylation Analysis (QUMA). Statistical significance between two groups of all sets in CpG sites was evaluated using Mann-Whitney U test (also referred to as Wilcoxon matched pairs signed ranks test is called) used for a test of nonparametric statistical significance.

<Results>

First, a simple design which was a direct fusion protein of inactivated Cas9 nuclease (dCas9) and TET1 was produced for methylation treatment. TET1 has a catalytic domain preserved in a C-terminus, and this domain has higher catalytic activity than that of a full-length protein. Therefore, the TET1 catalytic domain (TET1CD) was fused to dCas9 having inactive catalytic action (System 1 in FIG. 1).

A cytosine residue in a STAT3-binding site located upstream of a gene encoding glial fibrillary acidic protein (GFAP) which is an astrocyte-specific marker was used as a target. The site is methylated in many cell types excluding astrocytes, and the demethylation of the site plays an important role in differentiation of neural precursor cells (NPCs) into astrocytes. Three targets around the STAT3-binding site were designed (FIG. 2a), and a gRNA vector for the targets was produced. The gRNA vector was transiently introduced, together with a dCAS9-TET1CD fusion protein expression vector (pCAG-dCas9TET1CD), into embryonic stem cells (ESCs). The methylation of the STAT3-binding site was analyzed by Combined Bisulfite Restriction Analysis (COBRA). In each assay, the methylation of cells into which a gene was introduced together with a control vector (empty gRNA vector) was defined as 0% demethylation (100% methylation), and the demethylation of each sample was standardized by the control.

Figure 2:
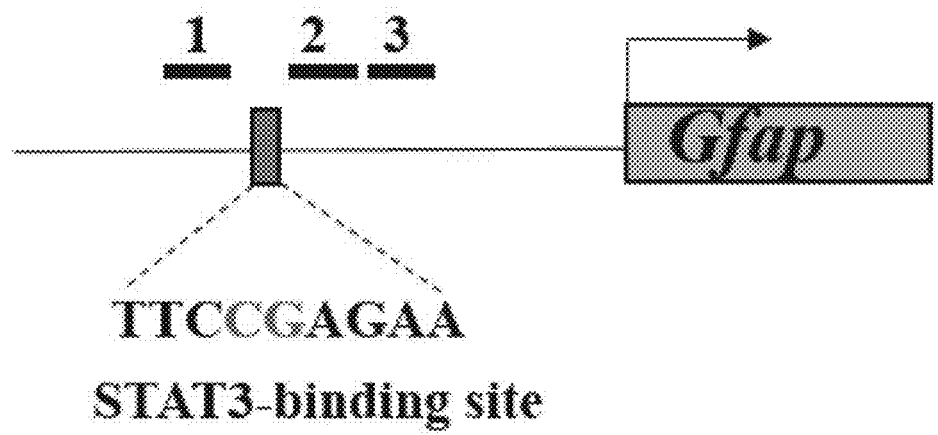
FIG. 2 Section (a) of FIG. 2 is a view illustrating a STAT3 binding site and a mouse Gfap site. The STAT3 binding site has a methylation-sensitive CpG site (CG in TTCCGAGAA)). Targets 1 to 3 used as gRNAs (Gfap1-3) are indicated by black thick bars. Section (b) of FIG. 2 is a graph illustrating the demethylation activity of dCas9 (system 1) directly bound to a TET1 catalytic domain (TET1CD) in which gRNAs targeting Gfap1-3 are used. The ordinate represents a value calculated by the Numerical Formula in the table (the same as the Numerical Formula 1 shown below) as a standardized demethylation percentage (%).
Figure 2:
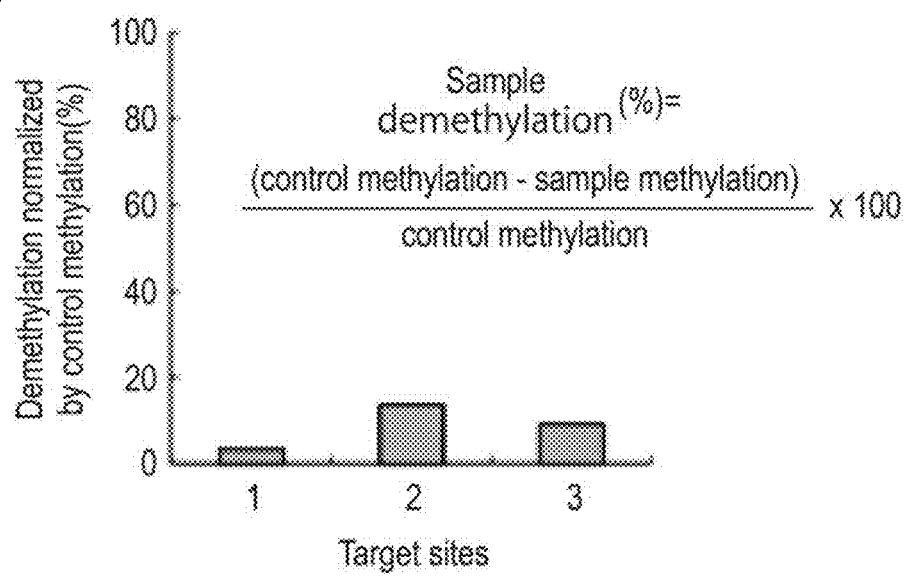

In the STAT3 site, the three gRNAs, Gfap1, Gfap2 and Gfap3, showed demethylations of 3%, 14%, and 9%, respectively (FIG. 2b). In contrast, the unrelated gRNAs (UR1, UR2, and UR3) showed no demethylation. Thus, this simple system induced gRNA-dependent specific demethylation, but the degree of the demethylation was shown to be at most 14%.

Then, an attempt to amplify a demethylation ability was made using dCas9 fused in a repeating peptide sequence in order to recruit plural copies of the antibody fused TET1 hydroxylase catalytic domain (FIG. 3a). For the demethylation of the Gfap STAT3 site, an expression vector of Gfap2gRNA, dCas9 having 10 copies of GCN4 peptides, and a GCN4 peptide antibody (scFv)-superfolder green fluorescent protein (sfGFP)-TET1CD fusion protein was used in ESCs (System 2 in FIG. 1). However, the use of this System 2 did not allow the degree of the demethylation to be improved (FIG. 4a).

Figure 3B:
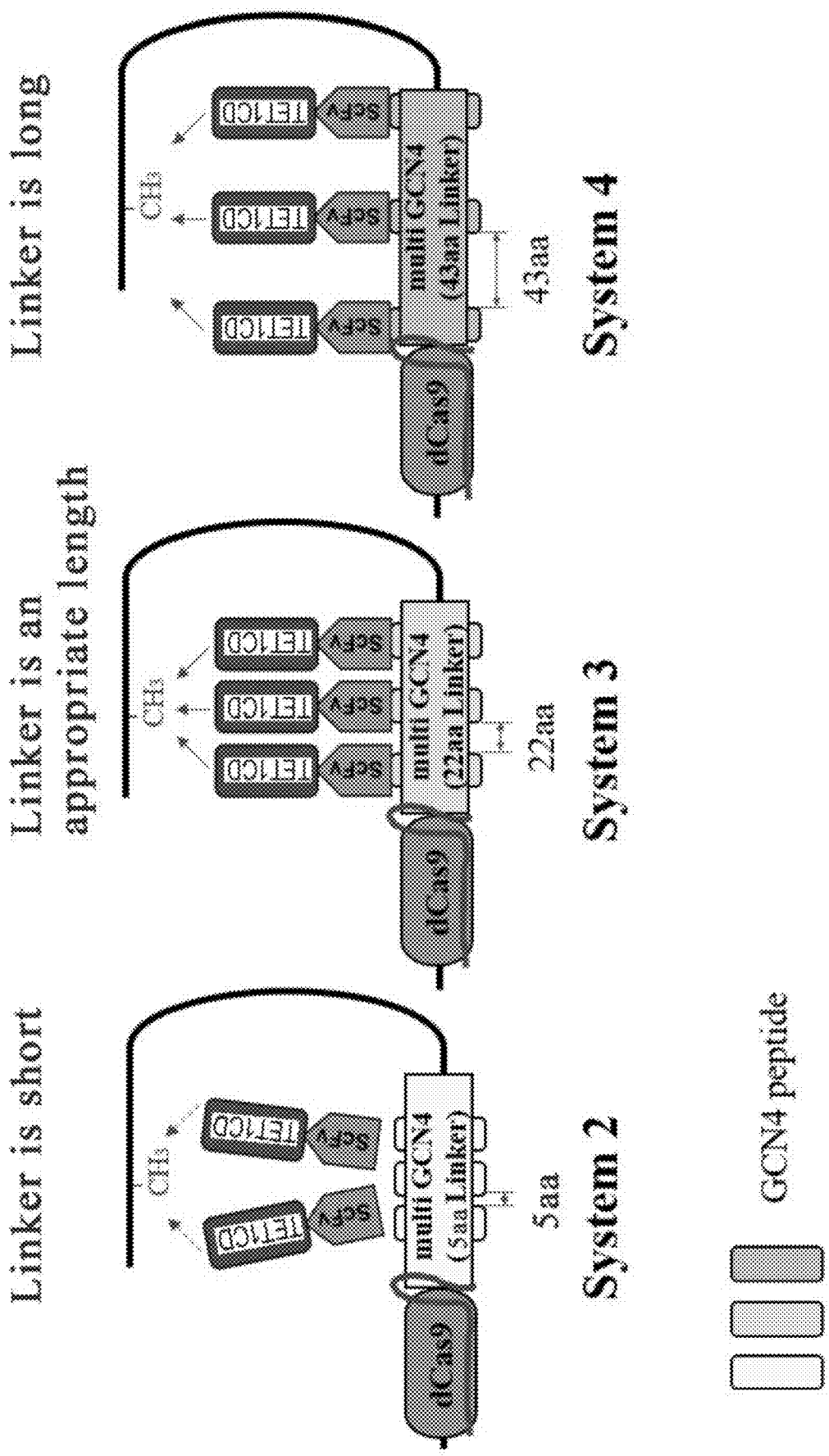
FIG. 3B is a view illustrating a case in which the length of a linker separating each GCN4 peptide epitope fused with dCas9 is too short (left), a case in which the length is appropriate (center), and a case in which the length is too long (right).

The length of a linker by which the sequence of a GCN4 peptide epitope comprising 19 amino acids was separated was examined in order to investigate the reason why System 2 failed to improve the degree of the demethylation. If the length of the linker is too short, it is considered that for the antibody-TET1CD fusion protein, a space for approaching and binding to the GCN4 peptide sequence is too narrow, and therefore, demethylation activity becomes insufficient. If the length of the linker is too long, it is considered that the antibody-TET1CD fusion protein is incapable of approaching a target methylated site (FIG. 3b). The length of the linker of System 2 was 5 amino acids (System 2 in FIG. 1).

A dCas9-GCN4 fusion protein having a linker of which the length was 22 amino acids (System 3 in FIG. 1) and a dCas9-GCN4 fusion protein having a linker of which the length was 43 amino acids (System 4 in FIG. 1) were produced, and the demethylation activities thereof were compared. Because of technological limitation in a synthetic gene technology, the numbers of copies of GCN4 peptides having a linker of which the length was 22 amino acids and a linker of which the length was 43 amino acids were decreased to 5 and 4, respectively. In spite of the decreases in the numbers of the copies of the GCN4 peptides, the linker of which the length was 22 amino acids showed a best demethylation of 43%. The linker of which the length was 44 amino acids showed a second highest activity, and the linker, as a prototype, of which the length was 5 amino acids showed the lowest activity (FIG. 4a).

These results suggested that the length of a linker by which each GCN4 peptide unit sequence fused with dCas9 is separated is more important for demethylation activity than the number of copies of GCN4. The demethylation activity was prominently improved by increasing the length of the linker from 5 amino acids to 22 amino acids. This is considered to be because the 22 amino acids have a width enough for the antibody-TET1CD fusion protein to approach a peptide sequence. In contrast, the linker of which the length was 43 amino acids was considered to be long for the antibody-TET1CD fusion protein to approach a methylated site which was a target.

Cells into which a GFP expression vector was introduced were selected using fluorescence activated cell sorting (FACS) for the purpose of further improving demethylation efficiency. For this purpose, an all-in-one vector comprising a gRNA, dCas9 comprising the GCN4 sequence of System 3, and an antibody-sfGFP-TET1CD fusion protein was produced (FIG. 1). The all-in-one introduced ESCs sorted by GFP showed roughly complete demethylation (FIG. 4).

Figure 4:
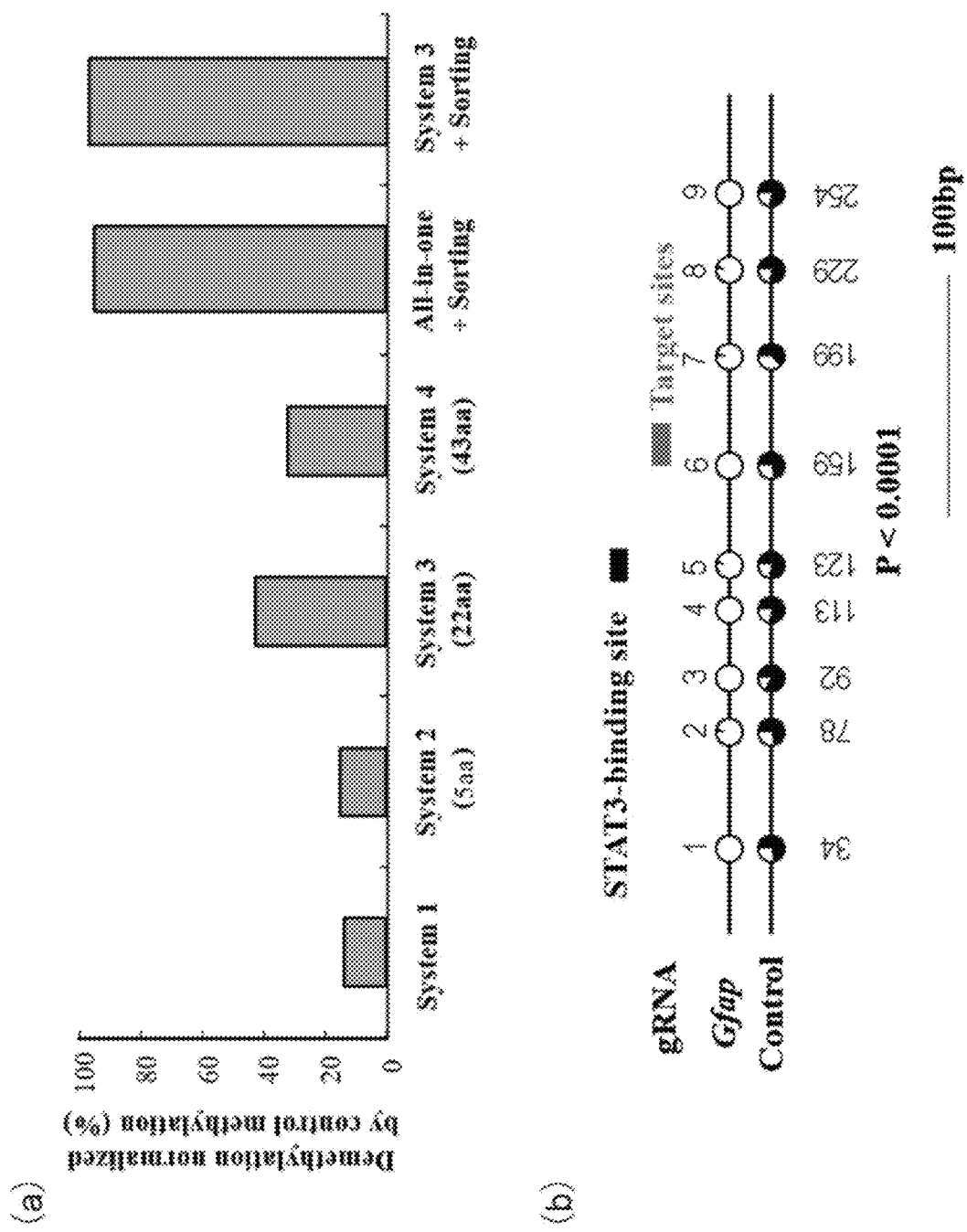
FIG. 4 In section (a) of FIG. 4, the ordinate represents a value calculated by the Numerical Formula 1 shown below as a standardized demethylation percentage (%). The abscissa represents the system of a vector used and the presence or absence of sorting. Target 2 of Gfap was used as a gRNA. Section (b) of FIG. 4 is a view illustrating the methylation in the peripheries of target sites. ESCs transfected with gRNAs targeting system 3 and Gfap2 or a control gRNA were sorted by GFP, and methylation was analyzed by bisulfite sequencing. A black-and-white-style circle represents the percentage of the methylation, and the black represents methylation while the white represents unmethylation. The number under the circle represents each position. Statistical significances between all CpG site sets in the two groups (Gfap and control) were evaluated by Mann-Whitney U test.

The ESCs in to which System 3 was introduced and which was sorted by GFP also unexpectedly showed roughly complete demethylation (FIG. 4). Complete demethylation in a target region was achieved by the promotion of the demethylation ability and the sorting technology.

Figure 5:
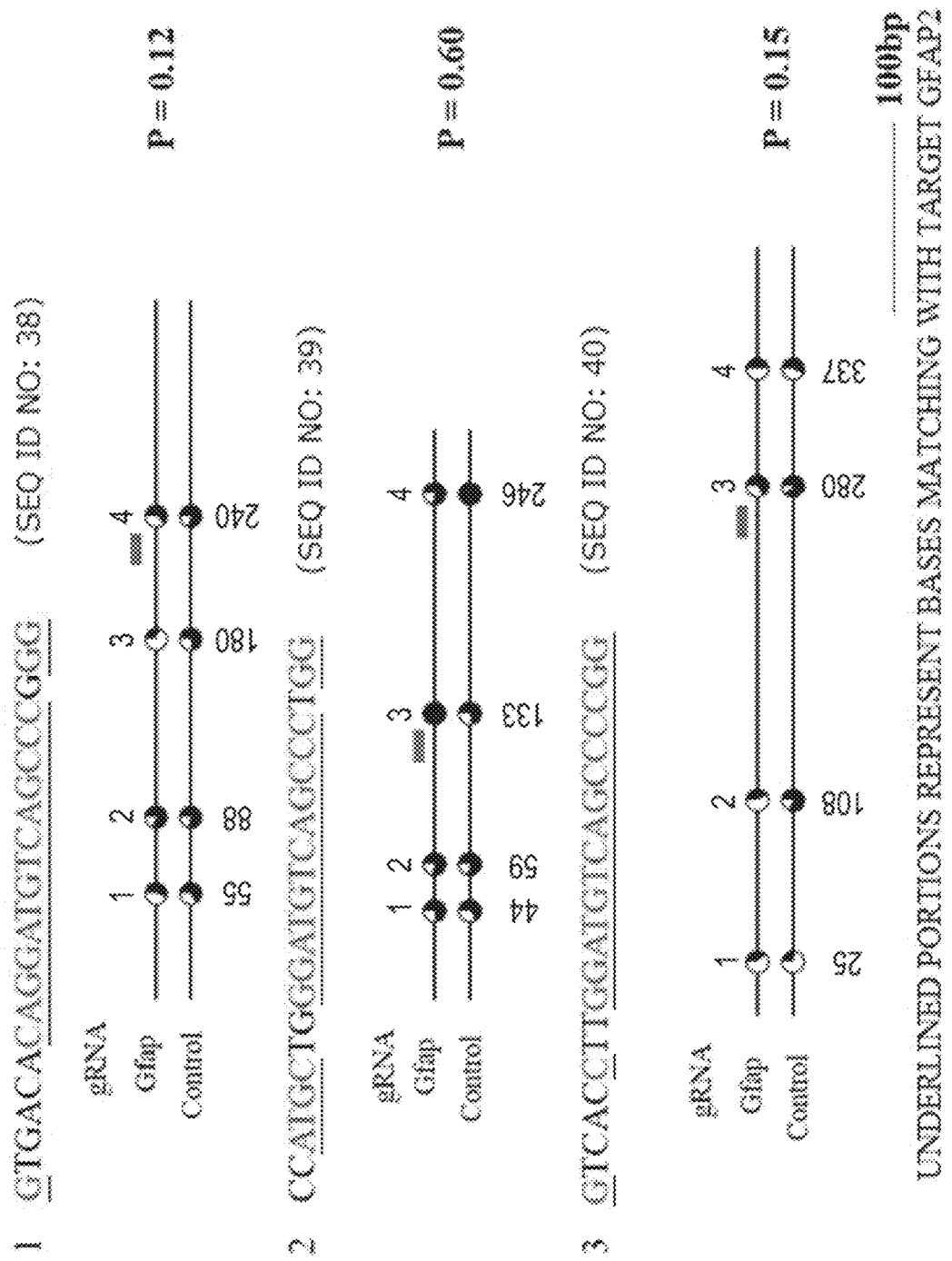
FIG. 5 is a view illustrating the methylation in the peripheries of off-target sites 1 to 3 of a gRNA targeting Gfap2. ESCs transfected with gRNAs targeting system 3 and Gfap2 were sorted by GFP, and the methylation of the peripheries of the off-target sites 1 to 3 was analyzed by bisulfite sequencing. A black-and-white-style circle represents the percentage of the methylation, and the black represents methylation while the white represents unmethylation. The number under the circle represents each position. Statistical significances between all CpG site sets in the two groups (Gfap and control) were evaluated by Mann-Whitney U test. The underlined portions of the sequences represent portions in which Gfap2 targets and nucleotide sequences match with each other.

Then, the range of the demethylation of a used sorted sample from a target site was investigated by bisulfite sequencing. The demethylation occurred even at a site located at least 100 bp or more apart from the target site (FIG. 4b). Investigation of off-target activity by bisulfite sequencing using the same sample resulted in no observation of noticeable off-target activity (FIG. 5).

Figure 6:
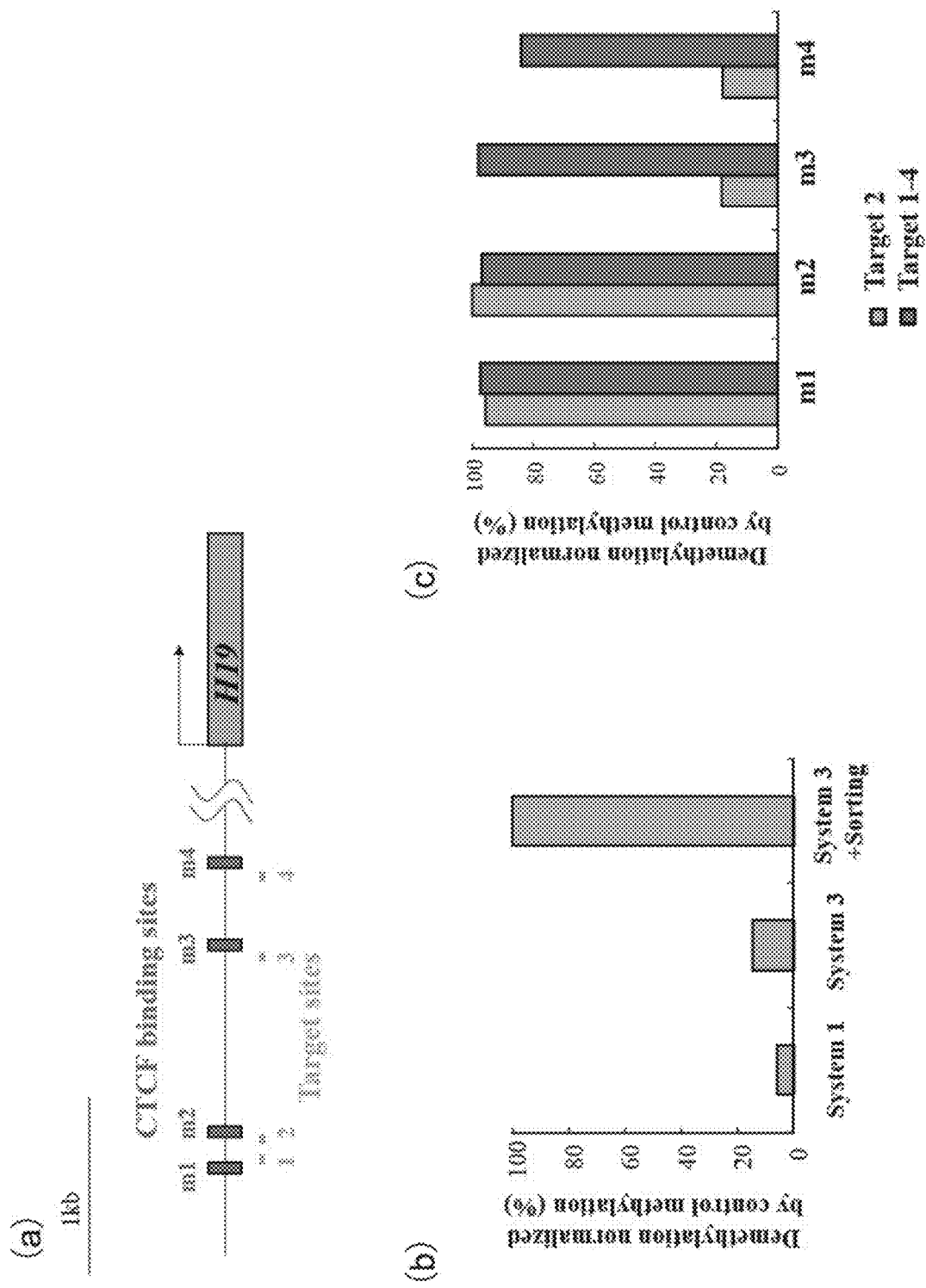
FIG. 6 Section (a) of FIG. 6 illustrates CTCF binding sites and a mouse H19 site. The CTCF binding sites have methylation-sensitive CpG sites (m1 to m4). Sites 1 to 4 used in the targets of gRNAs are illustrated under vertically long bars representing m1 to m4. Section (b) of FIG. 6 illustrates the demethylation of m2 in the CTCF binding sites using systems 1 and 3, and system 3+sorting. The ordinate represents a value calculated by the Numerical Formula 1 shown below as a standardized demethylation percentage (%). The abscissa represents the system of a vector used and the presence or absence of sorting. Section (c) of FIG. 6 is a graph illustrating the demethylation in the CTCF binding sites (m1 to m4) in the case of using system 3+sorting. Left and right bars in each site of m1 to m4 represent demethylation in the case of using the target site 2 as a gRNA and demethylation in the case of using all the gRNAs of the target sites 1 to 4 together, respectively. The ordinate represents a value calculated by the Numerical Formula 1 shown below as a standardized demethylation percentage (%).

Then, a similar experiment was conducted using a differential methylation region (DMR) of H19 as a paternal methylated imprinting gene. The DMR of H19 includes four methylation-sensitive CTCF binding sites (m1 to m4), which are important for adjusting H19 imprinting (FIG. 6a). A gRNA (H19DMR2) targeting m2 was introduced, together with dCas9-TET1CD or System 3, into ESCs. The cells into which System 3 had been introduced and which were subjected to cell sorting after the introduction were also produced.

As a result, noticeable improvement in methylation in System 3 was observed in comparison with dCas9-TET1CD. Complete demethylation was observed at the m2 site in the cells sorted by GFP (FIG. 6b). Further analyzation of the cells sorted by GFP for the methylation of a peripheral region showed complete demethylation at the m1 site located 200 bp apart from the target region (FIG. 6c). In contrast, the slight demethylation of the m3 and m4 sites located 1 kb or more apart from the target site merely occurred (FIG. 6c), and it was suggested that the effect of the demethylation was not greater than that of a site located 1 kb or more apart. In order to test the possibility of targeting of plural of sites, the gRNAs of m1 to m4 were introduced together with System 3 (H19DMR1-4). As a result, roughly complete demethylation was observed in all of the four sites (m1 to m4) in the cells sorted by GFP (FIG. 6c). This showed that plural sites can be demethylated by using plural gRNAs.

Example 2. Methylation of Target Using Dnmt3b

Figure 7:
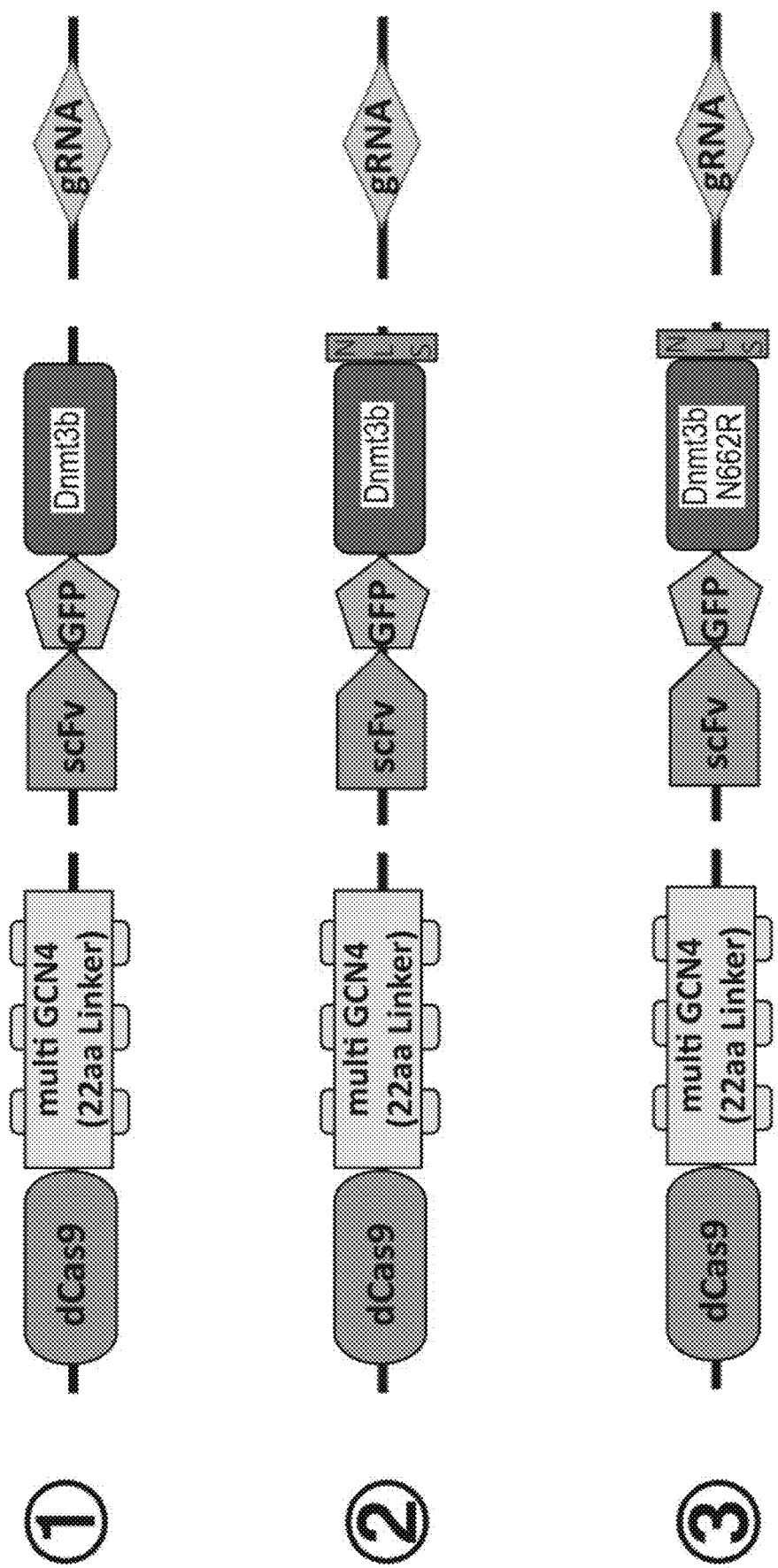
FIG. 7 is a view illustrating the components of transfected vectors (Example 2).

The m2 site of H19 was methylated using System 3 (linker 22aa) in order to introduce methylation into a target. Experiments were conducted using (1) Dnmt3b, (2) Dnmt3bNLS, and (3) Dnmt3bNLS_N662R instead of TET1CD (FIG. 7). (1) is a De novo methylase Dnmt3b, (2) is obtained by adding NLS (nuclear localization signal) to the C terminus of the Dnmt3b of (1), and (3) is obtained by changing the 662nd amino acid of (2) from asparagine (N) to arginine (R). This amino acid substitution has been reported to improve methylation activity (Shen L et al. below). The plasmids used are as follows.

```
(1) Dnmt3b:
                                    (SEQ ID NO: 41)
    pCAG-scFvGCN4sfGFPDnmt3bF (2) Dnmt3bNLS:
                                    (SEQ ID NO: 42)
    pCAG-scFvGCN4sfGFPDnmt3bFNLS (3) Dnmt3bNLS_N662R:
                                    (SEQ ID NO: 43)
    pCAG-scFvGCN4sfGFPDnmt3bS1
```

Figure 8:
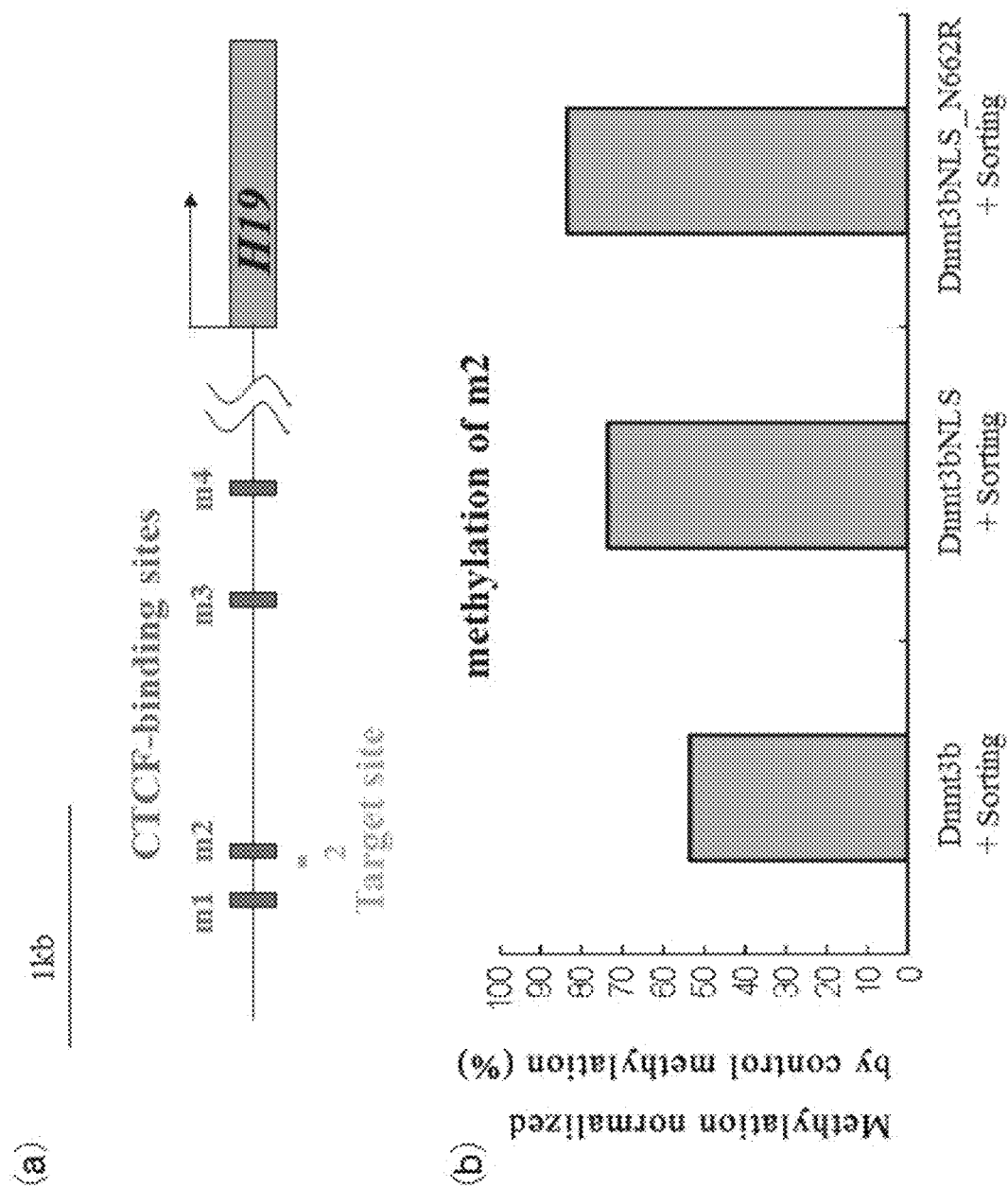
FIG. 8 Section (a) of FIG. 8 illustrates CTCF binding sites and a mouse H19 site. The CTCF binding sites have methylation-sensitive CpG sites (m1 to m4). In Example 2, m2 was used as a target. Section (b) of FIG. 8 illustrates the methylation of m2 in the CTCF binding sites using system 3+sorting. The ordinate represents a value calculated by the following Numerical Formula 2 as a standardized methylation percentage (%).

Only cells into which genes were introduced and which emitted fluorescence were isolated based on fluorescence of GFP by a cell sorter 2 days after introduction of these systems of (1) to (3) into ES cells, and the methylation of the m2 of H19 was examined in a manner similar to that in the demethylation. The methylation was calculated as a methylation (%) standardized by a control, as shown in Numerical Formula 2. As a result, the methylations of the targets were (1) 540%, (2) 74%, and (3) 84%, revealing that methylation efficiency in the case of adding NLS was higher than that in the case of only Dnmt3b, and methylation efficiency in the case of the amino acid substitution of N662R was further higher (FIG. 8).

Methylation (%)standardized by control=(methylation of sample-methylation of control)/methylation of control×100     Numerical Formula 2

REFERENCES

Shen L, Gao G Zhang Y, Zhang H, Ye Z, Huang S, Huang J, Kang J. A single amino acid substitution confers enhanced methylation activity of mammalian Dnmt3b on chromatin DNA. Nucleic Acids Res. 38:6054-6064, 2010. doi: 10.1093/nar/gkq456.
SEQ ID NO: 1: GCN4
SEQ ID NO: 2: linker 5
SEQ ID NO: 32 linker 22
SEQ ID NO: 4: linker 43
SEQ ID NO: 5: 2A peptide
SEQ ID NO: 6: pCAG-dCas9TET1CD
SEQ ID NO: 7: pCAG-dCas9-10×GCN4_v4
SEQ ID NO: 8: pCAG-scFvGCN4sfGFPTET1CD
SEQ ID NO: 9: pCAG-dCas9-5×Plat2AflD
SEQ ID NO: 10: pCAG-dCas9-3.5×Super
SEQ ID NO: 11: pPlatTET-gRNA2
SEQ ID NO: 12: Gfap_1
SEQ ID NO: 13: Gfap_2
SEQ ID NO: 14: Gfap_3
SEQ ID NO: 15: H19DMR_1
SEQ ID NO: 16: H19DMR_2
SEQ ID NO: 17: H19DMR_3
SEQ ID NO: 18: H19DMR_4
SEQ ID NO: 19: UR_1
SEQ ID NO: 20: UR_2
SEQ ID NO: 21: UR_3
SEQ ID NO: 22: GfapSTAT3-B3
SEQ ID NO: 23: GfapSTAT3-B4
SEQ ID NO: 24: H19DMR-B1
SEQ ID NO: 25: H19DMR-B2
SEQ ID NO: 26: Gfap_O1B1
SEQ ID NO: 27: Gfap_O1B2
SEQ ID NO: 28: Gfap_O2B1
SEQ ID NO: 29: Gfap_O2B2
SEQ ID NO: 30: Gfap_O3B1
SEQ ID NO: 31: Gfap_O3B2
SEQ ID NO: 32: GfapSTAT3-B1
SEQ ID NO: 33: GfapSTAT3-B2
SEQ ID NO: 34: H19DMR-B3
SEQ ID NO: 35: H19DMR-B4
SEQ ID NO: 36: H19DMR-B5
SEQ ID NO: 37: H19DMR-B6
SEQ ID NO: 38: off target 1
SEQ ID NO: 39: off target 2
SEQ ID NO: 40: off target 3
SEQ ID NO: 41: pCAG-scFvGCN4sfGFPDnmt3bF
SEQ ID NO: 42: pCAG-scFvGCN4sfGFPDnmt3bFNLS
SEQ ID NO: 43: pCAG-scFvGCN4sfGFPDnmt3bS1
SEQ ID NO: 44: tag peptide GVKESLV
SEQ ID NO: 45: GS linker
SEQ ID NO: 46: GS linker
SEQ ID NO: 47: GS linker

INDUSTRIAL APPLICABILITY

The methylation of a particular gene can be controlled according to the present invention. As a result, model cells and animals with diseases (epigenome diseases) occurring due to DNA methylation abnormality, such as cancers and imprinting diseases, can be produced. In addition, virus vectors and other delivery systems can be used for treatment of the diseases. In production of iPS cells, the iPS cells can be effectively produced by demethylating and activating a pluripotent gene such as Oct-4 according to the present invention.

What is claimed is:

1. A DNA methylation editing method comprising introducing into a cultured cell the following (1) to (3):
   (1) a first fusion protein comprising: (i) inactivated CRISPR-associated endonuclease Cas9 (dCas9) having no nuclease activity and (ii) a tag peptide array comprising a plurality of tag peptides and peptide linkers which consists of 15-50 amino acids and link the tag peptides, or an RNA or DNA coding the first fusion protein, wherein the tag peptides are peptide epitopes, and wherein the peptide epitopes are general control non-derepressible 4 (GCN4) peptide epitopes;
   (2) a second fusion protein(s) comprising a tag peptide-binding portion and a methylase or demethylase, or an RNA(s) or DNA(s) coding the second fusion protein, wherein the tag peptide-binding portion is an anti-peptide-epitope antibody and the anti-peptide epitope antibody is an anti-GCN4 peptide epitope antibody, and wherein the demethylase is a catalytic domain of ten-eleven translocation 1 (TET1CD) and the methylase is DNA methyltransferase 3 beta (DNMT2B); and
   (3) a guide RNA(s) (gRNA(s)) comprising a sequence complementary to a DNA sequence within 1kb of a desired site of methylation or demethylation, or a DNA(s) expressing the gRNA(s); and wherein DNA methylation editing occurs and comprises methylation of a DNA unmethylated site or demethylation of a DNA methylated site.

2. The DNA methylation editing method according to claim 1, wherein the fusion proteins of the (1) and/or (2) further comprise a selection marker.

3. The DNA methylation editing method according to claim 2, further comprising selecting and collecting a cell expressing the selection marker as a part of the fusion protein.

* * * * *